US009551002B2

(12) United States Patent
Coruzzi et al.

(10) Patent No.: US 9,551,002 B2
(45) Date of Patent: *Jan. 24, 2017

(54) PERICYCLE-SPECIFIC EXPRESSION OF MICRORNA167 IN PLANTS

(71) Applicant: New York University, New York, NY (US)

(72) Inventors: Gloria Coruzzi, New York, NY (US); Kenneth D. Birnbaum, Brooklyn, NY (US); Rodrigo A. Gutierrez, Santiago (CH); Miriam Gifford, New York, NY (US)

(73) Assignee: New York University, New York, NY (US)

( * ) Notice: Subject to any disclaimer, the term of this patent is extended or adjusted under 35 U.S.C. 154(b) by 204 days.

This patent is subject to a terminal disclaimer.

(21) Appl. No.: 14/134,624

(22) Filed: Dec. 19, 2013

(65) Prior Publication Data

US 2014/0283217 A1    Sep. 18, 2014

Related U.S. Application Data

(63) Continuation of application No. 12/077,294, filed on Mar. 17, 2008, now Pat. No. 8,624,084.

(60) Provisional application No. 60/918,443, filed on Mar. 16, 2007.

(51) Int. Cl.
 *C12N 15/82* (2006.01)

(52) U.S. Cl.
 CPC ....... *C12N 15/8241* (2013.01); *C12N 15/8218* (2013.01); *C12N 15/8261* (2013.01)

(58) Field of Classification Search
 None
 See application file for complete search history.

(56) References Cited

U.S. PATENT DOCUMENTS

| | | | |
|---|---|---|---|
| 3,964,496 A * | 6/1976 | White ..................... | A24B 15/30 131/359 |
| 5,256,558 A | 10/1993 | Coruzzi et al. | |
| 5,294,593 A | 3/1994 | Khan et al. | |
| 5,391,725 A | 2/1995 | Coruzzi et al. | |
| 5,595,896 A | 1/1997 | Coruzzi et al. | |
| 5,723,746 A * | 3/1998 | Bestwick ................ | C12N 9/14 435/320.1 |
| 5,824,857 A | 10/1998 | Beachy et al. | |
| 5,955,651 A | 9/1999 | Coruzzi et al. | |
| 5,959,174 A | 9/1999 | Coruzzi et al. | |
| 5,981,703 A | 11/1999 | Coruzzi et al. | |
| 6,031,156 A | 2/2000 | Coruzzi et al. | |
| 6,107,547 A | 8/2000 | Coruzzi et al. | |
| 6,177,275 B1 | 1/2001 | Coruzzi et al. | |
| 6,451,546 B1 | 9/2002 | Coruzzi et al. | |
| 6,822,079 B2 | 11/2004 | Coruzzi et al. | |
| 6,864,405 B1 | 3/2005 | Coruzzi et al. | |
| 8,624,084 B2 * | 1/2014 | Coruzzi ............ | C12N 15/8218 435/320.1 |
| 2009/0083876 A1 | 3/2009 | Coruzzi et al. | |

FOREIGN PATENT DOCUMENTS

| EP | 116718 | 8/1984 |
|---|---|---|
| WO | WO 93/22443 | 11/1993 |

OTHER PUBLICATIONS

Tripp et al. Arabidopsis thaliana putative DNA-binding protein (At3g61310) mRNA, complete cds. (2002) GenBank Accession AY128386.1; pp. 1-2.*
Kim et al. Arabidopsis thaliana At3g61310 mRNA, complete cds. (2003) GenBank Accession BT009937.1; pp. 1-2.*
Werner et al. Cytokinin-deficient transgenic *Arabidopsis* plants show multiple developmental alterations indicating opposite functions of cytokinins in the regulation of shoot and root meristem activity. (2003) The Plant Cell; vol. 15; pp. 2532-2550.*
Barabasi et al., 2004, "Network biology: understanding the cell's functional organization", Nature Rev. Genet. 5:101-113.
Birnbaum et al., 2003. "A gene expression map of the Arabidopsis root", Science 302:1956-1960.
Birnbaum et al., 2005, "Cell type-specific expression profiling in plants via cell sorting of protoplasts from fluorescent reporter lines", Nature Meth. 2:615-619.
Bonke et al.. 2003, "APL regulates vascular tissue identity in Arabidopsis". Nature 426:181-186.
Coruzzi et al., 1983, "Nucleotide sequences of two pea cDNA clones encoding the small subunit of ribulose 1,5-bisphosphate carboxylase and the major chlorophyll a/b-binding thylakoid polypeptide", J. Biol. Chem. 258:1399-1402.
Coruzzi et al., 1984, "Tissue-specific and light-regulated expression of a pea nuclear gene encoding the small subunit of ribulose-1,5-bisphosphate carboxylase", EMBO J. 3:1671-1679.
Craigon et al., 2004, "NASCArrays: a repository or microarray data generated by NASC's transcriptomics service", Nucl. Acids Res. 32:D575-D577.
De Smet et al., 2007. "Auxin-dependent regulation of lateral root positioning in the basal meristem of Arabidopsis", Development 134:681-690.

(Continued)

*Primary Examiner* — Cathy Kingdon Worley
(74) *Attorney, Agent, or Firm* — Jones Day

(57) ABSTRACT

Provided herein are compositions and methods for producing transgenic plants. In specific embodiments, transgenic plants comprise a construct comprising a polynucleotide encoding microRNA167 (miR167), or precursor thereof, operably linked to a plant pericycle-specific promote, wherein the miR167 is ectopically overexpressed in the transgenic plants, and wherein the promoter is optionally a constitutive or inducible promoter. In some embodiments, the transgenic plant has an improved agronomic or nutritional characteristic when cultivated in nitrogen-rich conditions as compared to a wild type plant cultivated in the same conditions. Also provided herein are commercial products (e.g., pulp, paper, paper products, or lumber) derived from the transgenic plants (e.g., transgenic trees) produced using the methods provided herein.

4 Claims, 12 Drawing Sheets

(56) References Cited

OTHER PUBLICATIONS

Figure 1B:
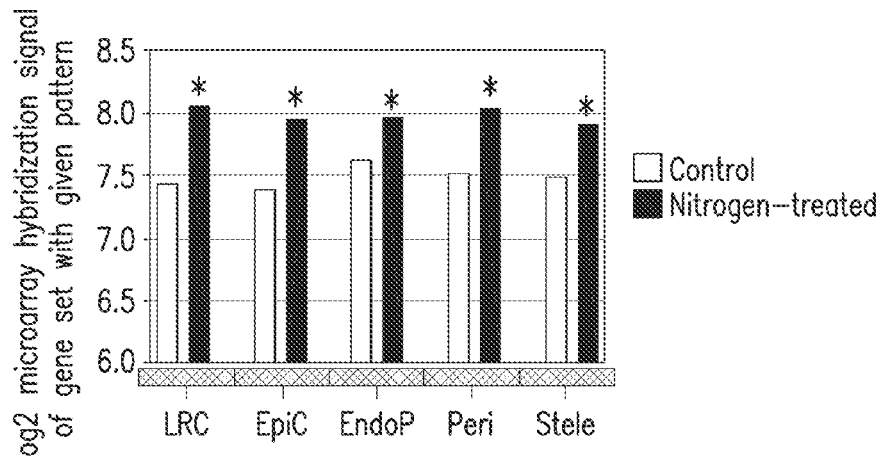

Dezulian et al., 2006, "Identification of plant microRNA homologs", Bioinformatics 22:359-360.
Evans, 1985, "Binding, Regeneration of Plants" in: Plant Protoplasts, Fowke & Constabel, eds., CRC Press, Boca Raton, FL, pp. 21-73.
Finer and McMullen, 1991, "Transformation of soybean via particle bombardment of embryogenic suspension culture tissue", In Vitro Cell and Develop. Biol—Plant 27P:175-182.
Fromm et al., 1985, "Expression of genes transferred into monocot and dicot plant cells by electroporation", Proc. Natl. Acad. Sci. USA 82:5824-5828.
Guo et al., 2005, "MicroRNA directs mRNA cleavage of the transcription factor NAC1 to downregulate auxin signals for arabidopsis lateral root development", Plant Cell 17:1376-1386.
Gutierrez et al. 2007, "Qualitative network models and genome-wide expression data define carbon/nitrogen-responsive molecular machines in Arabidopsis", Genome Biol. 8R7.
Higgins and Sharp, 1989, "Fast and sensitive multiple sequence alignments on a microcomputer", CABIOS 5:151-153.
Himanen et al., 2004, "Transcript profiling of early lateral root initiation", Proc. Natl. Acad. Sci. USA 101:5146-5151.
Imai et al., 2006, "The A-type cyclin CYCA2;3 is a key regulator of ploidy levels in Arabidopsis endoreduplication", Plant Cell 18:382-396.
Little et al., 2005, "The putative high-affinity nitrate transporter NRT2.1 represses lateral root initiation in response to nutritional cues", Proc. Natl. Acad. Sci. USA 102:13693-13698.
Llave et al., 2002, "Endogenous and silencing-associated small RNAs in plants", Plant Cell 14:1605-1619.
Lopez-Bucio et al., 2003, "The role of nutrient availability in regulating root architecture", Curr. Opin. Plant Biol. 6:280-287.
Malamy and Benfey, 1997, "Organization and cell differentiation in lateral roots of Arabidopsis thaliana", Development 124:33-44.
Malamy, 2005, "Intrinsic and environmental response pathways that regulate root system architecture", Plant Cell Environ., 28:67-77.
McManus et al., 2002, "Gene silencing using micro-RNA designed hairpins", RNA 8:842-850.
Meinkoth and Wahl, 1984, "Hybridization of nucleic acids immobilized on solid supports", Anal. Biochem. 138:267-284.
Okushima et al., 2007, "ARF7 and ARF19 regulate lateral root formation via direct activation of LBD/ASL genes in Arabidopsis", Plant Cell 19:118-130.
Palenchar et al., 2004, "Genome-wide patterns of carbon and nitrogen regulation of gene expression validate the combined carbon and nitrogen (CN)-signaling hypothesis in plants", Genome Biol. 5:R91.1-R91.15.
Palma et al., 2006, "Antioxidative enzymes from chloroplasts, mitochondria, and peroxisomes during leaf senescence of nodulated pea plants", J. Exp. Bot. 57:1747-1758.
Rawat et al., 1999, "AtAMT1 gene expression and NH4+ uptake in roots of Arabidopsis thaliana: evidence for regulation by root glutamine levels", Plant J. 19:143-152.
Remans et al., 2006, "The Arabidopsis NRT1.1 transporter participates in the signaling pathway triggering rout colonization of nitrate-rich patches", Proc. Natl. Acad. Sci. USA 103:19206-19211.
Sessions et al., 1999, "The Arabidopsis thaliana MERISTEM LAYER 1 promoter specifies epidermal expression in meristems and young primordia". Plant J. 20:259-263.
Shani et al., 2006, "Expression of endo-1,4-beta-glucanase (cell) in Arabidopsis thaliana is associated with plant growth, xylem development and cell wall thickening", Plant Cell Rep. 25:1067-1074.
Tian et al., 2004, "Disruption and overexpression of auxin response factor 8 gene of Arabidopsis affect hypocotyl elongation and root growth habit, indicating its possible involvement in auxin homeostasis in light condition". Plant J. 40:333-343.
Tian et al., 2004, "High-throughput fluorescent tagging of full-length Arabidopsis gene products in planta", Plant Physiol. 135:25-38.
Tusher et al., 2001, "Significance analysis of microarrays applied to the ionizing radiation response", Proc. Natl. Acad. Sci. USA 98:5116-5121 (and correction at 98:10515).
Vitousek et al., 1991, "Nitrogen limitation on land and in the sea: How can it occur?", Biogeochemistry. 13:87-115.
Walch-Liu et al., 2006, "Nitrogen rogen regulation of root branching", Ann Bot (lond) 97:875-881.
Walch-Liu et al., 2006, "Evidence that L-glutamate can act as an exogenous signal to modulate root growth and branching in Arabidopsis thaliana", Plant Cell Physiol. 47L 1045-1057.
Wang et al., 2003, "Microarray analysis of the nitrate response in Arabidopsis roots and shoots reveals over 1,000 rapidly responding genes and new linkages to glucose, trehalose-6-phosphate, iron, and sulfate metabolism", Plant Physiol. 132:556-567.
Wang et al., 2004, "Genomic analysis of the nitrate response using a nitrate reductase-null mutant of Arabidopsis", Plant Physol. 136:2512-2522.
Wu et al., 2006, "Arabidopsis microRNA167 controls patterns of ARF6 and ARF8 expression, and regulates both female and male reproduction", Development 133:4211-4218.
Zhang and Forde, 1998, "An Arabidopsis MADS box gene that controls nutrient-induced changes in root architecture", Science 279:407-409.
Zhang et al., 1999, "Dual pathways for regulation of root branching by nitrate", Proc. Natl. Acad. Sci, USA 96:6529-6534.
Zhang and Forde, 2000, "Regulation of Arabidopsis root development by nitrate availability", J. Exp. Bot. 51:51-59.
Ru et al., 2006, "Plant fertility defects induced by the enhanced expression of microRNA 167", Cell Res. 16:457-465.
Dubrovsky et al., 2000, "Pericycle cell proliferation and lateral root initiation in *Arabidopsis*", Plant Physiol. 124(4):1648-1657.
Takano et al., 2005, "Endocytosis and degradation of bor1, a boron transporter of *Arabidopsis thaliana*, regulated by boron availability", Proc. Natl. Acad. Sci. USA. 102(34):12276-12281.
Ames, M., "A review of factors affecting plant growth". Online article, Retrievable from: <URL: http://www.hydrofarm.com/resources/articles/factors_plantgrowth.php>.
McDougall et al., 2002, "Guide to the GTAP data base", In *Global Trade, Assistance, and Production: The GTAP 5 Data Base*: Editors: Dimarana and McDougall; pp. 8-1-8-18.

* cited by examiner

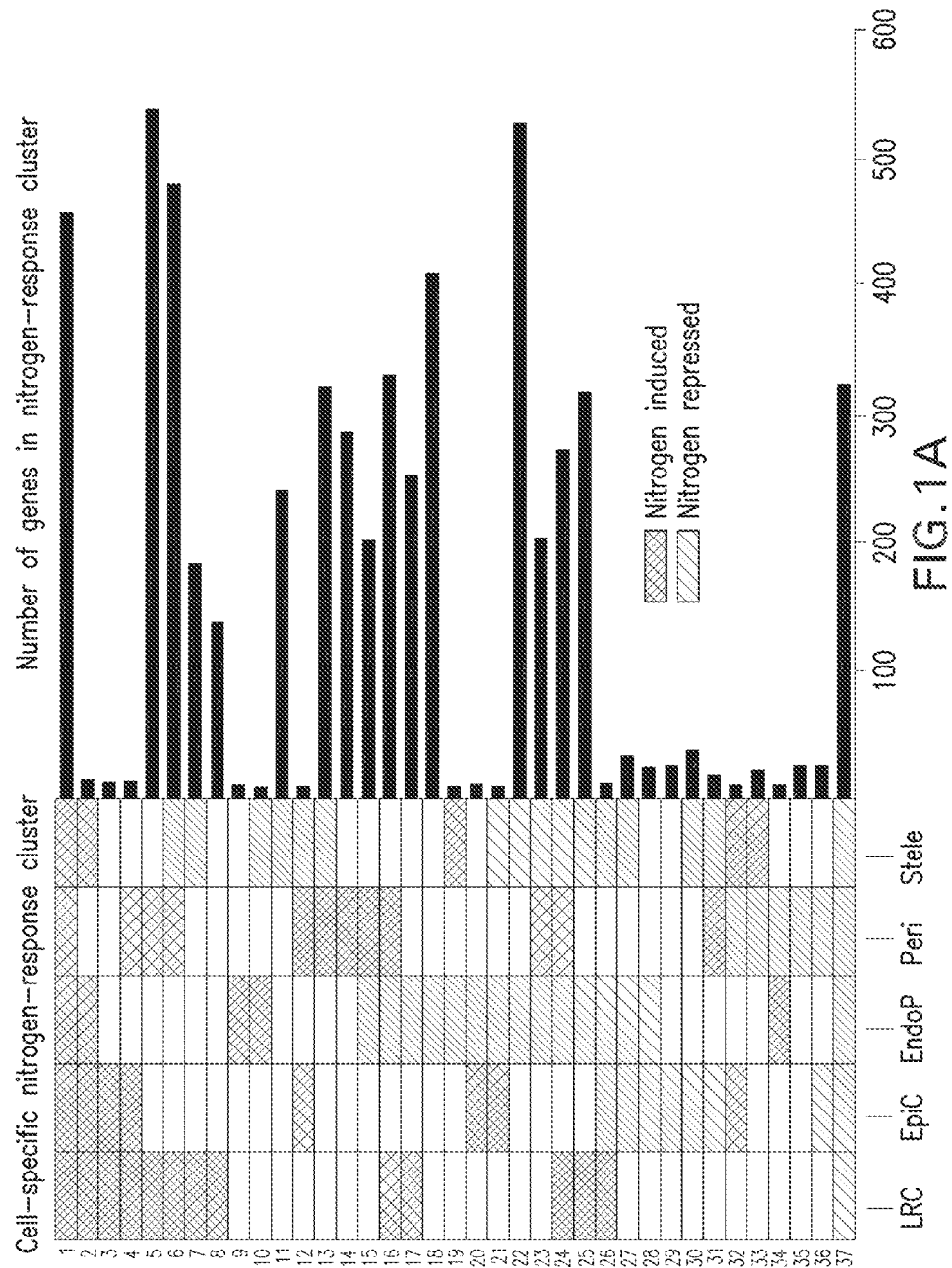

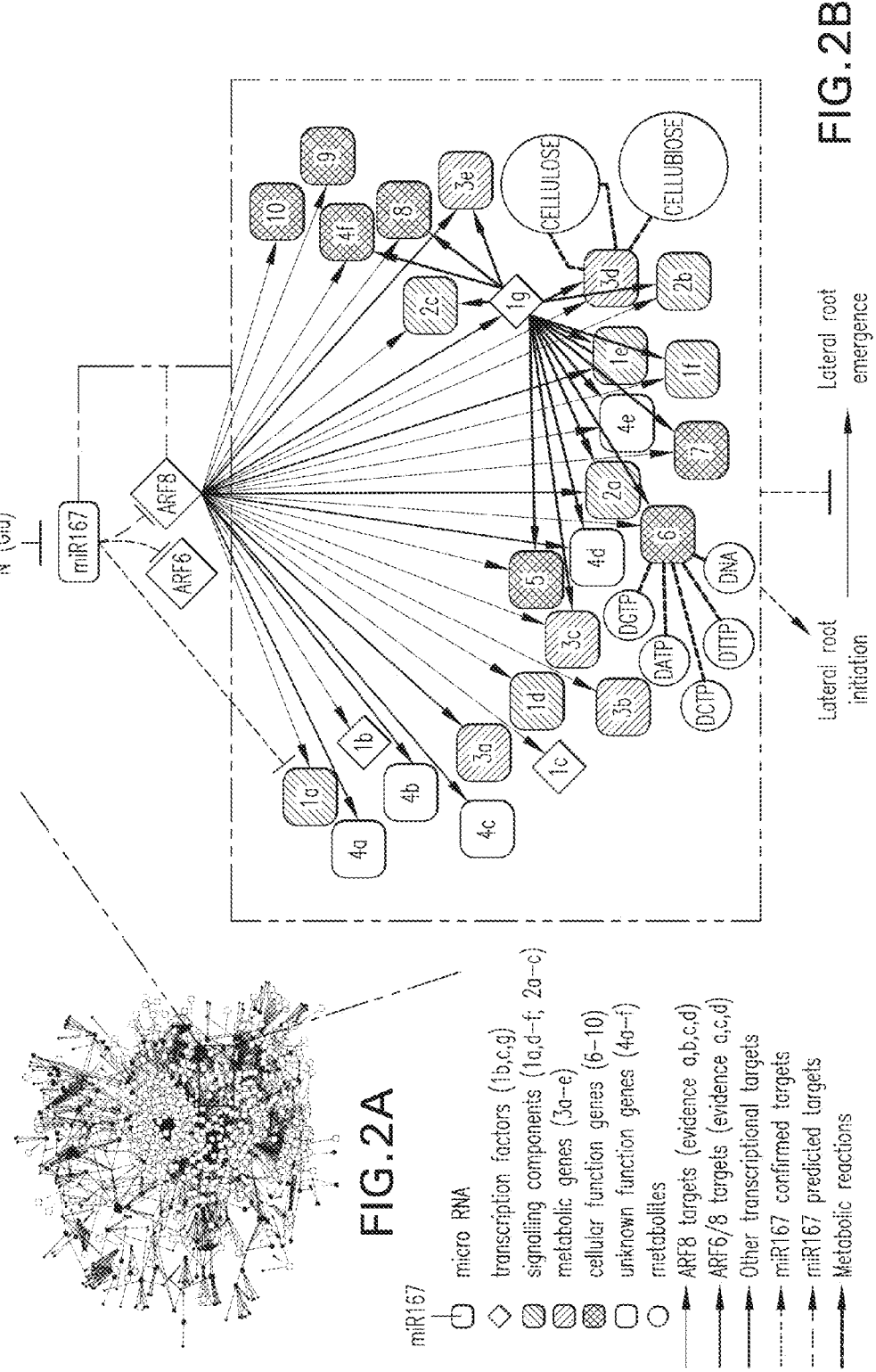

Figure 3J:
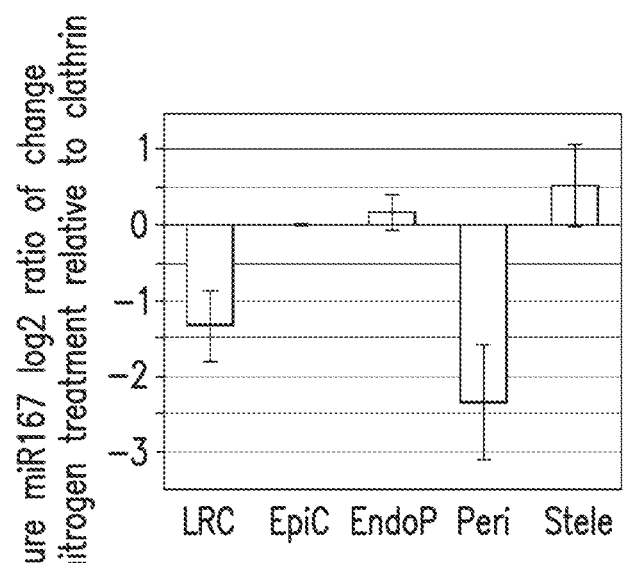
Figure 3K:
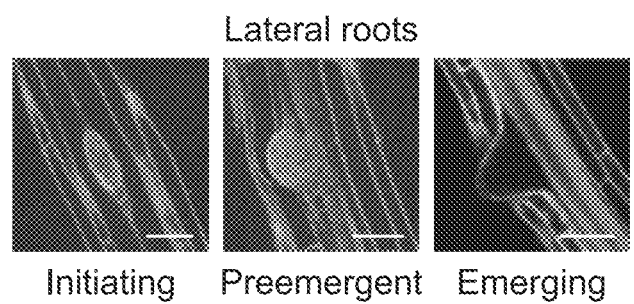

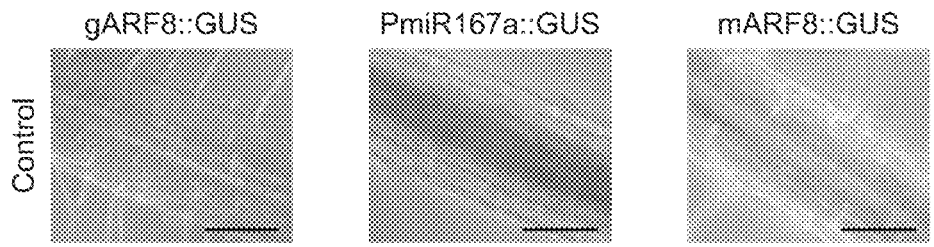
FIG.3A  FIG.3D  FIG.3G
FIG.3B  FIG.3E  FIG.3H
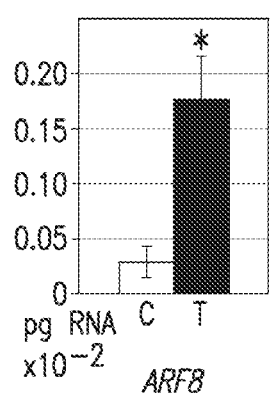
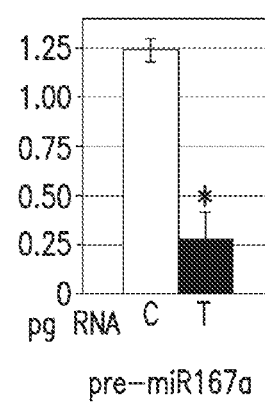
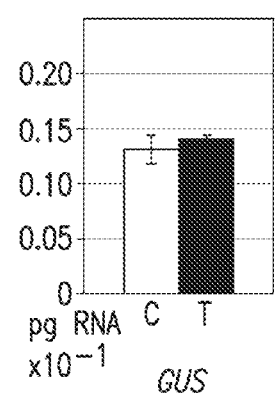
FIG.3C  FIG.3F  FIG.3I

| Key | AGI ID | Gene Description |
|---|---|---|
| 1a | At3g61310 | DNA-binding family protein |
| 1b | At1g76420 | No apical meristem (NAM) family protein |
| 1c | At1g24260 | Member of the MADs box transcription factor family |
| 1d | At1g79350 | DNA-binding protein |
| 1e | At1g63470 | DNA-binding family protein |
| 1f | At2g20100 | Ethylene-responsive family protein |
| 1g | At3g45610 | Dof-type zinc finger domain-containing protein |
| 2a | At2g26330 | Homologous to receptor protein kinases |
| 2b | At3g57830 | Leucine-rich repeat transmembrane protein kinase |
| 2c | At2g01210 | Leucine-rich repeat transmembrane protein kinase |
| 3a | At3g16170 | Acyl-activating enzyme 13 (AAE13) |
| 3b | At1g48100 | Glycoside hydrolase family 28 protein / polygalacturonase (pectinase) family protein |
| 3c | At1g11730 | Galactosyltransferase family protein |
| 3d | At1g70710 | CEL1 Endo-1,4-beta-glucanase (EGASE) |
| 3e | At1g32830 | Galactosyltransferase family protein |
| 4a | At3g13900 | Expressed protein |
| 4b | At2g38160 | Expressed protein |
| 4c | At1g03170 | Expressed protein |
| 4d | At3g13510 | Expressed protein |
| 4e | At2g23700 | Expressed protein |
| 4f | At3g11000 | Expressed protein |
| 5 | At3g10310 | Kinesin motor protein-related |
| 6 | At2g42120 | DNA polymerase delta small subunit-related |
| 7 | At1g15570 | Cyclin A2;3 |
| 8 | At2g26180 | Calmodulin-binding family protein |
| 9 | At1g67520 | DNA primase |
| 10 | At2g44440 | Emsy N terminus domain-containing protein / ENT domain-containing protein |

FIG. 4

| AGI ID | Affy probe ID | Gene Name | LRC CC | LRC TC | LRC TT | EpiC CC | EpiC TC | EpiC TT |
|---|---|---|---|---|---|---|---|---|
| At1g22710 | 264204_at | SUC2 | 6.60 | 6.67 | 6.75 | 6.25 | 6.51 | 6.37 |
| At1g50420 | 261866_at | SCL3 | 6.85 | 6.99 | 6.74 | 7.14 | 7.13 | 6.80 |
| At1g70940 | 262263_at | PIN3 | 6.38 | 6.39 | 6.44 | 5.91 | 6.01 | 5.91 |
| At1g73590 | 259845_at | PIN1 | 5.76 | 6.07 | 6.10 | 5.62 | 5.70 | 5.62 |
| At1g73590 | 259845_at | PIN1 | 5.76 | 6.07 | 6.10 | 5.62 | 5.70 | 5.62 |
| At1g79840 | 260166_at | GL2 | 6.70 | 7.43 | 7.66 | 6.88 | 7.03 | 7.00 |
| At2g01420 | 266300_at | PIN4 | 7.12 | 6.94 | 7.80 | 7.60 | 7.35 | 7.84 |
| At2g01830 | 263599_at | WOL | 7.82 | 7.68 | 7.70 | 7.51 | 7.67 | 7.43 |
| At2g34650 | 266908_at | PINOID | 7.74 | 8.64 | 7.99 | 8.09 | 8.14 | 8.54 |
| At2g37180 | 265444_s_at | PIP2 | 8.30 | 7.90 | 7.98 | 10.82 | 10.92 | 10.83 |
| At2g38120 | 267092_at | AUX1 | 9.17 | 9.80 | 9.58 | 8.92 | 9.14 | 9.07 |
| At2g46410 | 263775_at | CPC | 6.74 | 6.80 | 6.87 | 7.27 | 7.43 | 7.98 |
| At3g13870 | 257606_at | RHD3 | 8.11 | 8.12 | 7.90 | 8.39 | 8.22 | 8.16 |
| At3g54220 | 251890_at | SCR | 6.75 | 6.97 | 6.86 | 7.24 | 7.34 | 7.14 |
| At4g14940 | 245584_at | ATAO1 | 9.90 | 9.94 | 10.43 | 8.54 | 8.28 | 8.51 |
| At4g22200 | 254305_at | AKT2 | 5.49 | 4.70 | 5.48 | 5.26 | 5.20 | 4.92 |
| At4g32880 | 253402_at | ATHB-8 | 6.54 | 6.28 | 6.06 | 5.87 | 5.99 | 6.07 |
| At4g37650 | 253056_at | SHR | 7.40 | 7.05 | 7.47 | 6.30 | 6.38 | 6.06 |
| At5g14750 | 246585_at | WER | 8.26 | 9.05 | 8.34 | 7.51 | 7.10 | 7.61 |
| At5g19530 | 245947_at | ACL5 | 5.56 | 5.15 | 6.02 | 5.64 | 5.44 | 5.32 |
| At5g43700 | 249109_at | AUX2-11 | 7.60 | 8.29 | 7.47 | 7.16 | 7.18 | 7.17 |
| At5g43810 | 249115_at | PIN | 5.62 | 5.67 | 6.18 | 5.78 | 5.82 | 5.81 |
| At5g57090 | 247947_at | PIN2 | 10.60 | 10.68 | 10.82 | 9.97 | 10.32 | 10.04 |
| At5g59370 | 247736_at | ACTIN4 | 5.56 | 5.46 | 6.22 | 5.70 | 5.74 | 5.85 |
| At5g60920 | 247552_at | COB | 8.16 | 7.80 | 8.00 | 8.69 | 8.68 | 8.61 |

FIG. 5A

| EndoP CC | EndoP TC | EndoP TT | Peri CC | Peri TC | Peri TT | Stele CC | Stele TC | Stele TT |
|---|---|---|---|---|---|---|---|---|
| 8.40 | 7.93 | 7.65 | 8.62 | 8.53 | 7.96 | 8.14 | 7.12 | 6.64 |
| 7.99 | 7.75 | 7.84 | 7.73 | 7.26 | 7.77 | 7.97 | 7.51 | 8.19 |
| 7.55 | 7.30 | 7.13 | 6.64 | 6.48 | 7.65 | 7.89 | 7.38 | 8.36 |
| 6.72 | 6.57 | 6.29 | 6.66 | 6.21 | 7.19 | 7.83 | 7.20 | 7.99 |
| 6.72 | 6.57 | 6.29 | 6.66 | 6.21 | 7.19 | 7.83 | 7.20 | 7.99 |
| 7.27 | 7.18 | 6.87 | 5.47 | 7.66 | 7.86 | 7.35 | 6.61 | 6.09 |
| 8.56 | 8.92 | 8.28 | 7.86 | 8.17 | 9.26 | 8.74 | 8.57 | 8.95 |
| 7.55 | 7.29 | 7.50 | 7.44 | 8.08 | 8.39 | 8.36 | 7.74 | 8.32 |
| 8.99 | 8.64 | 8.97 | 8.32 | 8.44 | 8.77 | 9.03 | 8.95 | 9.29 |
| 11.05 | 11.27 | 11.64 | 10.97 | 10.49 | 10.55 | 9.83 | 9.91 | 9.94 |
| 9.65 | 8.88 | 9.37 | 8.73 | 8.55 | 9.63 | 9.50 | 9.19 | 10.00 |
| 6.94 | 7.30 | 7.76 | 6.36 | 6.49 | 6.47 | 7.29 | 7.69 | 7.73 |
| 8.04 | 7.89 | 7.92 | 8.12 | 7.82 | 8.10 | 7.91 | 7.78 | 8.13 |
| 8.08 | 7.30 | 7.52 | 7.54 | 7.86 | 7.77 | 7.91 | 7.61 | 7.50 |
| 8.35 | 8.79 | 8.27 | 7.24 | 8.83 | 9.65 | 7.87 | 7.94 | 8.00 |
| 5.98 | 6.02 | 5.34 | 4.97 | 6.20 | 6.09 | 6.00 | 4.89 | 4.69 |
| 7.44 | 7.19 | 7.67 | 6.92 | 6.69 | 7.78 | 8.74 | 8.13 | 9.25 |
| 8.82 | 8.46 | 8.02 | 7.55 | 7.48 | 8.68 | 9.43 | 8.30 | 9.54 |
| 6.25 | 6.16 | 6.31 | 5.51 | 5.86 | 5.54 | 6.01 | 6.07 | 5.45 |
| 6.29 | 6.66 | 6.26 | 6.20 | 6.42 | 6.40 | 7.17 | 6.55 | 7.12 |
| 7.57 | 7.03 | 7.27 | 7.40 | 6.89 | 7.24 | 7.89 | 7.55 | 8.02 |
| 7.33 | 7.32 | 7.00 | 6.72 | 6.72 | 8.18 | 9.01 | 7.98 | 9.23 |
| 7.93 | 7.37 | 7.89 | 8.82 | 9.26 | 8.83 | 7.83 | 8.21 | 7.65 |
| 5.96 | 6.05 | 5.69 | 8.52 | 5.80 | 5.49 | 5.55 | 5.70 | 5.62 |
| 7.68 | 7.98 | 7.93 | 8.48 | 8.52 | 8.21 | 7.73 | 7.68 | 7.71 |

FIG. 5B

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: oligos designed to detect the BAR gene

<400> SEQUENCE: 1
tcagttccaa acgtaaaacg g                                              21

<210> SEQ ID NO 2
<211> LENGTH: 19
<212> TYPE: DNA
<213> ORGANISM: Artificial Sequence
<220> FEATURE:
<223> OTHER INFORMATION: oligos designed to detect the BAR gene

<400> SEQUENCE: 2
cgtaccgagc cgcaggaac                                                 19

<210> SEQ ID NO 3
<211> LENGTH: 20
```

```
<212> TYPE: DNA
<213> ORGANISM: Artificial Sequence
<220> FEATURE:
<223> OTHER INFORMATION: oligos designed against the miR167a precursor
      for quantification of its expression (miR167aF)

<400> SEQUENCE: 3
tcagatgccg gtgcaccata                                              20

<210> SEQ ID NO 4
<211> LENGTH: 24
<212> TYPE: DNA
<213> ORGANISM: Artificial Sequence
<220> FEATURE:
<223> OTHER INFORMATION: oligos designed against the miR167a precursor
      for quantification of its expression (miR167aR)

<400> SEQUENCE: 4
caccaagttt cgagtagacc gtga                                         24

<210> SEQ ID NO 5
<211> LENGTH: 17
<212> TYPE: DNA
<213> ORGANISM: Artificial Sequence
<220> FEATURE:
<223> OTHER INFORMATION: oligos designed against the miR160a precursor
      for quantification of its expression (miR160aF)

<400> SEQUENCE: 5
gtatgcctgg ctccctg                                                 17

<210> SEQ ID NO 6
<211> LENGTH: 16
<212> TYPE: DNA
<213> ORGANISM: Artificial Sequence
<220> FEATURE:
<223> OTHER INFORMATION: oligos designed against the miR160a precursor
      for quantification of its expression (miR160aR)

<400> SEQUENCE: 6
tcgatgacct ccgtgg                                                  16
```

PERICYCLE-SPECIFIC EXPRESSION OF MICRORNA167 IN PLANTS

This application is a continuation of U.S. application Ser. No. 12/077,294 filed Mar. 17, 2008, now U.S. Pat. No. 8,624,084, which claims the benefit of U.S. Provisional Application No. 60/918,443 filed Mar. 16, 2007, the disclosures of each of which are incorporated by reference herein in their entireties.

This invention was made in part with government support under Grant numbers NIH NIGMS Grant GM3287; NSF *Arabidopsis* 2010 Genome Grant IBN0115586; and NSF Database Activities DBI-0445666. The government has certain rights in the invention.

1. INTRODUCTION

Provided herein are compositions and methods for modulating nucleotide sequence expression, particularly for modulating gene expression in plants. In some embodiments, provided herein are compositions and methods for genetically engineering plants to increase microRNA expression in a specific tissue, such as in roots. In certain specific embodiments, a plant or tree is genetically engineered to alter (e.g., increase) or constitutively express microRNA167 (also called "miR167" herein) in pericycle cells of the plant. In the presence of nitrogen, such genetically engineered plants can have one or more of the following characteristics as compared to the wild-type counterpart: enhanced lateral root growth, enhanced surface area of roots, increased root mass and/or increasing metabolic efficiency and nutrient uptake. Such genetically engineered plants can also, for example, grow larger, more efficiently or rapidly, and/or have increased biomass. The genetically engineered plants can also have, in the presence of nitrogen, enhanced uptake of minerals or heavy metals in contaminated soils. The engineered plants can be productively cultivated and increase lateral root growth under conditions of nitrogen fertilizer input or in nitrogen rich soils. Alternatively, the engineered plants may be used to achieve faster growing or maturing crops or, higher crop yields and/or more nutritious products even in nitrogen-rich cultivation conditions. In certain embodiments, the engineered plants and methods thereof are used in the production of commercial products. Some non-limiting example include genetically engineered trees for e.g., the production of pulp, paper, paper products or lumber; tobacco, e.g., for the production of cigarettes, cigars, or chewing tobacco; crops, e.g., for the production of fruits, vegetables and other food, including grains, e.g., for the production of wheat, bread, flour, rice, corn; and soybean, canola, e.g., for the production of oils.

2. BACKGROUND

Plants exhibit remarkable developmental plasticity in response to changing environments. This post-embryonic reorganization requires transcriptional reprogramming at the cell-specific level to initiate new organs to explore the soil for nutrients (see, e.g., Himanen et al., 2004, Proc Natl Acad Sci USA 101, 5146-51). Previous studies have shown distinct differences in the transcriptomes of *Arabidopsis thaliana* root cells in steady state culture conditions (Birnbaum et al., 2003, Science 302, 1956-60). However, little is known about the extent to which plants modulate gene expression at the cell specific level in response to changing nutrient conditions.

Nitrate is a key required nutrient for the synthesis of amino acids, nucleotides and vitamins and is commonly considered to be the most limiting for normal plant growth (Vitousek et al., 1991, Biogeochemistry 13:87-115). Nitrogenous fertilizer is usually supplied as ammonium nitrate, potassium nitrate, or urea. Plants are keenly sensitive to nitrogen levels in the soil and, atypically of animal development, adopt their body plan to cope with their environment (Lopez-Bucio et al., 2003, Curr Opin Plant Biol 6, 280-7); Malamy et al., 2005, Plant Cell Environ 28, 67-77); Walch-Liu et al., 2006, Ann Bot (Lond) 97, 875-81). For example, mutants in several general nitrogen (N)-assimilation genes affect root architecture (Little et al., 2005, Proc Natl Acad Sci USA 102, 13693-8; Remans et al., 2006, Proc Natl Acad Sci USA 103, 19206-11). Transduction of this nitrogen signal is linked to a massive and concerted gene expression response in the root (Gutierrez et al., 2007, Genome Biol 8, R7; Wang et al., 2003, Plant Physiol 132, 556-67).

Plant development is partially dependent on the plant's response to a variety of environmental signals. For example, the development of root systems is, in part, a response to the availability and distribution of moisture and nutrients within the soil.

In particular, lateral root development in *Arabidopsis* in response to nitrate is characterized by two distinct pathways. First, an increased rate of lateral root elongation is a localized, direct response to the presence of nitrate in the root zone. (Zhang et al., 1999, Proc Natl Acad Sci 96:6529-6534; Zhang and Forde, 2000, J of Exp. Bot. 51(342):51-59). In this aspect the nitrate ion appears to function as a signal rather than as a nutrient. (Zhang and Forde, 1998, Science 279:407-409). Second, accumulation of high concentrations of nitrate and other nitrogen compounds in the shoot is correlated with a inhibition of root growth through a systemic effect on lateral root meristem activation. (Zhang et al., 1999, supra).

Lateral root primordia formed on roots are the sites for lateral root emergence. Nitrogen treatments of wild-type plants affects (e.g., represses) the emergence of lateral roots. In wild-type plants, a large proportion of root primordia emerge into lateral roots only in nitrogen-poor conditions.

However, it would be advantageous to produce plants that would continue to increase lateral root growth, even in conditions of high nitrogen content in the environment. By increasing lateral root growth or emergence, as well as, for example, enhanced surface area of roots, and/or increased root mass, such plants would be able to assimilate more nitrogen and uptake other essential growth nutrients from the environment (e.g., soil or water) that would otherwise be taken up at much lower rate. Thus, a need remains for plants whose lateral root growth is insensitive to nitrogen content in its environment.

3. SUMMARY

A nitrogen-inducible gene in *Arabidopsis*, miR167, expressed preferentially in roots, acts to specifically degrade the mRNA made from other nitrogen-responsive regulatory genes responsible for the repression of lateral root development in the presence of nitrogen. Overexprssion of miR167 in the root meristem causes altered plant sensitivity to nitrate, and lateral root proliferation in nitrogen poor zones is increased. For example, miR167 overexpressing plants display an enhanced ratio of lateral root emergence in both nitrogen sufficient and nitrogen deplete conditions. These results indicate that miR167 is a key regulator of developmental plasticity in *Arabidopsis* roots. Thus, the miR167 gene product is likely a component of the regulatory pathway linking external nitrogen availability to decreased lateral root proliferation and Glu/Gln (the products of nitrate assmilation regulate levels of miR167). While overexpression of miR167 in a plant increases the ratio of emerging: initating lateral roots, reduced overall levels of lateral roots are seen and plants are rendered sterile. Thus, overexpression of miR167 in only particular cells (e.g., pericycle cells) can overcome these effects while maintaining high levels of lateral root emergence. The overexpression of miRNA167 in pericycle cells also results in the downregulation of the genes listed in Table I, infra.

Manipulation of a nitrogen responsive molecule, such as miR167 in agronomic crops could be of value in maximizing plant utilization in the presence of available nitrogen and in reducing agricultural nitrogen inputs, thereby providing economic and environmental benefits. Another benefit would be the ability of the engineered plants to be productively cultivated in both the presence and absence of nitrogen, such as following nitrogen fertilization or in nitrogen-rich soil. Improved control of lateral root proliferation could have useful applications in soil remediation and in prevention of soil erosion. Increased root biomass may be beneficial in production of specific structural carbohydrates in the roots themselves, or in improving plant output of specialty compounds, including plastics, proteins, secondary metabolites, and the like. Manipulation of nitrogen-responsive genes by modulating miR167 levels could also be useful in stimulating root proliferation of cuttings taken for plant propagation, especially in ornamental and woody species. Additional improvements include more vigorous (i.e., faster) growth as well as greater vegetative and/or reproductive yield under normal cultivation conditions (i.e., non-limiting nutrient conditions). To achieve these same improvements, traditional crop breeding methods would require screening large segregating populations. The present invention circumvents the need for such large scale screening by producing plants many of which, if not most, would have the desired characteristics.

We have discovered that miR167 levels are regulated by nitrogen nutrient treatment and are a regulatory point for the control of lateral root formation in plants, which is a key mechanism for plants to increase their surface area in the soil, to enhance nutrient acquisition. Based, in part, on this discovery, provided herein are compositions and methods of manipulating miR167 expression in transgenic plants to optimize lateral root growth and/or nutrient acquisition in the soil without the need for low nitrogen levels.

Compositions and methods are provided for modulating nucleotide sequence expression, particularly for modulating gene expression in plants. The compositions comprise precursor RNA constructs for the expression of an RNA precursor, such as miR167 precursor. In certain embodiments, a precursor RNA construct comprises a promoter, such as a tissue specific promoter, which is expressed in a plant cell, such as a pericycle cell, and promotes the expression of a precursor RNA having a miRNA, such as miR167. The RNA precursor is cleaved in the plant cell to form an miR167, which is a regulatory RNA that specifically controls gene expression of certain target genes, which may, in turn, regulate a variety of other genes of the plant. The miR167 can be fully or partially complementary to a portion of the nucleotide sequence encoding a target gene mRNA (e.g., ARF8) and functions to modulate expression of the target sequence or gene.

In certain embodiments, a precursor RNA construct is used in combination with a modulator to enhance the effect on gene expression. Modulators are proteins which can alter the level of at least one miRNA, such as miR167, in a plant cell.

Any of a variety of promoters can be utilized in the constructs of the invention depending on the desired outcome. Tissue-specific or tissue-preferred promoters, inducible promoters, developmental promoters, constitutive promoters and/or chimeric promoters can be used to direct expression of the miRNA sequence or the modulator sequence in specific cells or organs the plant, when fused to the appropriate cell or organ specific promoter.

Chimeric constructs expressing miR167 in transgenic plants (using constitutive or inducible promoters) can be used in the compositions and methods provided herein to enhance lateral root formation, which in turn increase nutrient uptake from soil. The use of inducible promoters can "prime" a plant to produce additional lateral roots for nutrient acquisition from the soil, for example, prior to fertilizer application. As minerals and nutrients rapidly leach out of soil, optimizing root architecture to coincide with nutrient applications can enhance nutrient capture from soil. This is especially true for negatively charged minerals which bind poorly to negatively charged soil particles.

The discovery that miR167 regulates lateral root formation in response to nitrogen treatment was only made possible by the use of cell-specific transcript profiling as described in the examples herein. In certain embodiments, pericycle-specific promoters are used in the compositions and methods provided herein to specifically express miR167.

In those embodiments, the overexpression of miR167 specifically in the pericycle can serve to increase the number of lateral roots, increasing the surface area of roots, and make the root mass much more dense. This increased root mass can enhance uptake of nitrogen and other nutrients and water from the soil. The manipulation of miR167 levels in transgenic plants thus acts as a tool to increase metabolic efficiency in plants and allows plants to better use smaller amounts of nitrogen and other mineral nutrients from the soil, reducing the quantities needed in fertilizers, or show enhanced growth in the presence of normal or high levels of nitrogen.

The present invention is based, in part, on the finding that miR167 levels are regulated by nitrogen and are a regulatory point for the control of lateral root formation in plants, and that increased or constitutive miR167 expression in root-specific cells, such as the pericycle, results in enhanced lateral root growth, enhanced surface area of roots, increased root mass and/or increasing metabolic efficiency. The invention is illustrated herein by the way of a working example in which we used previously constructed *Arabidopsis* (model plant system) that had been engineered with recombinant constructs encoding a strong, constitutive plant promoter, the cauliflower mosaic virus (CaMV) 35S promoter, operably linked with sequences encoding a miR167. RNA and protein analyses showed that a majority of the engineered plants exhibited ectopic, overexpression of miR167 (Wu et al., 2006, Development 133, 4211-8). The miR167 overexpressing transgenic lines have a higher proportion of lateral root emergence and growth in the presence of a nitrogen-rich environment than the control, wild-type plant.

Alternatively, transgenic plants can include those plants that have been genetically engineered to alter the expression of one or more or all of the genes listed in Table I, independent of miRNA167. In an alternative embodiment, the present invention is directed to a transgentic plant in which one or more of the miRNA167-responsive genes listed in Table 1 is down-regulated and which plant displays an enhanced ratio of lateral root emergence in both nitrogen sufficient and nitrogen depleted conditions. Such a transgenic plant has one or more agronomic or nutritional characterisitic including increased lateral root formation, increased surface area of roots, increased root mass, increased metabolic efficiency, increased nutrient uptake, faster growth rate, and/or greater fruit or seed yield (compared to the corresponding non-transgenic plant. In a specific aspect, a transgenic plant of the invention is one which has been genetically engineered such that one or more, or all of the miRNA167-responsive genes listed in Table 1 have been downregulated. In one specific aspect of this embodiment, a transgenic plant of the invention is one which has been genetically engineered such that one or more, or all of the miRNA167-responsive transcription factors and/or DNA binding proteins listed in Table 1 are down-regulated, resulting in the desired agronomic and/or nutritional characteristic.

4. TERMINOLOGY

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

As used herein, the term "agronomic" includes, but is not limited to, changes in root size, vegetative yield, seed yield or overall plant growth. Other agronomic properties include factors desirable to agricultural production and business.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., 1993, American Society for Microbiology, Washington, D.C. The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

In its broadest sense, a "delivery system," as used herein, is any vehicle capable of facilitating delivery of a nucleic acid (or nucleic acid complex) to a cell and/or uptake of the nucleic acid by the cell.

The term "ectopic" is used herein to mean abnormal subcellular (e.g., switch between organellar and cytosolic localization), cell-type, tissue-type and/or developmental or temporal expression (e.g., lightdark) patterns for the particular gene or enzyme in question. Such ectopic expression does not necessarily exclude expression in tissues or developmental stages normal for said enzyme but rather entails expression in tissues or developmental stages not normal for the said enzyme.

By "endogenous nucleic acid sequence" and similar terms, it is intended that the sequences are natively present in the recipient plant genome and not substantially modified from its original form.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., 1989, Nucl. Acids Res. 17: 477-498). Thus, the maize preferred codon for a particular amino acid may be derived from known gene sequences from maize. Maize codon usage for 28 genes from maize plants is listed in Table 4 of Murray et al., supra.

By "fragment" is intended a portion of the nucleotide sequence. Fragments of the modulator sequence will generally retain the biological activity of the native suppressor protein. Alternatively, fragments of the targeting sequence may or may not retain biological activity. Such targeting sequences may be useful as hybridization probes, as antisense constructs, or as co-suppression sequences. Thus, fragments of a nucleotide sequence may range from at least about 20 nucleotides, about 50 nucleotides, about 100 nucleotides, and up to the full-length nucleotide sequence of the invention.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., Plant Molecular Biology: A Laboratory Manual, Clark, Ed., 1997, Springer-Verlag, Berlin. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end Consensus sequences at the 3' end, such as polyadenylation sequences, aid in determining whether the polynucleotide has a complete 3' end.

The term "gene activity" refers to one or more steps involved in gene expression, including transcription, translation, and the functioning of the protein encoded by the gene.

The term "genetic modification" as used herein refers to the introduction of one or more exogenous nucleic acid sequences, e.g., miR167 encoding sequences, as well as regulatory sequences, into one or more plant cells, which can generate whole, sexually competent, viable plants. The term "genetically modified" or "genetically engineered" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, plant, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. See, e.g., Compounds and Methods for Site Directed Mutagenesis in Eukaryotic Cells, Kmiec, U.S. Pat. No. 5,565,350; In vivo Homologous Sequence Targeting in Eukaryotic Cells; Zarling et al., PCT/US93/03868. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

As used herein, the term "marker" refers to a gene encoding a trait or a phenotype which permits the selection of, or the screening for, a plant or plant cell containing the marker.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., 1989, Molecular Cloning—A Laboratory Manual, 2nd ed., Vol. 1-3; and Current Protocols in Molecular Biology, F. M. Ausubel et al., Eds., 1994, Current Protocols, a joint venture between Greene Publishing Associates, Inc. and John Wiley & Sons, Inc.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Be term "orthologous" as used herein describes a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

The term "overexpression" is used herein to mean above the normal expression level in the particular tissue, all and/or developmental or temporal stage for said enzyme.

As used herein, the term "plant" is used in its broadest sense, including, but not limited to, any species of woody, ornamental or decorative, crop or cereal, fruit or vegetable plant, and algae (e.g., *Chlamydomonas reinhardtii*). Non-limiting examples of plants include plants from the genus *Arabidopsis* or the genus *Oryza*. Other examples include plants from the genuses *Acorus, Aegilops, Allium, Ambo-rella, Antirrhinum, Apium, Arachis, Beta, Betula, Brassica, Capsicum, Ceratopteris, Citrus, Cryptomeria, Cycas, Des-curainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Per-sea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia.*" Plants included in the invention are any plants amenable to transformation techniques, including gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiospeiliis include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, *sequoia*, cedar, oak, etc. Still other examples of plants include, but are not limited to, wheat, cauliflower, tomato, tobacco, corn, petunia, trees, etc. As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce. As used herein, the term "plant" also refers to either a whole plant, a plant part, or organs (e.g., leaves, stems, roots, etc.), a plant cell, or a group of plant cells, such as plant tissue, plant seeds and progeny of same. Plantlets are also included within the meaning of "plant." The class of plants which can be used in the methods of the invention is generally as broad as the class of higher plants amenable to transformation techniques, including both monocotyledonous and dicotyledonous plants.

The term "plant cell" as used herein refers to protoplasts, gamete producing cells, and cells which regenerate into whole plants. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as naturally occurring nucleotides and/ or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically-, enzymatically- or metabolically-modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally-occurring amino acid, as well as to naturally-occurring amino acid polymers. The essential nature of such analogues of naturally-occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred." Promoters which initiate transcription only in certain tissue are referred to as "tissue specific." A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters represent the class of "non-constitutive" promoters. A "constitutive" promoter is a promoter which is active under most environmental conditions.

As used herein "recombinant" includes reference to a cell or vector that has been modified by the introduction of a heterologous nucleic acid, or to a cell derived from a cell so modified. Thus, for example, recombinant cells express genes that are not found in identical form within the native (non-recombinant) form of the cell, or exhibit altered expression of native genes, as a result of deliberate human intervention. The term "recombinant" as used herein does not encompass the alteration of the cell or vector by events (e.g., spontaneous mutation, natural transformation, transduction, or transposition occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "regulatory sequence" as used herein refers to a nucleic acid sequence capable of controlling the transcription of an operably associated gene. Therefore, placing a gene under the regulatory control of a promoter or a regulatory element means positioning the gene such that the expression of the gene is controlled by the regulatory sequence(s). Because a microRNA binds to its target, it is a post transcriptional mechanism for regulating levels of mRNA. Thus, an miRNA, e.g., miR167, can also be considered a "regulatory sequence" herein. Not just transcription factors.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "root-specific promotor" is a polynucleotide encoding a promoter that specifically binds to transcription factors primarily or only in roots.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

As used herein, a "stem-loop motif" or a "stem-loop structure," sometimes also referred to as a "hairpin structure," is given its ordinary meaning in the art, i.e., in reference to a single nucleic acid molecule having a secondary structure that includes a double-stranded region (a "stem" portion) composed of two regions of nucleotides (of the same molecule) forming either side of the double-stranded portion, and at least one "loop" region, comprising uncomplemented nucleotides (i.e., a single-stranded region).

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, 1984, Anal. Biochem., 138:267-284: $T_m$-81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York; and Current Protocols in Molecular Biology, Chapter 2, Ausubel et al., Eds., 1995, Greene Publishing and Wiley- Interscience, New York. Hybridization and/or wash conditions can be applied for at least 10, 30, 60, 90, 120, or 240 minutes.

As used herein, "transcription factor" includes reference to a protein which interacts with a DNA regulatory element to affect expression of a structural gene or expression of a second regulatory gene. "Transcription factor" may also refer to the DNA encoding said transcription factor protein. The function of a transcription factor may include activation or repression of transcription initiation.

The term "transfection," as used herein, refers to the introduction of a nucleic acid into a cell, for example, a precursor miRNA, or a nucleotide sequence able to be transcribed to produce precursor miRNA.

As used herein, the term "transformation" means alteration of the genotype of a host plant by the introduction of miR167-nucleic acid sequence.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, 1981, Adv. Appl. Math. 2: 482; by the homology alignment algorithm of Needleman and Wunsch, 1970, J. Mol. Biol. 48: 443; by the search for similarity method of Pearson and Lipman, 1988, Proc. Natl. Acad. Sci. 85: 2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, 1988, Gene 73: 237-244; Higgins and Sharp, 1989, CABIOS 5: 151-153; Corpet et al., 1988, Nucleic Acids Research 16: 10881-90; Huang et al., 1992, Computer Applications in the Biosciences 8: 155-65; and Pearson et al., 1994, Methods in Molecular Biology 24: 307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel et al., Eds., 1995, Greene Publishing and Wiley-Interscience, New York.

Software for performing BLAST analyses is publicly available, e.g., through the National Center for Biotechnology Information (world-wide web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, Proc. Natl. Acad. Sci. USA 89:10915).

In addition to calculating percent sequence identity, the BLAST algorithm also performs a statistical analysis of the similarity between two sequences (see, e.g., Karlin & Altschul, 1993, Proc. Natl. Acad. Sci. USA 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, 1993, Comput. Chem., 17:149-163) and XNU (Claverie and States, 1993, Comput. Chem., 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff, 1989, Proc. Natl. Acad. Sci. USA 89:10915).

Multiple alignment of the sequences can be performed using the CLUSTAL method of alignment (Higgins and Sharp, 1989, CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, 1988, Computer Applic. Biol. Sci., 4:11-17, e.g., as implemented in the program PC/GENE (Intelligenetics, Mountain View, Calif., USA).

Polynucleotide sequences having "substantial identity" are those sequences having at least about 50%, 60% sequence identity, generally 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequences generally means sequence identity of at least 50%, more preferably at least 70%, 80%, 90%, and most preferably at least 95%. Nucleotide sequences are generally substantially identical if the two molecules hybridize to each other under stringent conditions.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "transgenic," when used in reference to a plant (i.e., a "transgenic plant") refers to a plant that contains at least one heterologous gene in one or more of its cells.

As used herein, "substantially complementary," in reference to nucleic acids, refers to sequences of nucleotides (which may be on the same nucleic acid molecule or on different molecules) that are sufficiently complementary to be able to interact with each other in a predictable fashion, for example, producing a generally predictable secondary structure, such as a stem-loop motif. In some cases, two sequences of nucleotides that are substantially complementary may be at least about 75% complementary to each other, and in some cases, are at least about 80%, at least about 85%, at least about 90%, at least about 95%, at least about 96%, at least about 97%, at least about 98%, at least about 99%, at least about 99.5%, or 100% complementary to each other. In some cases, two molecules that are sufficiently complementary may have a maximum of 40 mismatches (e.g., where one base of the nucleic acid sequence does not have a complementary partner on the other nucleic acid sequence, for example, due to additions, deletions, substitutions, bulges, etc.), and in other cases, the two molecules may have a maximum of 30 mismatches, 20 mismatches, 10 mismatches, or 7 mismatches. In still other cases, the two sufficiently complementary nucleic acid sequences may have a maximum of 0, 1, 2, 3, 4, 5, or 6 mismatches.

By "variants" is intended substantially similar sequences. For "variant" nucleotide sequences, conservative variants include those sequences that, because of the degeneracy of the genetic code, encode the amino acid sequence of the modulator of the invention. Variant nucleotide sequences include synthetically derived sequences, such as those generated, for example, using site-directed mutagenesis. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. By "variant" protein is intended a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function As used herein, the term "yield" or "plant yield" refers to increased plant growth, and/or increased biomass. In one embodiment, increased yield results from increased growth rate and increased root size. In another embodiment, increased yield is derived from shoot growth. In still another embodiment, increased yield is derived from fruit growth.

5. DESCRIPTION OF THE FIGURES

FIGS. 1A-E shows that the N-response is highly cell specific. (A) N-response clusters. The number of genes within each cluster is indicated using the length of the adjacent bar. Clusters that exhibit some degree of Glu/Gln-responsiveness are indicated with hatching on the bars. These were determined by their partial loss of N-responsiveness on addition of MSX and the regaining of this on Glu/Gln resupply. (B) Average log 2 microarray expression values for the three largest gene response clusters in control and treated experiments. Top panel: gene cluster that is N-induced in all cell populations contains an over-representation of GO terms relating to control of metabolism. Middle panel: gene cluster that is N-induced in the lateral root cap and pericycle contains an over-representation of the GO term 'regulation of transcription'. Bottom panel: gene cluster that is N-repressed in the epidermis and stele contains an over-representation of the GO term 'photosynthesis.' (C) Schematic of the Arabidopsis root showing the five cell populations studied: red, LRC; dark blue/light blue, epidermis/cortex; orange, endodermis; green, pericycle; green/yellow, stele (pericycle and vascular tissues). The direction of nitrate uptake and its assimilation into amino acids (aa) is indicated using arrows.

FIGS. 2A-B shows miR167 and ARF8 are N-regulated in an opposite and dependent fashion to modulate lateral root development. (A) Network of genes that are induced in the pericycle cell layer. (B) Zoom-in of this pericycle N-induced network to show a sub-network controlled by ARF8 and miR167. ARF6 (At1g30330) was not found to be significantly N-regulated in this study but is included in the network since its is a known partner of ARF8 (Wu et al., 2006, Development 133, 4211-8); ARF6 does appear to be N-regulated in a similar fashion to ARF8 when the raw microarray data is viewed thus it's inclusion is valid. ARF8 target genes include: Transcription factors (diamonds) or DNA-binding proteins (squares with circle pattern): (1a) At3g61310, (1b) At1g76420, (1c) At1g24260, (1d) At1g79350, (1e) At1g63470, (1f) At2g20100, (1g) At3g45610. LRR kinases (squares with circle pattern): (2a) At2g26330, (2b) At3g57830, (2c) At2g01210. Metabolic genes (black squares): (3a) At3g16170, (3b) At1g48100, (3c) At1g11730, (3d) At1g70710 (CEL1), (3e) At1g32930. Expressed proteins (squares with crisscross pattern): (4a) At3g13000, (4b) At2g38160, (4c) At1g03170, (4d) At3g13510, (4e) At2g23700, (4f) At3g11000. Other cellular function: (5) Kinesin motor protein-related At3g10310. (6) DNA polymerase delta small subunit-related At2g42120. (7) Cyclin A2;3 At1g15570. (8) Calmodulin-binding family protein At2g26180. (9) DNA primase At1g67320. (10) Emsy N terminus domain-containing protein ENT domain-containing protein At2g44440. In addition, At3g61310 and ARF6 (At1g30330) are also predicted miR167 targets (according to Dezulian et al., 2006, Bioinformatics 22, 359-60). White box denotes genes that are not specifically Glu-responsive.

Figure 3L:
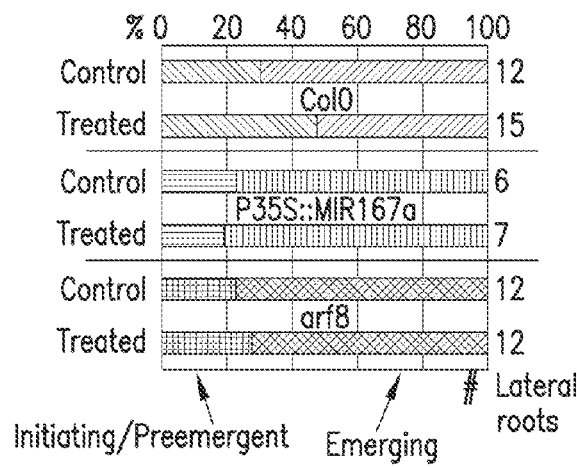
Figure 3M:
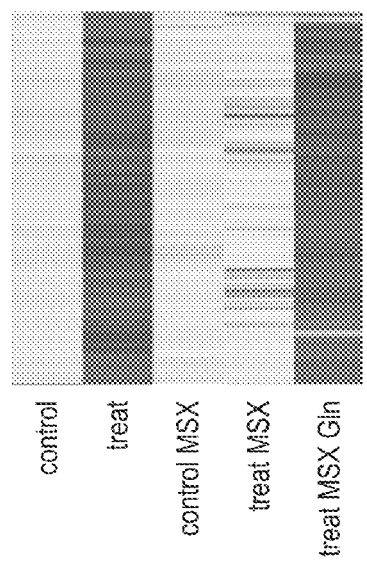
Figure 3N:
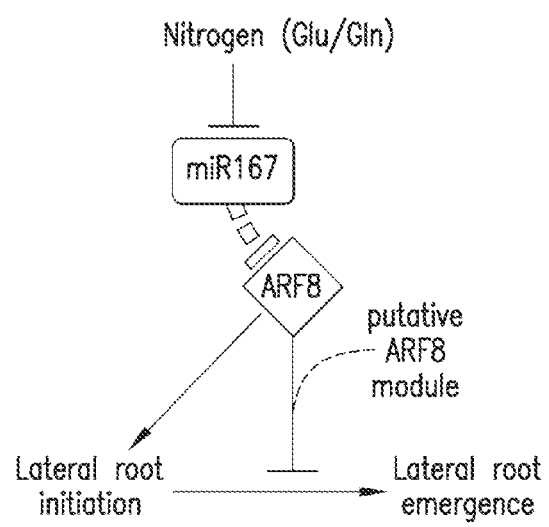

FIGS. 3A-N show antagonistic regulation between miRNA167 and ARF-8 in response to nitrogen mediates lateral root initiation and emergence. A, D, G, GUS-stained control roots. B, E, H, GUS-stained nitrate-treated roots; all roots were GUS-stained for 12 hours. C, F, I, Average expression level of indicated genes and constructs assessed by qPCR in whole roots control-treated (C) or nitrate-treated (T) from 3 biological replicates. A-C, Nitrogen-induction of gARF8:GUS and qPCR quantification of ARF8 expression. D-F, Nitrogen-repression of PMIR167a::GUS and qPCR quantification of pre-miR167a expression. A control microRNA (miR160) showed no nitrogen response. G-I, Loss of nitrogen induction of ARF8 expression in mARF8:GUS and qPCR quantification of GUS expression. J, Response of mature miR167a/b to nitrogen treatment in the five cell populations profiled. K, Confocal images of initiating and pre-emergent lateral roots (GFP-marked) and emerging lateral roots (not GFP-marked) in the line used for cell sorting that marks pericycle cells adjacent to the xylem pole (E3754). L, Bar graphs show the relative mean percentages of initiating (light colored bars) and emerging (dark colored bars) lateral roots in Col-0, arf8, and P358::MIR167a four days after 12 day-old seedlings were either mock-treated (no treatment) or nitrate-treated. To the right of the bars, the average number of lateral roots per seedling is shown. The P35S::MIR167a has fewer lateral roots in total as a consequence of having shorter roots. Col0 (n=21), arf8-3 (n=11), and 35S::miR167a (n=6) 4 days after 12 day-old seedlings were either control-treated (no treatment) or N-treated. Col0 (top two bars) control-treatment 32%±3 initiating, 68%±3 emerging; N-treatment 48±3 initiating, 52±3 emerging. 35S::miR167a (middle two bars) control-treatment 23%±3 initiating, 77%±7 emerging; N-treatment 19%±4 initiating, 81%±9 emerging. arf8 (bottom two bars) control-treatment 23%±3 initiating, 77%±4 emerging; N-treatment 34±3 initiating, 66±4 emerging. On the right of the bars the average number of lateral roots per seedling is shown. 35S::miR167-expressing seedlings have fewer lateral roots in total at the same time as having a higher percentage of emerging lateral roots. 35S::miR167-expressing seedlings are insensitive to nitrogen-downregulation of lateral root emergence. 35S::miR167-expressing seedlings also exhibit fewer lateral roots overall. arf8 seedlings have a reduced N-sensitivity. We used a chi-squared test to compare the wild-type ratio of initiating:emerging lateral roots with the ratios that we observed in 35S::miR167 and arf8. M, Heat map showing the response (blue=induction, yellow=repression) of ARF8 and the 126 predicted target genes in the putative ARF8 module to KNO3, KCl, MSX and Gln treatments in sorted pericycle founder cells. N, Summary of the miR167ARF8-regulated genetic circuitry that controls the balance between initiating and emerging lateral roots in relation to nitrogen availability. Scale bars: 25 µm.

FIG. 4 depicts ARF8 cluster genes

FIGS. 5A-B depicts signal values for the 25 cell-specific genes

Figure 6A:
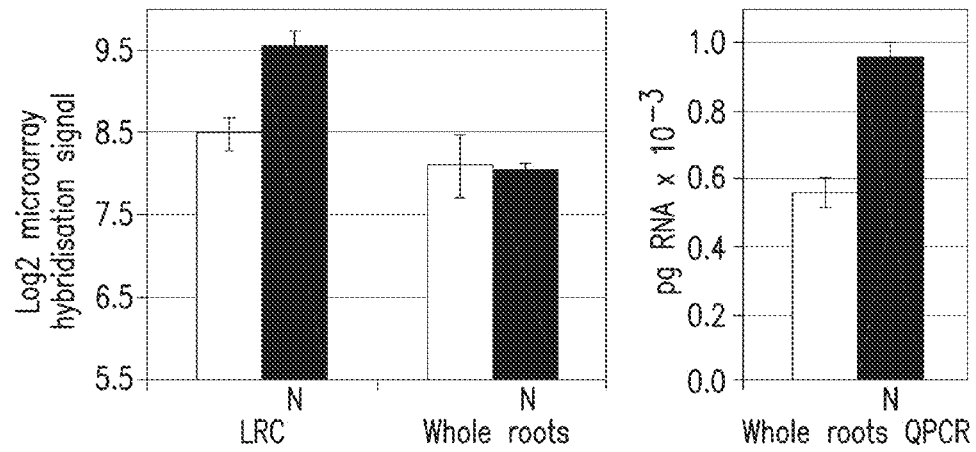
Figure 6B:
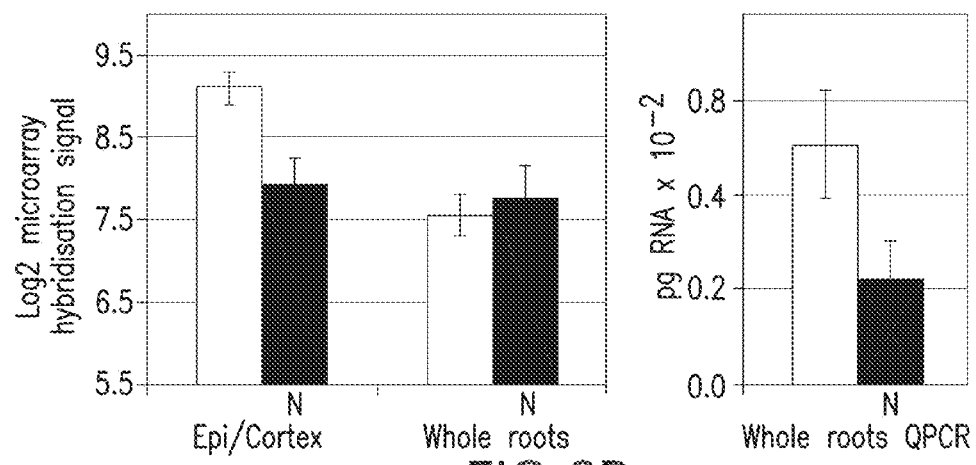
Figure 6C:
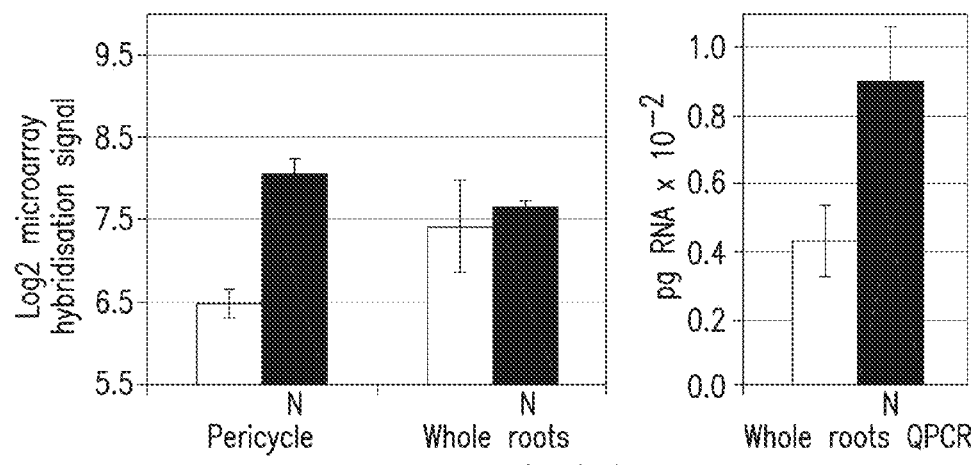
Figure 7A:
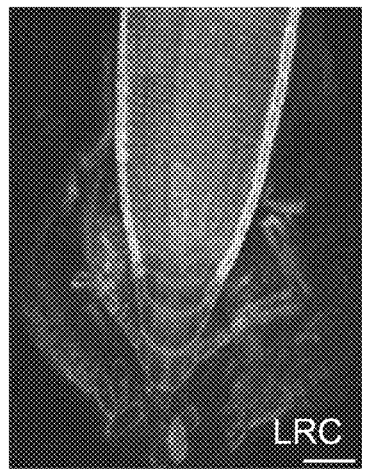
Figure 7B:
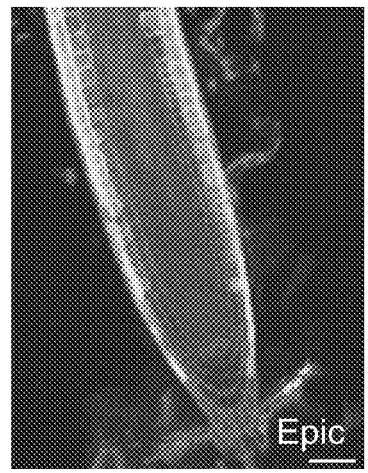
Figure 7C:
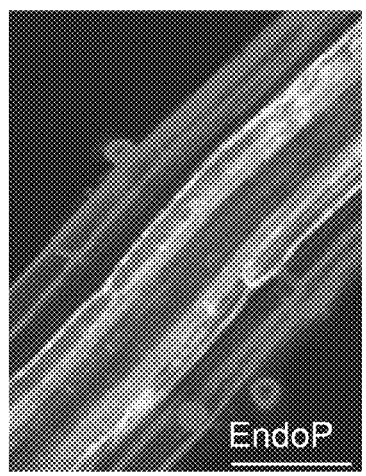
Figure 7D:
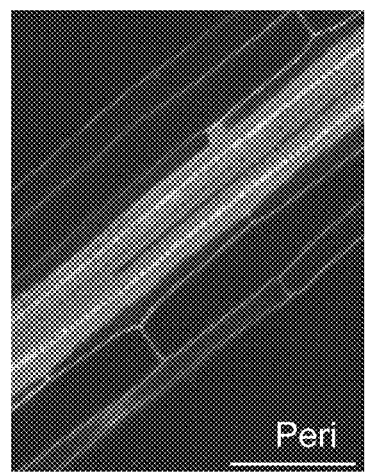

FIG. 6A-C shows that cell sorting enhances sensitivity to discover N-regulation of genes. qPCR confirms the N-response found in individual cell populations using microarrays that was not found at the whole root level. (A) At5g03280 is induced in the LRC cell population. (B) At5g22300 is depressed in the epidermiscortex cell population. (C) At3g61310 is induced in the pericycle cell population. n=3 biological replicates.

FIGS. 7A-D depicts the expression patterns of four of the five GFP marker lines used in this study. (A) E4722 marks the lateral root cap; (B) E1001 marks the epidermis and cortex; (C) E470 is expressed in the endodermis and pericycle; (D) E3754 marks the pericycle. The fifth line used, pWOL::GFP, is expressed specifically in the stele from the promeristem to the early differentiation stages (published in [20]). Scale bars: 25 µm.

6. DETAILED DESCRIPTION

A nitrogen-inducible gene in *Arabidopsis*, miR167, expressed preferentially in roots, acts to specifically degrade the mRNA made from other nitrogen-responsive regulatory genes responsible for the repression of lateral root development in the presence of nitrogen. Overexprssion of miR167 in the root meristem causes altered plant sensitivity to nitrate, and lateral root proliferation in nitrogen poor zones is increased. For example, miR167 overexpressing plants display an enhanced ratio of lateral root emergence in both nitrogen sufficient and nitrogen deplete conditions. These results indicate that miR167 is a key regulator of developmental plasticity in *Arabidopsis* roots. Thus, the miR167 gene product is likely a component of the regulatory pathway linking external nitrogen availability to decreased lateral root proliferation and Glu/Gln (the products of nitrate assmilation regulate levels of miR167). While overexpression of miR167 in a plant increases the ratio of emerging: initating lateral roots, reduced overall levels of lateral roots are seen and plants are rendered sterile. Thus, overexpression of miR167 in only particular cells (e.g., pericycle cells) can overcome these effects while maintaining high levels of lateral root emergence.

Manipulation of a nitrogen responsive molecule, such as miR167 in agronomic crops could be of value in maximizing plant utilization in the presence of available nitrogen and in reducing agricultural nitrogen inputs, thereby providing economic and environmental benefits. Another benefit would be the ability of the engineered plants to be productively cultivated in both the presence and absence of nitrogen, such as following nitrogen fertilization or in nitrogen-rich soil. Improved control of lateral root proliferation could have useful applications in soil remediation and in prevention of soil erosion. Increased root biomass may be beneficial in production of specific structural carbohydrates in the roots themselves, or in improving plant output of specialty compounds, including plastics, proteins, secondary metabolites, and the like. Manipulation of nitrogen-responsive genes by modulating miR167 levels could also be useful in stimulating root proliferation of cuttings taken for plant propagation, especially in ornamental and woody species. Additional improvements include more vigorous (i.e., faster) growth as well as greater vegetative and/or reproductive yield under normal cultivation conditions (i.e., non-limiting nutrient conditions). To achieve these same improvements, traditional crop breeding methods would require screening large segregating populations. The present invention circumvents the need for such large scale screening by producing plants many of which, if not most, would have the desired characteristics.

We have discovered that miR167 levels are regulated by nitrogen nutrient treatment and are a regulatory point for the control of lateral root formation in plants, which is a key mechanism for plants to increase their surface area in the soil, to enhance nutrient acquisition. Based, in part, on this discovery, provided herein are compositions and methods of manipulating miR167 expression in transgenic plants to optimize lateral root growth and/or nutrient acquisition in the soil without the need for low nitrogen levels.

Compositions and methods are provided for modulating nucleotide sequence expression, particularly for modulating gene expression in plants. The compositions comprise precursor RNA constructs for the expression of an RNA precursor, such as miR167 precursor. In certain embodiments, a precursor RNA construct comprises a promoter, such as a tissue specific promoter, which is expressed in a plant cell, such as a pericycle cell, and promotes the expression of a precursor RNA having a miRNA, such as miR167. The RNA precursor is cleaved in the plant cell to form an miR167, which is a regulatory RNA that specifically controls gene expression of certain target genes, which may, in turn, regulate a variety of other genes of the plant. The miR167 can be fully or partially complementary to a portion of the nucleotide sequence encoding a target gene mRNA (e.g., ARF8) and functions to modulate expression of the target sequence or gene. Thus, an RNA precursor construct can be designed to modulate levels of any mRNA nucleotide sequence of interest, either an endogenous plant mRNA or alternatively a transgene mRNA. The RNA precursor can also be designed to produce a transcript that is processed via the miRNA pathway to produce an miRNA complementary to a portion of mRNA, the target mRNA, that corresponds to the target gene. The miRNA modulates the expression of the target gene, such as by altering the production, processing, stability, or translation of the target mRNA and thereby altering the expression of the target mRNA product.

In certain embodiments, a precursor RNA construct is used in combination with a modulator to enhance the effect on gene expression. Modulators are proteins which can alter the level of at least one miRNA, such as miR167, in a plant cell, including, but not limited to plant and viral proteins that are known to alter RNA silencing. Expression of a modulator in the presence of the precursor RNA alters the accumulation of miRNAs and thus enhances the regulatory capabilities of miRNAs. In this manner, a plant expressing both the precursor RNA and a modulator can be constructed to modulate expression of a target gene.

Any of a variety of promoters can be utilized in the constructs of the invention depending on the desired outcome. Tissue-specific or tissue-preferred promoters, inducible promoters, developmental promoters, constitutive promoters and/or chimeric promoters can be used to direct expression of the miRNA sequence or the modulator sequence in specific cells or organs the plant, when fused to the appropriate cell or organ specific promoter.

Chimeric constructs expressing miR167 in transgenic plants (using constitutive or inducible promoters) can be used in the compositions and methods provided herein to enhance lateral root formation, which in turn increase nutrient uptake from soil. The use of inducible promoters can "prime" a plant to produce additional lateral roots for nutrient acquisition from the soil, for example, prior to fertilizer application. As minerals and nutrients rapidly leach out of soil, optimizing root architecture to coincide with nutrient applications can enhance nutrient capture from soil. This is especially true for negatively charged minerals which bind poorly to negatively charged soil particles.

The discovery that miR167 regulates lateral root formation in response to nitrogen treatment was only made possible by the use of cell-specific transcript profiling as described in the examples herein. In certain embodiments, pericycle-specific promoters are used in the compositions and methods provided herein to specifically express miR167.

In those embodiments, the overexpression of miR167 specifically in the pericycle can serve to increase the number of lateral roots, increasing the surface area of roots, and make the root mass much more dense. This increased root mass can enhance uptake of nitrogen and other nutrients and water from the soil. The manipulation of miR167 levels in transgenic plants thus acts as a tool to increase metabolic efficiency in plants and allows plants to better use smaller amounts of nitrogen and other mineral nutrients from the soil, reducing the quantities needed in fertilizers, or show enhanced growth in the presence of normal or high levels of nitrogen.

Achieving the desired plant improvements may require, in some instances, the ectopic overexpression of a miR167 in specific organs or cell types, such as in pericycle cells of a plant. The modified expression may involve engineering the plant with any or several of the following: a) a transgene in which the coding sequence for the miRNA is operably associated to a strong, constitutive promoter; b) additional copies of the native gene encoding the desired miR167; c) regulatory gene(s) that activates the expression of miR167; d) a copy of the native miR167 gene that has its regulatory region modified for enhanced expression; and e) a transgene which expresses a mutated, altered or chimeric version of a miR167. In certain embodiments, the miR167 gene or transgene is under the control of a constitutive or inducible promoter, and in specific embodiments the promoter is a pericycle-specific promoter.

In other instances, achieving the desired plant improvements may require altering the expression pattern of a miR167. The altered expression pattern may involve engineering the plant with any or many of the following: a) a transgene in which the coding sequence for the miR167 is operably associated to a promoter with the desired expression pattern (such promoters may include those considered to have tissue (e.g., pericycle) or developmental-specific expression patterns); b) modified regulatory genes that activates the expression of the miR167-encoding gene in the preferred pattern; c) a native copy of the miR167-encoding gene that has its regulatory region modified to express in the preferred pattern. In certain embodiments, the miR167 gene is under the control of a constitutive or inducible promoter, and in specific embodiments the promoter is a pericycle-specific promoter.

In still other instances, achieving the desired plant improvements may require expressing altered or different forms of miR167. Such efforts may involve developing a plant-expressible gene encoding a miRNA 167 with properties different from those of the corresponding host plant miR167 and engineering plants with that gene construct. Gene sequences encoding such miR167 may be obtained from a variety of sources, including, but not limited to bacteria, yeast, algae, animals, and plants. In some cases, such coding sequences may be directly used in the construction of plant-expressible gene fusions by operably linking the sequence with a desired plant-active promoter. In other cases, the utilization of such coding sequences in gene fusions may require prior modification by in vitro mutagenesis or de novo synthesis to enhance their translatability in the host plant or to alter the properties of the miR167 encoded thereon. Useful alterations may include, but are not limited to, modifications of residues involved in target mRNA binding.

A plant with the desired improvement can be isolated by screening the engineered plants for altered expression pattern or level of the miR167 (or precursor thereof) and/or expression pattern or level of a direct or indirect target polynucleotide of the miR167, such as mRNA for ARF8, or downstream gene products whose expression is modulated by ARF8 (FIG. 2B), such as At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440. A plant can also be screened for lateral root growth, root surface area, root biomass, nutrient uptake, overall increased plant growth rate, enhanced vegetative yield, or improved reproductive yields. The screening of the engineered plants can involve Southern analysis to confirm the presence and number of transgene insertions, Northern analysis, RNase protection, primer extension, reverse transcriptase/PCR and the like to measure mRNA levels; measuring the amino acid composition, free amino acid pool or total nitrogen content of various plant tissues; monitoring numbers and types of lateral root primordia and lateral roots; measuring growth rates in terms of fresh weight gains over time; or measuring plant yield in terms of total dry weight and/or total seed weight, or a combination of any of the above methods.

The present invention is based, in part, on the finding that miR167 levels are regulated by nitrogen and are a regulatory point for the control of lateral root formation in plants, and that increased or constitutive miR167 expression in root-specific cells, such as the pericycle, results in enhanced lateral root growth, enhanced surface area of roots, increased root mass and/or increasing metabolic efficiency. The invention is illustrated herein by the way of a working example in which we used previously constructed *Arabidopsis* (model plant system) that had been engineered with recombinant constructs encoding a strong, constitutive plant promoter, the cauliflower mosaic virus (CaMV) 35S promoter, operably linked with sequences encoding a miR167. RNA and protein analyses showed that a majority of the engineered plants exhibited ectopic, overexpression of miR167 (Wu et al., 2006, Development 133, 4211-8). The miR167 overexpressing transgenic lines have a higher proportion of lateral root emergence and growth in the presence of a nitrogen-rich environment than the control, wild-type plant.

The present invention provides methods for increasing the yield of a plant, such as a agricultural crop, such as by increasing (e.g., by overexpressing and/or inducibly or constitutively expressing) miR167 expression levels in the root of a plant. Increasing miRNA expression level in plant root cells results in increased lateral root growth, root biomass, nutrient uptake, overall plant growth and yield, even in the presence of nitrogen.

In a preferred embodiment, the invention provides a method for producing a genetically modified plant characterized as having increased lateral root growth, root biomass, nutrient uptake, overall plant growth and/or yield as compared to a plant which has not been genetically modified (e.g., a wild-type plant), particularly when the transgenic plant is grown in the presence of nitrogen. In specific embodiments, the method comprises contacting plant cells with nucleic acid encoding a miR167, wherein the nucleic acid is operably associated with a regulatory sequence, such as a tissue-specific (e.g., a pericycle-specific) promoter, to obtain transformed plant cells; producing plants from the transformed plant cells; and thereafter selecting a plant exhibiting increased lateral root growth, root biomass, nutrient uptake, overall plant growth and/or yield as compared to a plant which has not been genetically modified (e.g., a wild-type plant), particularly when the transgenic plant is grown in a nitrogen-moderate or nitrogen-rich environment (e.g., soil treated with a fertilizer).

In some embodiments, a regulatory sequence, such as a promoter, useful in the compositions and methods provided herein can be derived from any known pericycle-specific gene or the orthologous gene from any other plant species using methods currently known in the art or described elsewhere herein. However, functional fragments of the selected regulatory sequence may also be used which confer a modified transcriptional activity upon nucleic acid sequence which are operably linked to the regulatory sequence. By "modified transcriptional activity" is meant transcription of linked sequences above or below wild-type expression of the linked sequence.

6.1 miRNAs miRNAs are a large class of about 21- to 24-nucleotide noncoding, regulatory RNAs, which are found not only in plants, but also in nematodes, *Drosophila*, and humans. There are many miRNA genes, which have different patterns of expression patterns dependant on the tissue-type and stage of development. When these miRNAs are expressed, they pair to sites within the 3' untranslated region ("UTR") of target mRNAs, triggering the translational repression of the mRNA targets. By contrast to animals, the miRNA target sites in plants are generally within the coding sequence. miRNAs are single-stranded, and their accumulation is developmentally regulated. They derive from partially double-stranded precursor RNAs that are transcribed from genes that do not encode protein. Most of the miRNAs (in animals) lack complete complementarity to any putative target mRNA, but were thought to perhaps regulate gene expression during development, perhaps at the level of development. In plants, complete complementarity of miR-NAs to their target is more common.

As used herein, a "microRNA" or an "miRNA" is given its ordinary meaning in the art. Typically, an miRNA is a RNA molecule derived from genomic loci processed from transcripts that can form local RNA precursor miRNA structures. The mature miRNA usually has 20 to 24 nucleotides, although in some cases, other numbers of nucleotides may be present (for example, between 18 and 26 nucleotides). miRNAs are usually detectable on Northern blots. The miRNA has the potential to pair to flanking genomic sequences, placing the mature miRNA within an imperfect RNA duplex which may be needed for its processing from a longer precursor transcript. In addition, miRNAs are typically derived from a segment of the genome that is distinct from predicted protein-coding regions. As used herein, "plant-derived" miRNA is miRNA that is produced using precursor miRNAs expressed naturally in a plant cell. For instance, the miRNA precursor, or at least a portion thereof (for example, a hairpin or stem-loop motif, as further discussed below), can be expressed from a native plant gene.

miRNA is typically produced through the processing of precursor miRNA. Thus, in certain embodiments, a precursor miRNA is processed to produce miRNA in a plant cell. In specific embodiments, the precursor miRNA is a precursor MiR167 that is processed to produce miR167 in a plant cell (such as a pericycle cell). Additionally, the precursor miRNA may be isolated, e.g., from plant cells, according to certain embodiments. As used herein, "precursor miRNA" is generally composed of any type of nucleic acid-based molecules capable of accommodating miRNA sequences and stem-loop motifs incorporating the miRNA sequences. The precursor miRNA, such as a precursor miR167, may be naturally or artificially generated. Typically, the precursor miRNA molecule is an isolated nucleic acid having a stem-loop structure and a miRNA sequence incorporated therein. The miRNA sequences and the sequences including the stem-loop motifs do not all necessarily have to originate from the same organism. In some embodiments, the primary sequence of the precursor miRNA, exclusive of the miRNA, is derived from natural sequences flanking plant-derived miRNAs, such as miR167.

The compositions provided herein comprise precursor RNA constructs for the expression, and preferably the overexpression and/or inducible expression or overexpression, of an RNA precursor, such as miR167 precursor. The precursor RNA construct can comprise a promoter that is expressed in a plant cell driving the expression of a nucleotide sequence that encodes the precursor RNA having a miRNA. The RNA precursor can be cleaved in a plant cell to form the miRNA. The miRNA is complementary to a portion of a target gene or nucleotide sequence and function to modulate expression of the target sequence or gene, (e.g., ARF8) and/or indirectly modulate expression or repression of downstream genes that are regulated by the target gene. The precursor RNA constructs are designed to direct the expression in the plant an RNA precursor that has an miRNA that is complementary to a portion of a target nucleotide sequence. Such precursor RNAs, their respective miRNAs and the genes that encode them are known in the art and have been identified in plants. See, e.g., Reinhart et al., 2002, Genes & Development 16:1616-1626, Llave et al., 2002, Plant Cell 14:1605-1619, and Wu et al., 2006, Development, 133.4211. The nucleotide sequence that encodes the precursor RNA can comprise an miRNA region that is complementary to a portion of the target gene. The regions which flank the miRNA region are selected from the sequences known in the art for miRNA precursors, particularly plant miRNA precursors, more particularly those plant miRNA precursors disclosed by Reinhart et al., 2002, Genes & Development 16:1616-1626, Llave et al., 2002, Plant Cell 14:1605-1619 and Wu et al., 2006, Development, 133.4211. In general, an RNA precursor is constructed by obtaining the sequence of known RNA precursor for an miRNA and replacing the miRNA sequences therein with the miRNA sequences directed to the target gene of interest. Methods for constructing precursor miRNAs and miRNAs that can be used to alter the expression of specific target genes are known in the art. See, for example, McManus et al., 2002, RNA 8:842-850. Alternatively, precursor miRNAs from the same or a different plant (or other) species can be isolated by methods known in the art (Reinhart et al., 2002, Genes & Development 16:1616-1626 and Llave et al., 2002, Plant Cell 14:1605-1619).

The precursor miRNA can be cleaved or otherwise processed by the plant cell to produce miRNA substantially complementary to at least a portion of an mRNA sequence encoding a gene. For a target gene of interest, the miRNA, such as the miR167, is complementary or partially complementary to a region of the target gene. That is the miRNA comprises a region that is completely complementary to a region of the target gene, or the miRNA comprises a region that is partially complementary to a region of the target gene. By partially complementary, it is intended the corresponding regions of the target gene and the miRNA have one, two, three, or more mismatched bases. It is recognized in the art that miRNAs may not be completely complementary to the region of a target gene.

The double-stranded portion of the nucleic acid may remain double-stranded even if the two nucleotide regions forming the double-stranded portions are not perfectly complementary to each other, i.e., the two regions are substantially complementary to each other. For example, additions, deletions, substitutions, etc. may occur in one region relative to the other, and in some cases, one region itself may contain stem-loop motifs or other secondary structures that are not found in the complementary region. However, the two regions may be substantially complementary in that the two regions can interact in a predictable fashion to produce the double-stranded or "stem" portion of the stem-loop motif. Stem-loop motifs are well known in the art. The actual primary sequence of nucleotides within the stem-loop structure is not critical to the practice of the invention, as long as the secondary structure is generally present. Those of ordinary skill in the art will be able to determine, given a nucleic acid having a primary sequence of nucleotides, whether the nucleic acid is able to form a stem-loop motif.

The precursor miRNA may include homologous or heterologous stem-loop and miRNA sequence components. Transfection of a precursor miRNA containing a heterologous sequence into a cell may result in the formation of a transgenic plant cell. Thus, in some instances, the precursor miRNA, such as a precursor miR167, will include a stem-loop structure that is not ordinarily associated in nature with the miRNA with which it is associated in the precursor molecule. In a homologous structure the two components are ordinarily found in association with one another in nature. A heterologous precursor miRNA may be produced by replacing a portion (e.g., the homologous miRNA from the stem-loop structure) of a precursor miRNA taken from a plant cell with a sequence substantially complementary to another gene, for example, a gene that is desired to be inhibited or otherwise altered. The portion of the precursor miRNA that is substantially complementary to the replaced miRNA portion may also be replaced with a sequence that is substantially complementary to the gene newly added to the precursor miRNA. In some cases, a heterologous precursor miRNA may be produced by selecting a sequence substantially complementary to a gene that is desired to be inhibited or otherwise altered, pairing it with a substantially complementary, and adding the paired sequence to a stem-loop structure, which may be artificially generated in some cases. For example, a precursor miRNA may be created by selecting a sequence substantially complementary to a gene that is desired to be inhibited or otherwise altered, pairing it with a substantially complementary sequence, and adding a sequence that includes a stem-loop motif (other sequences may optionally be included within the stem-loop motif as well, in some embodiments). Optionally, one or more other sequences may also be added to the precursor miRNA.

miRNAs, such as an miR167, that can be used in the compositions and methods provided herein may be derived from any plant (or other) species, such as, for example, *Arabidopsis thaliana* or other *Arabidopsis* species, *Oryza sativa* or other *Oryza* species, or the like.

Precursor miRNA sequences are typically produced by transcribing a portion of the cell's DNA into RNA. Thus, a nucleotide sequence able to be transcribed by a plant cell into precursor miRNA that is cleavable by the plant cell to produce miRNA. The gene to be partially or totally inhibited, or otherwise altered, may be any plant cell gene that is capable of being transcribed into a protein. In certain embodiments, miR167 regulates, either directly or indirectly, expression of ARF8, and potentially regulates, either directly or indirectly, expression of ARF6 (At1g30330), or At3g61310, and/or downstream gene products modulated by ARF8 (FIG. 2B), such as At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440.

The particular gene to be inhibited will depend on the desired change to the cell. The methods and compositions of the invention are not limited to a particular gene. The nucleotide sequence may be isolated, e.g., from plant cells, according to certain embodiments, and the nucleotide sequence may be either DNA or RNA. Those of ordinary skill in the art will be able to determine if a given nucleotide sequence encodes a precursor miRNA sequence. In some embodiments, as further discussed below, the nucleotide sequence may be delivered to a plant cell, such as a root cell (e.g., a pericycle cell) and then the nucleotide sequence may then be expressed by the plant cell. In certain embodiments, the nucleotide sequence encodes a precursor miR167 operably linked to a pericycle-specific or pericycle-preferred promoter, wherein the miR167 is overexpressed in the plant as compared to a wild-type plant. In other embodiments, the miR167 is inducibly-expressed in the plant.

Precursor miRNAs, according to the invention, are not limited to wild-type or homologous precursor miRNAs. In some embodiments, a modified precursor miRNA, where a portion of the precursor miRNA, such as the region encoding the mature miRNA, is replaced in some fashion with another miRNA sequence. Any suitable miRNA sequence may be used, for example, miRNA sequences directed to the inhibition of a gene, partially or totally, within the plant cell. In some cases, the new miRNA sequence added to the precursor miRNA may be shorter or longer than the original miRNA sequence. For instance, one aspect of the invention is generally directed to an isolated precursor miRNA able to inhibit a gene in a plant cell. A portion of a precursor miRNA, or a nucleotide sequence able to be transcribed by a plant cell into precursor miRNA, may be replaced with a sequence substantially complementary to a gene to be inhibited. Methods using such isolated precursor miRNA, or nucleotide sequences encoding such precursor miRNA, to partially or totally inhibit, or otherwise alter a gene are also provided in certain embodiments. For instance, a precursor miRNA may be inserted into a plant cell, and/or a nucleotide sequence encoding a precursor miRNA may be inserted into a plant cell such that the nucleotide sequence can be transcribed by the plant cell into precursor miRNA. In specific embodiments, the miRNA is miR167.

Thus, the present invention also provides, according to various aspects, methods and compositions for the expression of precursor miRNA in plants, for example, to inhibit a gene. In some cases, the expression of miRNA and/or precursor miRNA in a plant cell can also be altered by altering the environment that the cell is in. In certain embodiments, the plant is in a nitrogen-moderate or nitrogen-rich environment.

In some embodiments, a precursor RNA construct is designed to produce a transcript that would be processed via the miRNA pathway to produce an miRNA complementary to a target RNA, an RNA corresponding or transcribed by the target sequence. While not bound by any mechanism of action, the miRNAs alter the production, processing, stability, or translation of the target RNA and thereby alter the expression of the protein product of the targeted RNA. The miRNAs of the invention will be complementary or substantially complementary to a target RNA that corresponds to the target gene of interest. In certain embodiments, the target polynucleotide is ARF8. By regulating ARF8, miR167 also indirectly regulates downstream gene products modulated by ARF8 (FIG. 2B), such as At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440. miR167 is also predicted to regulate, either directly or indirectly, expression of ARF6 (At1g30330) and At3g61310.

The miRNA will generally be small molecules comprising about 15 to about 30 nucleotides, about 20 to about 28 nucleotides, more specifically about 21-24 nucleotides. In certain embodiments, the miR167 is 24 nucleotides in length. Generally the miRNA will be completely complementary to the target RNA, however, mismatches may be tolerated. Generally from 1-about 6 mismatches may occur, more specifically about 2-3 mismatched nucleotides may be included in the miRNA. While the mismatched nucleotides may occur throughout the miRNA sequence, preferably, they are located near the center of the molecule. In this manner, an miRNA sequence can be designed to modulate the expression of a target sequence. The miRNA is expressed as part of a precursor RNA construct. As noted above, once the precursor RNA construct is expressed in the plant cell, it is processed to produce the miRNAs, preferably miR167.

6.2 Modulation of Gene Expression

The methods of the invention involve nitrogen-responsive miRNA, such as miR167, modulation of the expression of one, two, or more target nucleotide sequences in a plant, and preferably the plant pericycle, are provided. That is, the expression of a target nucleotide sequence of interest (or downstream product thereof) may be increased or decreased.

The target nucleotide sequences may be endogenous or exogenous in origin. By "modulate expression of a target gene" is intended that the expression of the target gene is increased or decreased relative to the expression level in a plant that has not been altered by the methods described herein. For example, in some embodiments, miR167 regulates, either directly or indirectly, expression of ARF8, and thus, in turn, downstream gene products modulated by ARF8 (FIG. 2B), such as At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440. miR167 is also predicted to regulate, either directly or indirectly, expression of ARF6 (At1g30330) and At3g61310.

By "increased expression" is intended that expression of the target nucleotide sequence is increased over expression observed in conventional transgenic lines for heterologous genes and over endogenous levels of expression for homologous genes. Heterologous or exogenous genes comprise genes that do not occur in the plant of interest in its native state. Homologous or endogenous genes are those that are natively present in the plant genome. Generally, expression of the target sequence is substantially increased. That is expression is increased at least about 25%-50%, preferably about 50%-100%, more preferably about 100%, 200% and greater.

By "decreased expression" is intended is intended that expression of the target nucleotide sequence is decreased below expression observed in conventional transgenic lines for heterologous genes and below endogenous levels of expression for homologous genes. Generally, expression of the target nucleotide sequence of interest is substantially decreased. That is expression is decreased at least about 25%-50%, preferably about 50%-100%, more preferably about 100%, 200% and greater.

Expression levels may be assessed by determining the level of a gene product by any method known in the art including, but not limited to determining the levels of the RNA and protein encoded by a particular target gene. For genes that encode proteins, expression levels may determined, for example, by quantifying the amount of the protein present in plant cells, or in a plant or any portion thereof. Alternatively, it desired target gene encodes a protein that has a known measurable activity, then activity levels may be measured to assess expression levels.

The target nucleotide sequence comprises any nucleotide sequence or gene of interest, including genes, regulatory sequences, and the like. Exemplary polynucleotides regulated either directly or indirectly by miR167 include, but are not limited to, ARF8, ARF6, At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440.

6.3 Modulators

The regulation of a gene via miRNA can be used in combination with a modulator. Such modulators include, but are not limited to, viral (or cellular) proteins that regulate miRNA accumulation. The modulators of the invention are capable of altering the levels of at least one miRNA in a plant. For example, HC-Pro, a viral suppressor of RNA silencing, enhances the accumulation of endogenous miRNAs. Thus, in certain embodiments, modulators can be used in combination with the miRNA precursor constructs provided herein to enhance the regulatory capabilities of miRNA, such as miR167, that correspond to target sequences of interest, such as ARF8. In some embodiments, a modulator is used to alter regulation of the miRNA pathway. In certain embodiments, the modulator works to enhance the accumulation of miRNAs.

Variant modulator proteins can also be utilized in certain embodiments. Variant proteins encompassed by the present invention are biologically active, that is they continue to possess the desired biological activity of the native protein, that is, modulator activity as described herein. Biologically active variants of a native modulator protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few 5, as few as 4, 3, 2, or even 1 amino acid residue.

6.4 Transformation Transfection

Any method or delivery system may be used for the delivery and/or transfection of the precursor miRNA, such as miR167, or a nucleotide sequence able to be transcribed to produce precursor miRNA in the cell. The precursor miRNA, or the nucleotide sequence able to be transcribed to produce precursor miRNA, may be delivered to the plant cell either alone, or in combination with other agents.

Transfection may be accomplished by a wide variety of means, as is known to those of ordinary skill in the art. Such methods include, but are not limited to, *Agrobacterium*-mediated transformation (e.g., Komari et al., 1998, Curr. Opin. Plant Biol., 1:161), particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., Sambrook et al., 1989, Molecular Cloning: A Laboratory Manual, 2nd ed., Cold Spring Harbor Laboratory Press, New York). For example, in one embodiment of the present invention, *Arabidopsis* or another plant species is transformed with a gene encoding a precursor miRNA such as miR167 using *Agrobacterium*.

One of skill in the art will be able to select an appropriate vector for introducing the miR167-encoding nucleic acid sequence in a relatively intact state. Thus, any vector which will produce a plant carrying the introduced miR167-encoding nucleic acid should be sufficient. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference).

Plant cells and plants can comprise two or more nucleotide sequence constructs. Any means for producing a plant comprising the nucleotide sequence constructs described herein are encompassed by the present invention. For example, a nucleotide sequence encoding the modulator can be used to transform a plant at the same time as the nucleotide sequence encoding the precursor RNA. The nucleotide sequence encoding the precursor mRNA can be introduced into a plant that has already been transformed with the modulator nucleotide sequence. Alternatively, transformed plants, one expressing the modulator and one expressing the RNA precursor, can be crossed to bring the genes together in the same plant. Likewise, viral vectors may be used to express gene products by various methods generally known in the art. Suitable plant viral vectors for expressing genes should be self-replicating, capable of systemic infection in a host, and stable. Additionally, the viruses should be capable of containing the nucleic acid sequences that are foreign to the native virus forming the vector. Transient expression systems may also be used.

*Agrobacterium* transformation is widely used by those skilled in the art to transform dicotyledonous species. Recently, there has been substantial progress towards the routine production of stable, fertile transgenic plants in almost all economically relevant monocot plants (Toriyarna et al., 1988, Bio/Technology 6:1072-1074; Zhang et al., 1988, Plant Cell Rep. 7:379-384; Zhang et al., 1988, Theor. Appl. Genet. 76:835-840; Shimamoto et al., 1989, Nature 338:274-276; Datta et al., 1990, Bio/Technology 8: 736-740; Christou et al., 1991, Bio/Technology 9:957-962; Peng et al., 1991, International Rice Research Institute, Manila, Philippines, pp. 563-574; Cao et al., 1992, Plant Cell Rep. 11:585-591; Li et al., 1993, Plant Cell Rep. 12:250-255; Rathore et al., 1993, Plant Mol. Biol. 21:871-884; Fromm et al., 1990, Bio/Technology 8:833-839; Tomes et al., 1995, "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); D'Halluin et al., 1992, Plant Cell 4:1495-1505; Walters et al., 1992, Plant Mol. Biol. 18:189-200; Koziel et al., 1993, Biotechnology 11: 194-200; Vasil, I. K., 1994, Plant Mol. Biol. 25:925-937; Weeks et al., 1993, Plant Physiol. 102:1077-1084; Somers et al., 1992, Bio/Technology 10: 1589-1594; WO 92/14828). In particular, *Agrobacterium* mediated transformation is now emerging also as an highly efficient transformation method in monocots (Hiei et al., 1994, The Plant Journal 6:271-282). See also, Shimamoto, K., 1994, Current Opinion in Biotechnology 5:158-162; Vasil et al., 1992, Bio/Technology 10:667-674; Vain et al., 1995, Biotechnology Advances 13(4):653-671; Vasil et al., 1996, Nature Biotechnology 14:702).

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

6.4.1 Agrobacterium miR167-encoding nucleic acid sequences utilized in the present invention can be introduced into plant cells using Ti plasmids of *Agrobacterium tumefaciens* (*A. tumefaciens*), root-inducing (Ri) plasmids of *Agrobacterium rhizogenes* (*A. rhizogenes*), and plant virus vectors. For reviews of such techniques see, for example, Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9, and Horsch et al., 1985, Science, 227:1229.

In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective in the transformation of plant cells (De Framond, Biotechnology, 1983, 1:262; Hoekema et al., 1983, Nature, 303:179). Such a binary system is preferred because it does not require integration into the Ti plasmid of *A. tumefaciens*, which is an older methodology.

In some embodiments, a disarmed Ti-plasmid vector carried by *Agrobacterium* exploits its natural gene transferability (EP-A-270355, EP-A-01 16718, Townsend et al., 1984, NAR, 12:8711, U.S. Pat. No. 5,563,055).

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in planta transformation by *Agrobacterium*, as described by Bechtold et al., (C. R. Acad. Sci. Paris, 1993, 316:1194). This approach is based on the vacuum infiltration of a suspension of *Agrobacterium* cells.

In certain embodiments, a miR167-encoding nucleic acid is introduced into plant cells by infecting such plant cells, an explant, a meristem or a seed, with transformed *A. tumefaciens* as described above. Under appropriate conditions known in the art, the transformed plant cells are grown to form shoots, roots, and develop further into plants.

Other methods described herein, such as microprojectile bombardment, electroporation and direct DNA uptake can be used where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

6.4.2 CaMV

In some embodiments, cauliflower mosaic virus (CaMV) is used as a vector for introducing miR167 nucleic acid into plant cells (U.S. Pat. No. 4,407,956). CaMV viral DNA genome can be inserted into a parent bacterial plasmid creating a recombinant DNA molecule which can be propagated in bacteria. After cloning, the recombinant plasmid again can be cloned and further modified by introduction of the desired nucleic acid sequence. The modified viral portion of the recombinant plasmid can then be excised from the parent bacterial plasmid, and used to inoculate the plant cells or plants.

6.4.3 Mechanical and Chemical Means

In some embodiments, miR167-encoding nucleic acid is introduced into a plant cell using mechanical or chemical means. Exemplary mechanical and chemical means are probided below.

As used herein, the term "contacting" refers to any means of introducing a miR167-encoding nucleic acid into a plant cell, including chemical and physical means as described above. Preferably, contacting refers to introducing the nucleic acid or vector containing the nucleic acid into plant cells (including an explant, a meristem or a seed), via *A. tumefaciens* transformed with the miR167-encoding nucleic acid as described above.

6.4.3.1 Microinjection

In one embodiment, the miR167 nucleic acid can be mechanically transferred into the plant cell by microinjection using a micropipette. See, e.g., WO 9209696, WO 9400583, EP 331083, EP 175966, Green et al., 1987, Plant Tissue and Cell Culture, Academic Press, Crossway et al., 1986, Biotechniques 4:320-334.

6.4.3.2 PEG

In other embodiment, the nucleic acid can also be transferred into the plant cell by using polyethylene glycol (PEG) which forms a precipitation complex with genetic material that is taken up by the cell.

6.4.3.3 Electroporation

Electroporation can be used, in another set of embodiments, to deliver a nucleic acid to the cell, e.g., precursor miRNA, or a nucleotide sequence able to be transcribed to produce precursor miRNA (see, e.g., Fromm et al., 1985, PNA5, 82:5824). "Electroporation," as used herein, is the application of electricity to a cell, such as a plant protoplast, in such a way as to cause delivery of a nucleic acid into the cell without killing the cell. Typically, electroporation includes the application of one or more electrical voltage "pulses" having relatively short durations (usually less than 1 second, and often on the scale of milliseconds or microseconds) to a media containing the cells. The electrical pulses typically facilitate the non-lethal transport of extracellular nucleic acids into the cells. The exact electroporation protocols (such as the number of pulses, duration of pulses, pulse waveforms, etc.), will depend on factors such as the cell type, the cell media, the number of cells, the substance(s) to be delivered, etc., and can be determined by those of ordinary skill in the art. Electroporation is discussed in greater detail in, e.g., EP 290395, WO 8706614, Riggs et al., 1986, Proc. Natl. Acad. Sci. USA 83:5602-5606; D'Halluin et al., 1992, Plant Cell 4:1495-1505). Other forms of direct DNA uptake can also be used in the methods provided herein, such as those discussed in, e.g., DE 4005152, WO 9012096, U.S. Pat. No. 4,684,611, Paszkowski et al., 1984, EMBO J. 3:2717-2722.

6.4.3.4 Ballistic and Particle Bombardment

Another method for introducing a miR167-encoding nucleic acid into a plant cell is high velocity ballistic penetration by small particles with the nucleic acid to be introduced contained either within the matrix of such particles, or on the surface thereof (Klein et al., 1987, Nature 327:70). Genetic material can be introduced into a cell using particle gun ("gene gun") technology, also called microprojectile or microparticle bombardment. In this method, small, high-density particles (microprojectiles) are accelerated to high velocity in conjunction with a larger, powder-fired macroprojectile in a particle gun apparatus. The microprojectiles have sufficient momentum to penetrate cell walls and membranes, and can carry RNA or other nucleic acids into the interiors of bombarded cells. It has been demonstrated that such microprojectiles can enter cells without causing death of the cells, and that they can effectively deliver foreign genetic material into intact tissue. Bombardment transformation methods are also described in Sanford et al. (Techniques 3:3-16, 1991) and Klein et al. (Bio/Techniques 10:286, 1992). Although, typically only a single introduction of a new nucleic acid sequence(s) is required, this method particularly provides for multiple introductions.

Particle or microprojectile bombardment are discussed in greater detail in, e.g., the following references: U.S. Pat. No. 5,100,792, EP-A-444882, EP-A-434616; Sanford et al., U.S. Pat. No. 4,945,050; Tomes et al., 1995, "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al., 1988, Biotechnology 6:923-926.

6.4.3.5 Colloidal Dispersion

In other embodiments, a colloidal dispersion system may be used to facilitate delivery of a nucleic acid into the cell, for example, precursor miRNA, or a nucleotide sequence able to be transcribed to produce precursor miRNA. As used herein, a "colloidal dispersion system" refers to a natural or synthetic molecule, other than those derived from bacteriological or viral sources, capable of delivering to and releasing the nucleic acid to the cell. Colloidal dispersion systems include, but are not limited to, macromolecular complexes, beads, and lipid-based systems including oil-in-water emulsions, micelles, mixed micelles, and liposomes. One example of a colloidal dispersion system is a liposome. Liposomes are artificial membrane vessels. It has been shown that large unilamellar vessels ("LUV"), which-range in size from 0.2 to 4.0 microns, can encapsulate large macromolecules within the aqueous interior and these macromolecules can be delivered to cells in a biologically active form (e.g., Fraley et al., 1981, Trends Biochem. Sci., 6:77).

6.4.3.6 Lipids

Lipid formulations for the transfection and/or intracellular delivery of nucleic acids are commercially available, for instance, from QIAGEN, for example as EFFECTENE® (a non-liposomal lipid with a special DNA condensing enhancer) and SUPER-FECT® (a novel acting dendrimeric technology) as well as Gibco BRL, for example, as LIPO-FECTIN® and LIPOFECTACE®, which are formed of cationic lipids such as N-[1-(2,3-dioleyloxy)-propyl]-N,N, N-trimethylammonium chloride ("DOTMA") and dimethyl dioctadecylammonium bromide ("DDAB"). Liposomes are well known in the art and have been widely described in the literature, for example, in Gregoriadis, G., 1985, Trends in Biotechnology 3:235-241; Freeman et al., 1984, Plant Cell Physiol. 29:1353).

6.4.3.7 Other Methods

In addition to the above, other physical methods for the transformation of plant cells are reviewed in the following and can be used in the methods provided herein. Oard, 1991, Biotech. Adv. 9:1-11. See generally, Weissinger et al., 1988, sAnn. Rev. Genet. 22:421-477; Sanford et al., 1987, Particulate Science and Technology 5:27-37; Christou et al., 1988, Plant Physiol. 87:671-674; McCabe et al., 1988, Bio/Technology 6:923-926; Finer and McMullen, 1991, In vitro Cell Dev. Biol. 27P:175-182; Singh et al., 1998, Theor. Appl. Genet. 96:319-324; Datta et al., 1990, Biotechnology 8:736-740; Klein et al., 1988, Proc. Natl. Acad. Sci. USA 85:4305-4309; Klein et al., 1988, Biotechnology 6:559-563; Tomes, U.S. Pat. No. 5,240,855; Buising et al., U.S. Pat. Nos. 5,322,783 and 5,324,646; Klein et al., 1988, Plant Physiol. 91:440-444; Fromm et al., 1990, Biotechnology 8:833-839; Hooykaas-Van Slogteren et al., 1984, Nature (London) 311:763-764; Bytebier et al., 1987, Proc. Natl. Acad. Sci. USA 84:5345-5349; De Wet et al., 1985, The Experimental Manipulation of Ovule Tissues, ed. Chapman et al. (Longman, N.Y.), pp. 197-209; Kaeppler et al., 1990, Plant Cell Reports 9:415-418 and Kaeppler et al., 1992, Theor. Appl. Genet. 84:560-566; Li et al., 1993, Plant Cell Reports 12:250-255 and Christou and Ford, 1995, Annals of Botany 75:407-413; Osjoda et al., 1996, Nature Biotechnology 14:745-750; all of which are herein incorporated by reference.

6.5 Nucleic Acid Constructs

The RNA precursor and modulator sequences of the invention may be provided in nucleotide sequence constructs or expression cassettes for expression in the plant of interest. The cassette will include 5' and 3' regulatory sequences operably linked to an miRNA nucleotide sequence or modulator nucleotide sequence of the invention.

The expression cassette may additionally contain at least one additional gene to be cotransformed into the organism. Alternatively, the additional gene(s) can be provided on multiple expression cassettes.

In certain embodiments, an expression cassette can be used with a plurality of restriction sites for insertion of the sequences of the invention to be under the transcriptional regulation of the regulatory regions. The expression cassette can additionally contain selectable marker genes (see below).

The expression cassette will generally include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of A. tumefaciens, such as the octopine synthase and nopaline synthase termination regions. See also Guerineau et al., 1991, Mol. Gen. Genet. 262:141-144; Proudfoot, 1991, Cell 64:671-674; Sanfacon et al., 1991, Genes Dev. 5:141-149; Mogen et al., 1990, Plant Cell 2:1261-1272; Munroe et al., 1990, Gene 91:151-158; Ballas et al., 1989, Nucleic Acids Res. 17:7891-7903; and Joshi et al., 1987, Nucleic Acid Res. 15:9627-9639.

In some embodiments, a nucleic acid (e.g., precursor miRNA, or a nucleotide sequence able to be transcribed to produce precursor miRNA) can be delivered to the cell in a vector. As used herein, a "vector" is any vehicle capable of facilitating the transfer of the nucleic acid to the cell such that the nucleic acid can be processed and/or expressed in the cell. The vector may transport the nucleic acid to the cells with reduced degradation, relative to the extent of degradation that would result in the absence of the vector. The vector optionally includes gene expression sequences or other components (such as promoters and other regulatory elements) able to enhance expression of the nucleic acid within the cell. The invention also encompasses the cells transfected with these vectors, including those cells previously described. In certain embodiments, the cells are pericycle cells transfected or transformed with a vector that specifically (or preferably) overexpresses miR167 in the pericycle cells of the plant, but not in the majority of other cell types of the plant.

To commence a transformation process in certain embodiments, it is first necessary to construct a suitable vector and properly introduce it into the plant cell. Vector(s) employed in the present invention for transformation of a plant cell include a miR167-encoding nucleic acid sequence operably associated with a promoter, such as a pericycle-specific promoter. Details of the construction of vectors utilized herein are known to those skilled in the art of plant genetic engineering.

In general, vectors useful in the invention include, but are not limited to, plasmids, phagemids, viruses, other vehicles derived from viral or bacterial sources that have been manipulated by the insertion or incorporation of the nucleotide sequences (or precursor nucleotide sequences) of the invention. Viral vectors useful in certain embodiments include, but are not limited to, nucleic acid sequences from the following viruses: retroviruses; adenovirus, or other adeno-associated viruses; mosaic viruses such as tobamoviruses; potyviruses, nepoviruses, and RNA viruses such as retroviruses. One can readily employ other vectors not named but known to the art. Some viral vectors can be based on non-cytopathic eukaryotic viruses in which non-essential genes have been replaced with the nucleotide sequence of interest. Non-cytopathic viruses include retroviruses, the life cycle of which involves reverse transcription of genomic viral RNA into DNA with subsequent proviral integration into host cellular DNA.

Genetically altered retroviral expression vectors can have general utility for the high-efficiency transduction of nucleic acids. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the cells with viral particles) are well known to those of ordinary skill in the art. Examples of standard protocols can be found in Kriegler, M., 1990, Gene Transfer and Expression, A Laboratory Manual, W.H. Freeman Co., New York, or Murry, E. J. Ed., 1991, Methods in Molecular Biology, Vol. 7, Humana Press, Inc., Clifton, N.J.

Another-example of a virus for certain applications is the adeno-associated virus, which is a double-stranded DNA virus. The adeno-associated virus can be engineered to be replication-deficient and is capable of infecting a wide range of-cell types and species. The adeno-associated virus further has advantages, such as heat and lipid solvent stability; high transduction frequencies in cells of diverse lineages; and/or lack of superinfection inhibition, which may allow multiple series of transductions.

Another vector suitable for use with the method provided herein is a plasmid vector. Plasmid vectors, have been extensively described in the art and are well-known to those of skill in the art. See, e.g., Sambrook et al., 1989, Molecular Cloning: A Laboratory Manual, Second Edition, Cold Spring Harbor Laboratory Press. These plasmids may have a promoter compatible with the host cell, and the plasmids can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom-designed, for example, using restriction enzymes and ligation reactions, to remove and add specific fragments of DNA or other nucleic acids, as necessary. The present invention also includes vectors for producing nucleic acids or precursor nucleic acids containing a desired nucleotide sequence (which can, for instance, then be cleaved or otherwise processed within the cell to produce a precursor miRNA). These vectors may include a sequence encoding a nucleic acid and an in vivo expression element, as further described below. In some cases, the in vivo expression element includes at least one promoter.

Where appropriate, the gene(s) for enhanced expression may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831, and 5,436,391, and Murray et al., 1989, Nucleic Acids Res. 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When desired, the sequence is modified to avoid predicted hairpin secondary mRNA structures. However, it is recognized that in the case of nucleotide sequences encoding the miRNA precursors, one or more hairpin and other secondary structures may be desired for proper processing of the precursor into an mature miRNA and/or for the functional activity of the miRNA in gene silencing.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., 1989, PNAS USA 86:6126-6130); potyvirus leaders, for example, TEV leader (Tobacco Etch Virus) (Allison et al., 1986); MDMV leader (Maize Dwarf Mosaic Virus); Virology 154:9-20), and human immunoglobulin heavy-chain binding protein (BiP), (Macejak et al., 1991, Nature 353:90-94); untranslated leader from the coat protein miRNA of alfalfa mosaic virus (AMV RNA 4) (Jobling et al., 1987, Nature 325:622-625); tobacco mosaic virus leader (TMV) (Gallie et al., 1989, Molecular Biology of RNA, ed. Cech (Liss, New York), pp. 237-256); and maize chlorotic mottle virus leader (MCMV) (Lommel et al., 1991, Virology 81:382-385). See also, Della-Cioppa et al., 1987, Plant Physiol. 84:965-968.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

6.6 Promoters and Other Regulatory Sequences

In the broad method of the invention, at least one nucleic acid sequence encoding miR167 is operably linked with a promoter, such as a pericycle1-preferred or pericycle-specific promoter. It may be desirable to introduce more than one copy of a miR167 polynucleotide into a plant for enhanced miR167 expression. For example, multiple copies of a miR167 polynucleotide would have the effect of increasing production of miR167 even further in the plant. In specific embodiments, the miR167 polynucleotide is expressed primarily or entirely in pericycle specific cells of the plant.

In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates. In certain specific embodiments, the miR167 is under the control of a pericycle specific promoter, and may optionally comprise other regulatory elements that result in constitutive or inducible expression of the miR167.

Thus, the nucleic acid, in one embodiment, is operably linked to a gene expression sequence, which directs the expression of the nucleic acid within the cell (e.g., to produce the precursor miRNA). A "gene expression sequence," as used herein, is any regulatory nucleotide sequence, such as a promoter sequence or promoter-enhancer combination, which facilitates the efficient transcription and translation of the nucleotide sequence to which it is operably linked. The gene expression sequence may, for example, be a eukaryotic promoter or a viral promoter, such as a constitutive or inducible promoter. Promoters and enhancers consist of short arrays of DNA sequences that interact specifically with cellular proteins involved in transcription, for instance, as discussed in Maniatis et al., 1987, Science 236:1237. Promoter and enhancer elements have been isolated from a variety of eukaryotic sources including genes in plant, yeast, insect and mammalian cells and viruses (analogous control elements, i.e., promoters, are also found in prokaryotes). In some embodiments, the nucleic acid is linked to a gene expression sequence which permits expression of the nucleic acid in a plant cell. A sequence which permits expression of the nucleic acid in a plant cell is one which is selectively active in the particular plant cell and thereby causes the expression of the nucleic acid in these cells. Those of ordinary skill in the art will be able to easily identify promoters that are capable of expressing a nucleic acid in a cell based on the type of plant cell.

A number of promoters can be used in the practice of the invention. The promoters can be selected based on the desired outcome. Generally, the RNA precursor nucleotide sequence and the modulator sequences can be combined with promoters of choice to alter gene expression if the target sequences in the tissue or organ of choice. Thus, the RNA precursor nucleotide sequence or modulator nucleotide sequence can be combined with constitutive, tissue-preferred, inducible, developmental, or other promoters for expression in plants depending upon the desired outcome.

The selection of a particular promoter and enhancer depends on what cell type is to be used and the mode of delivery. For example, a wide variety of promoters have been isolated from plants and animals, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, and promoters from other open reading frames in the T-DNA, such as ORF7, etc. Promoters isolated from plant viruses include the 35S promoter from cauliflower mosaic virus. Promoters that have been isolated and reported for use in plants include ribulose-1,3-biphosphate carboxylase small subunit promoter, phaseolin promoter, etc. Thus, a variety of promoters and regulatory elements may be used in the expression vectors of the present invention.

Promoters useful in the compositions and methods provided herein include both natural constitutive and inducible promoters as well as engineered promoters. The CaMV promoters are examples of constitutive promoters. Other constitutive mammalian promoters include, but are not limited to, polymerase promoters as well as the promoters for the following genes: hypoxanthine phosphoribosyl transferase ("HPTR"), adenosine deaminase, pyruvate kinase, and alpha-actin.

Promoters useful as expression elements of the invention also include inducible promoters. Inducible promoters are expressed in the presence of an inducing agent. For example, a metallothionein promoter can be induced to promote transcription in the presence of certain metal ions. Other inducible promoters are known to those of ordinary skill in the art. The in vivo expression element can include, as necessary, 5' non-transcribing and 5' non-translating sequences involved with the initiation of transcription, and can optionally include enhancer sequences or upstream activator sequences.

For example, in some embodiments an inducible promoter is used to allow control of nucleic acid expression through the presentation of external stimuli (e.g., environmentally inducible promoters), as discussed below. Thus, the timing and amount of nucleic acid expression can be controlled in some cases. Non-limiting examples of expression systems, promoters, inducible promoters, environmentally inducible promoters, and enhancers are well known to those of ordinary skill in the art. Examples include those described in International Patent Application Publications WO 00/2714, WO 00/1175, WO 00/2713, WO 0003012, WO 0003017, WO 0001832, WO 9950428, WO 9946976 and U.S. Pat. Nos. 6,028,250, 5,959,176, 5,907,086, 5,898,096, 5,824,857, 5,744,334, 5,689,044, and 5,612,472. A general descriptions of plant expression vectors and reporter genes can also be found in Gruber et al., 1993, "Vectors for Plant Transformation," in Methods in Plant Molecular Biology & Biotechnology, Glich et al., Eds., p. 89-119, CRC Press.

For plant expression vectors, viral promoters that can be used in certain embodiments include the 35S RNA and 19S RNA promoters of CaMV (Brisson et al., Nature, 1984, 310:511; Odell et al., Nature, 1985, 313:810); the full-length transcript promoter from Figwort Mosaic Virus (FMV) (Gowda et al., 1989, J. Cell Biochem., 13D: 301) and the coat protein promoter to TMV (Takamatsu et al., 1987, EMBO J. 6:307). Alternatively, plant promoters such as the light-inducible promoter from the small subunit of ribulose bis-phosphate carboxylase (ssRUBISCO) (Coruzzi et al., 1984, EMBO J., 3:1671; Broglie et al., 1984, Science, 224:838); mannopine synthase promoter (Velten et al., 1984, EMBO J., 3:2723) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., 1986, Mol. Cell. Biol., 6:559; Severin et al., 1990, Plant Mol. Biol., 15:827) may be used. Exemplary viral promoters which function constitutively in eukaryotic cells include, for example, promoters from the simian virus, papilloma virus, adenovirus, human immunodeficiency virus, Rous sarcoma virus, cytomegalovirus, the long terminal repeats of Moloney leukemia virus and other retroviruses, and the thymidine kinase promoter of herpes simplex virus. Other constitutive promoters are known to those of ordinary skill in the art.

To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., Proc. Natl. Acad. Sci., U.S.A., 90:4567, 1993); Int-1 and In2-2 regulator sequences which are activated by substituted benzenesulfonamides, e.g., herbicide safeners (Hershey et al., Plant Mol. Biol., 17:679, 1991); and the GRE regulatory sequences which are induced by glucocorticoids (Schena et al., Proc. Natl. Acad. Sci., U.S.A., 88:10421, 1991). Other promoters, both constitutive and inducible will be known to those of skill in the art.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al., 1983, Neth. J. Plant Pathol. 89:245-254; Uknes et al., 1992, Plant Cell 4:645-656; and Van Loon, 1985, Plant Mol. Virol. 4:111-116. Of particular interest are promoters that are expressed locally at or near the site of pathogen infection. See, for example, Marineau et al., 1987, Plant Mol. Biol. 9:335-342; Matton et al., 1989, Molecular Plant-Microbe Interactions 2:325-331; Somsisch et al., 1986, Proc. Natl. Acad. Sci. USA 83:2427-2430; Somsisch et al., 1988, Mol. Gen. Genet. 2:93-98; and Yang, 1996, Proc. Natl. Acad. Sci. USA 93:14972-14977. See also, Chen et al., 1996, Plant J. 10:955-966; Zhang et al., 1994, Proc. Natl. Acad. Sci. USA 91:2507-2511; Warner et al., 1993, Plant J. 3:191-201; Siebertz et al., 1989, Plant Cell 1:961-968; U.S. Pat. No. 5,750,386; Cordero et al., 1992, Physiol. Mol. Plant. Path. 41:189-200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan, 1990, Ann. Rev. Phytopath. 28:425-449; Duan et al., 1996, Nature Biotechnology 14:494-498); wun1 and wun2, U.S. Pat. No. 5,428,148; win1 and win2 (Stanford et al., 1989, Mol. Gen. Genet. 215:200-208); systemin (McGurl at al., 1992, Science 225: 1570-1573); WIPI (Rohmeier et al., 1993, Plant Mol. Biol. 22:783-792; Eckelkamp et al., 1993, FEBS Letters 323:73-76); MPI gene (Corderok et al., 1994, Plant J. 6(2):141-150); and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or, a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al., 1991, Proc. Natl. Acad. Sci. USA 88:10421-10425 and McNellis et al., 1998, Plant J. 14(2):247-257) and tetramiR167e-inducible and tetramiR167e-repressible promoters (see, for example, Gatz et al., 1991, Mol. Gen. Genet. 227:229-237, and U.S. Pat. Nos. 5,814,618 and 5,789,156), herein incorporated by reference.

Where enhanced expression in particular tissues is desired, tissue-preferred promoters can be utilized. Tissue-preferred promoters include those described by Yamamoto et al., 1997, Plant J. 12(2):255-265; Kawamata et al., 1997, Plant Cell Physiol. 38(7):792-803; Hansen et al., 1997, Mol. Gen. Genet. 254(3):337-343; Russell et al., 1997, Transgenic Res. 6(2):157-168; Rinehart et al., 1996, Plant Physiol. 112(3):1331-1341; Van Camp et al., 1996, Plant Physiol. 112(2):525-535; Canevascini et al., 1996, Plant Physiol. 12(2):513-524; Yamamoto et al., 1994, Plant Cell Physiol. 35(5):773-778; Lam, 1994, Results Probl. Cell Differ. 20:181-196; Orozco et al., 1993, Plant Mol. Biol. 23(6): 1129-1138; Matsuoka et al., 1993, Proc Natl. Acad. Sci. USA 90(20):9586-9590; and Guevara-Garcia et al., 1993, Plant J 4(3):495-505.

The particular promoter selected should be capable of causing sufficient expression to result in the production of an effective amount of structural gene product in the transgenic plant, e.g., miR167 to cause downregulation of genes such as ARF8, and increased lateral root growth, root biomass, overall plant growth or yield, and/or other phenotypes described herein, such as when the plant is grown in the presence of nitrogen (e.g., nitrogen-moderate or nitrogen-rich conditions) as compared to wild type. The promoters used in the vector constructs of the present invention may be modified, if desired, to affect their control characteristics. In certain embodiments, chimeric promoters can be used.

There are promoters known which limit expression to particular plant parts or in response to particular stimuli. For example, a root specific promoter would be desirable to obtain expression of miRNA in the plant roots, such as the pericycle. One skilled in the art will know of many such plant part-specific promoters which would be useful in the present invention. In certain embodiments, to provide pericycle-specific expression, any of a number of promoters from genes in *Arabidopsis* can be used. In some embodiments, the promoter from one (or more) of the following genes may be used: (i) At1g11080, (ii) At3g60160, (iii)

At1g24575, (iv) At3g45160, or (v) At1g23130. In specific embodiments, we will also use (vi) promoter elements from the GFP-marker line used in Gifford et al. (in preparation) (see also, Bonke et at, 2003, Nature 426, 181-6; Tian et al., 2004, Plant Physiol 135, 25-38). Several of the predicted genes have a number of potential orthologs in rice and poplar and thus we predict that they will be applicable for use in crop species; (i) Os04g44410, Os10g39560, Os06g51370, Os02g42310, Os01g22980, Os05g06660, and Poptr1#568263, Poptr1#555534, Poptr1#365170; (ii) Os04g49900, Os04g49890, Os01g67580, and Poptr1#87573, Poptr1#80582, Poptr1#565079, Poptr1#99223.

Promoters used in the nucleic acid constructs of the present invention can be modified, if desired, to affect their control characteristics. For example, the CaMV 355 promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

An efficient plant promoter that may be used in specific embodiments is an "overproducing" or "overexpressing" plant promoter. Overexpressing plant promoters that can be used in the compositions and methods provided herein include the promoter of the small sub-unit ("ss") of the ribulose-1,5-biphosphate carboxylase from soybean (e.g., Berry-Lowe et al., 1982, J. Molecular & App. Genet., 1:483), and the promoter of the chorophyll a-b binding protein. These two promoters are known to be light-induced in eukaryotic plant cells. For example, see Cashmore, Genetic Engineering of plants: An Agricultural Perspective, p. 29-38; Coruzzi et al., 1983, J. Biol. Chem., 258:1399; and Dunsmuir et al., 1983, J. Molecular & App. Genet., 2:285.

The promoters and control elements of, e.g., SUCS (root nodules; broadbean; Kuster et al., 1993, Mol Plant Microbe Interact 6:507-14) for roots can be used in compositions and methods provided herein to confer tissue specificity.

In certain embodiment, two promoter elements can be used in combination, such as, for example, (i) an inducible element responsive to a treatment that can be provided to the plant prior to N-fertilizer treatment, and (ii) a pericycle-specific expression element to drive miR167 expression in the pericycle root cell type alone.

Any promoter of other expression element described herein or known in the art may be used either alone or in combination with any other promoter or other expression element described herein or known in the art. For example, promoter elements that confer tissue specific expression of a gene (e.g., miR167) can be used with other promoter elements conferring consitutive or inducibel expression. In certain embodiments, two or more promoter elements can be used in combination, such as, for example, (i) an inducible element responsive to a treatment that can be provided to the plant prior to N-fertilizer treatment, and (ii) a pericycle-specific expression element to drive miR167 expression in the pericycle root cell type alone.

6.7 Isolating Related Promoter Sequences

Promoter and promoter control elements that are related to those described in herein can also be used in the compositions and methods provided herein. Such related sequence can be isolated utilizing (a) nucleotide sequence identity; (b) coding sequence identity of related, orthologous genes; or (c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation actixity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

Typically, related promoters exhibit at least 80% sequence identity, preferably at least 85%, more preferably at least 90%, and most preferably at least 95%, even more preferably, at least 96%, at least 97%, at least 98% or at least 99% sequence identity compared to those shown in Table 1. Such sequence identity can be calculated by the algorithms and computers programs described above.

Usually, such sequence identity is exhibited in an alignment region that is at least 75% of the length of a sequence or corresponding full-length sequence of a promoter described herein; more usually at least 80%; more usually, at least 85%, more usually at least 90%, and most usually at least 95%, even more usually, at least 96%, at least 97%, at least 98% or at least 99% of the length of a sequence of a promoter described herein.

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence of a promoter described herein. These related promoters may exhibit similar preferential transcription as those promoters described herein.

In certain embodiments, a promoter, such as a root-preferred or root specific promoter, can be identified by sequence homology or sequence identity to any root specific promoter identified herein. In other embodiments, orthologous genes identified herein as root-specific genes (e.g., the same gene or different gene that if functionally equivalent) for a given species can be identified and the associated promoter can also be used in the compostions and methods provided herein. For example, using high, medium or low stringency conditions, standard promoter rules can be used to identify other useful promoters from orthologous genes for use in the compositions and methods provided herein. In specific embodiments, the orthologous gene is a gene expressed only or primarily in the root, such as pericycle cells. In some embodiments, an expression vector that can be used in the compositions and methods of the invention comprises a miR167 polynucleotide operably linked to a regulatory nucleic acid sequence controlling the expression of a root specific or root preferred gene of a same or different species of plant.

Polynucleotides can be tested for activity by cloning the sequence into an appropriate vector, transforming plants with the construct and assaying for marker gene expression. Recombinant DNA constructs can be prepared, which comprise the polynucleotide sequences of the invention inserted into a vector suitable for transformation of plant cells. The construct can be made using standard recombinant DNA techniques (Sambrook et al., 1989) and can be introduced to the species of interest by Agrobacterium-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., 1992, Proc. Natl. Acad. Sci. USA 89: 8794-8797; Hamilton et al., 1996, Proc. Natl. Acad. Sci. USA 93: 9975-9979; (b) YAC: Burke et al., 1987, Science 236:806-812; (c) PAC: Stemberg N. et al., 1990, Proc Natl Acad Sci USA. January; 87(1):103-7; (d) Bacteria-Yeast Shuttle Vectors: Bradshaw et al., 1995, Nucl Acids Res 23: 4850-4856; (e) Lambda Phage Vectors: Replacement Vector, e.g., Frischauf et al., 1983, J. Mol. Biol. 170: 827-842; or Insertion vector, e.g., Huynh et al., 1985, In: Glover N M (ed) DNA Cloning: A practical Approach, Vol. 1 Oxford: IRL Press; T-DNA gene fusion vectors: Walden et al., 1990, Mol Cell Biol 1: 175-194; and (g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin (see below). Vectors can also include origins of replication, scaffold attachment regions (SARs), markers, homologous sequences, introns, etc.

6.8 Root Preferential Transcription

The invention also provides a method of providing increased transcription of a nucleic acid sequence in a selected tissue, such as the root (e.g., pericycle cells of the root). The method comprises growing a plant having integrated in its genome a nucleic acid construct comprising, an exogeneous gene encoding a miR167, said gene operably associated with a tissue specific promoter, whereby transcription of said gene is increased in said selected tissue.

Examples of promoters under developmental control include promoters that initiate transcription only, or preferentially, in certain tissues, such as roots. Exemplary promoters include the root cdc2a promoter (Doerner, P. et al., 1996, Nature 380:520-523) or the root peroxidase promoter from wheat (Hertig, C. et al., 1991, Plant Mol. Biol. 16:171-174). The operation of a promoter may also vary depending on its location in the genome. Thus, an inducible promoter may become fully or partially constitutive in certain locations.

Specific promoters may be used in the compositions and methods provided herein. As used herein, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used in the compositions and methods of the present invention, include RCc2 and RCc3, promoters that direct root-specific gene transcription in rice (Xu et al., 1995, Plant Mol. Biol. 27:237 and TobRB27, a root-specific promoter from tobacco (Yamamoto et al., 1991, Plant Cell 3:371). Examples of tissue-specific promoters under developmental control include promoters that initiate transcription only in certain tissues or organs, such as roots "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful (1) to modulate root size, shape, and development; (2) to modulate the number of roots, or root hairs; (3) to modulate mineral, fertilizer, or water uptake; (4) to modulate transport of nutrients; or (4) to modulate energy or nutrient usage in relation to other organs and tissues. Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues. For preferential up-regulation of transcription, promoter and control elements produce transcript levels that are above background of the assay.

Root-preferred promoters are known and can be selected from the many available from the literature. See, for example, Hire et al., 1992, Plant Mol. Biol. 20(2): 207-218 (soybean root-preferred glutamine synthetase gene); Keller and Baumgartner, 1991, Plant Cell 3(10):1051-1061 (root-preferred control element in the GRP 1.8 gene of French bean); Sanger et al., 1990, Plant Mol. Biol. 14(3):433-443 (root-preferred promoter of the mannopine synthase (MAS) gene of *Agrobacterium tumefaciens*); Miao et al., 1991, Plant Cell 3(1):11-22 (full-length cDNA clone encoding cytosolic glutamine synthetase (GS), which is expressed in roots and root nodules of soybean). Bogusz et al., 1990, Plant Cell 2(7):633-641 (root-preferred promoters from hemoglobin genes from the nitrogen-fixing nonlegume *Parasponia andersonii* and the related non-nitrogen-fixing nonlegume *Trema tomentosa*). Leach and Aoyagi, 1991, Plant Science (Limerick) 79(1):69-76 (ro1C and ro1D root-inducing genes of *Agrobacterium rhizogenes*); Teen et al., 1989, EMBO J. 8(2):343-350) (octopine synthase and TR2' gene); (VfENOD-GRP3 gene promoter); Kuster et al., 1995, Plant Mol. Biol. 29(4):759-772 and Capana et al., 1994, Plant Mol. Biol. 25(4):681-691 ro1B promoter. See also U.S. Pat. Nos. 5,837,876; 5,750,386; 5,633,363; 5,459,252; 5,401,836; 5,110,732; and 5,023,179, root-specific glutamine synthetase (see Tingey et al., 1987, EMBO J., 6:1-9; Edwards et al., 1990, PNAS, 87:3439-3463). In addition, promoters of the above-listed orthologous genes in other plant species can be identified and used in the compositions and methods provided herein.

In specific embodiments, the compositions and methods provided herein use root- or pericycle-specific promoters operably associated to a nucleotide encoding miR167. In certain embodiments, the promoter is a constitutive or inducible promoter.

6.9 Selectable Markers

Using any gene transfer technique, such as the above-listed techniques, an expression vector harboring the nucleic acid may be transformed into a cell to achieve temporary or prolonged expression. Any suitable expression system may be used, so long as it is capable of undergoing transformation and expressing of the precursor nucleic acid in the cell. In one embodiment, a pET vector (Novagen, Madison, Wis.), or a pBI vector (Clontech, Palo Alto, Calif.) is used as the expression vector. In some embodiments an expression vector further encoding a green fluorescent protein ("GFP") is used to allow simple selection of transfected cells and to monitor expression levels. Non-limiting examples of such vectors include Clontech's "Living Colors Vectors" pEYFP and pEYFP-C.

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding .beta.-glucuronidase (Jefferson, 1987, Plant Molec Biol. Rep 5:387-405), luciferase (Ow et al., 1986, Science 234:856-859), B and C1 gene products that regulate anthocyanin pigment production (Goff et al., 1990, EMBO J. 9:2517-2522).

In some cases, a selectable marker may be included with the nucleic acid being delivered to the cell. As used herein, the term "selectable marker" refers to the use of a gene that encodes an enzymatic or other detectable activity (e.g., luminescence or fluorescence) that confers the ability to grow in medium lacking what would otherwise be an essential nutrient. A selectable marker may also confer resistance to an antibiotic or drug upon the cell in which the selectable marker is expressed. Selectable markers may be "dominant" in some cases; a dominant selectable marker encodes an enzymatic or other activity (e.g., luminescence or fluorescence) that can be detected in any cell or cell line.

Optionally, a selectable marker may be associated with the miR167-encoding nucleic acid. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II. Other suitable markers will be known to those of skill in the art.

6.10 Selection and Identification of Transformed Plants and Plant Cells

According to the present invention, desired plants may be obtained by engineering the disclosed gene constructs into a variety of plant cell types, including but not limited to, protoplasts, tissue culture cells, tissue and organ explants, pollens, embryos as well as whole plants. In specific embodiments, the miR167 gene contructs are engineered into plant roots, such as pericycle cell, preferably with the use of a pericycle specific promoter.

In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be also to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

miRNA167-transgenic plants may also be identified by examining the change in expression of certain miRNA167-responsive genes. For example, a transgenic plant of the present invention can be identified by determining the expression of one or more of the genes listed in Table 1. In a plant of the invention, the expression of these genes is down-regulated compared to wild-type.

6.11 Screening of Transformed Plants for Those with Improved Agronomic Traits

According to the present invention, to obtain plants with improved agronomic characteristics, the transformed plants may be screened for those exhibiting the desired physiological alteration. Alternatively, the transformed plants may be directly screened for those exhibiting the desired agronomic changes. A plant with the desired improvement can be isolated by screening the engineered plants for altered expression pattern or level of the miR167 (or precursor thereof) and/or expression pattern or level of a direct or indirect target polynucleotide of the miR167, such as ARF8, or downstream gene products modulated by ARF8 (FIG. 2B), such as At3g61310, At1g76420, At1g24260, At1g79350, At1g63470, At2g20100, At3g45610; At2g26330, At3g57830, At2g01210; At3g16170, At1g48100, At1g11730, At1g70710 (CEL1), At1g32930, At3g13000, At2g38160, At1g03170, At3g13510, At2g23700, At3g11000, At3g10310, At2g42120, At1g15570, At2g26180, At1g67320 and/or At2g44440. miR167 also potentially regulates, either directly or indirectly, expression of ARF6 (At1g30330), or At3g61310. A plant can also be screened for lateral root growth, root surface area root biomass, nutrient uptake, overall increased plant growth rate, enhanced vegetative yield, or improved reproductive yields. The screening of the engineered plants can involve Southern analysis to confirm the presence and number of transgene insertions; Northern analysis, RNase protection, primer extension, reverse transcriptase/PCR and the like to measure mRNA levels; measuring the amino acid composition, free amino acid pool or total nitrogen content of various plant tissues; monitoring numbers and types of lateral root primordia and lateral roots; measuring growth rates in terms of fresh weight gains over time; or measuring plant yield in terms of total dry weight and/or total seed weight, or a combination of any of the above methods. The procedures and methods for examining these parameters are well known to those skilled in the art.

In other embodiments, the screening of the transformed plants may be for improved agronomic characteristics (e.g., faster growth, greater vegetative or reproductive yields, or improved protein contents, etc.), as compared to unengineered progenitor plants, when cultivated under nitrogen rich (e.g., N-rich soils or soil that has been fertilized with commercial or organic fertilizer) growth conditions (i.e., cultivated using soils or media containing or receiving sufficient amounts of nitrogen nutrients to sustain healthy plant growth).

Plants exhibiting increased growth and/or yield as compared with wild-type plants can be selected by visual observation, methods provided in the Examples, or other methods known in the art.

In another embodiment, the invention provides a method of producing a plant characterized as having increased growth and yield by contacting a plant capable of increased yield with a miR167-inducing amount of an agent which induces miR167 gene expression. Induction of miR167 gene expression results in production of a plant having increased lateral root growth and/or yield as compared to a plant not contacted with the agent.

A "plant capable of increased yield" refers to a plant that can be induced to express its endogenous miR167 gene to achieve increased yield. The term "promoter inducing amount" refers to that amount of an agent necessary to elevate miR167 gene expression above miR167 expression in a plant cell not contacted with the agent, by stimulating the endogenous miR167 promoter. For example, a transcription factor or a chemical agent may be used to elevate gene expression from native or chimeric miR167 promoter, thus inducing the promoter and miR167 gene expression.

According to the present invention, a desired plant is one that exhibits improvement over the control plant (i.e., progenitor, wild type plant) in one or more of the aforementioned parameters. In certain embodiments, the aforementioned parameters are compared between plants grown in nitrogen-moderate or nitrogen-rich cultivation conditions. In other embodiments, the aforementioned parameters are compared between a transgenic plant provided herein and a wild type plant, which are grown in nitrogen conditions in which lateral root growth is repressed in the wild type plant (e.g., nitrogen poor or other nitrogen conditions). In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

6.12 Cells

Optionally, germ line cells may be used in the methods described herein rather than, or in addition to, somatic cells. The term "germ line cells" refers to cells in the plant organism which can trace their eventual cell lineage to either the male or female reproductive cell of the plant. Other cells, referred to as "somatic cells" are cells which give rise to leaves, roots and vascular elements which, although important to the plant, do not directly give rise to gamete cells. Somatic cells, however, also may be used. With regard to callus and suspension cells which have somatic embryogenesis, many or most of the cells in the culture have the potential capacity to give rise to an adult plant. If the plant originates from single cells or a small number of cells from the embryogenic callus or suspension culture, the cells in the callus and suspension can therefore be referred to as germ cells. In the case of immature embryos which are prepared for treatment by the methods described herein, certain cells in the apical meristem region of the plant have been shown to produce a cell lineage which eventually gives rise to the female and male reproductive organs. With many or most species, the apical meristem is generally regarded as giving rise to the lineage that eventually will give rise to the gamete cells. An example of a non-gamete cell in an embryo would be the first leaf primordia in corn which is destined to give rise only to the first leaf and none of the reproductive structures.

6.13 Plant Regeneration

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al., 1984, in Cell Culture and Somatic Cell Genetics of Plants, Vols. I, II, and III, Laboratory Procedures and Their Applications (Academic Press); and Weissbach et al., 1989, Methods For Plant Mol. Biol.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Normally, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration (see Methods in Enzymology, Vol. 118 and Klee et al., Annual Review of Plant Physiology, 38:467, 1987). Utilizing the leaf disk-transformation-regeneration method of Horsch et al., Science, 227:1229, 1985, disks are cultured on selective media, followed by shoot formation in about 2-4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenics is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g., increased lateral root growth, uptake of nutrients, overall plant growth and/or vegetative or reproductive yields.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (setting) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize see, Gordon-Kamm et al., 1990, The Plant Cell, 2:601-618.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., 1983, Protoplasts Isolation and Culture, Handbook of Plant Cell Culture, Macmillan Publishing Company, New York, pp. 124-176; and Binding, Regeneration of Plants, Plant Protoplasts, 1985, CRC Press, Boca Raton, pp. 21-73.

The regeneration of plants containing the foreign gene introduced by *Agrobacterium* from leaf explants can be achieved as described by Horsch et al., 1985, Science, 227:1229-1231. In this procedure, transformants are grown in the presence of a selection agent and in a medium that induces the regeneration of shoots in the plant species being transformed as described by Fraley et al., 1983, Proc. Natl. Acad. Sci. (U.S.A.), 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

The regeneration of plants from either single plant protoplasts or various explants is well known in the art. See, for example, Methods for Plant Molecular Biology, A. Weissbach and H. Weissbach, eds., 1988, Academic Press, Inc., San Diego, Calif. This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., 1994, Springer, New York 1994; Corn and Corn Improvement, 3rd edition, Sprague and Dudley Eds., 1988, American Society of Agronomy, Madison, Wis.

6.14 Plants and Plant Cells

Also provided herein are a plant cell having the nucleotide sequence constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

In certain embodiments, a plant cell comprises a miR167 nucleotide sequence operably associated with a pericycle specific promoter, which is optionally a constitutive or inducible promoter. In other embodiments, a plant cell comprises multiple copies of a miR167 operably associated with a pericycle specific promoter. In specific embodiments provided herein are plants (and plant cells thereof) that overexpress, contitutionally express and/or inducibly express miR167 in the pericycle of the plant, as compared to other tissues in the plant and/or as compared to a wild type plant.

The present invention also provides a plant comprising a plant cell as disclosed. Transformed seeds and plant parts are also encompassed.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant. Plant extracts and derivatives are also provided.

Any species of woody, ornamental or decorative, crop or cereal, fruit or vegetable plant, and algae (e.g., *Chlamydomonas reinhardtii*) may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains.

Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

Examples of woody species include poplar, pine, *sequoia*, cedar, oak, etc.

Still other examples of plants include, but are not limited to, wheat, cauliflower, tomato, tobacco, corn, petunia, trees, etc.

In certain embodiments, plants of the present invention are crop plants (for example, cereals and pulses, maize, wheat, potatoes, tapioca, rice, sorghum, millet, cassaya, barley, pea, and other root, tuber, or seed crops. Exemplary cereal crops used in the compositions and methods of the invention include, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). Grain plants that provide seeds of interest include oil-seed plants and leguminous plants. Other seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Other important seed crops are oil-seed rape, sugar beet, maize, sunflower, soybean, and sorghum. Leguminous plants include beans and peas. Beans include guar, locust bean, fenugreek, soybean, garden beans, cowpea, mungbean, lima bean, fava bean, lentils, chickpea, etc.

Horticultural plants to which the present invention may be applied may include lettuce, endive, and vegetable brassicas including cabbage, broccoli, and cauliflower, and carnations and geraniums. The present invention may also be applied to tobacco, cucurbits, carrot, strawberry, sunflower, tomato, pepper, chrysanthemum, poplar, eucalyptus, and pine.

The present invention may be used for transformation of other plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*, cotton (*Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

6.15 Cultivation

One skilled in the art knows what constitute nitrogen-poor and nitrogen-rich growth conditions for the cultivation of most, if not all, important crop and ornamental plants. For example, for the cultivation of wheat see Alcoz et al., 1993, Agronomy Journal 85:1198-1203; Rao and Dao, 1992, J. Am. Soc. Agronomy 84:1028-1032; Howard and Lessman, 1991, Agronomy Journal 83:208-211; for the cultivation of corn see Tollenear et al., 1993, Agronomy Journal 85:251-255; Straw et al., Tennessee Farm and Home Science: Progress Report, Spring 1993, 166:20-24; Miles, S. R., 1934, J. Am. Soc. Agronomy 26:129-137; Dara et al., 1992, J. Am. Soc. Agronomy 84:1006-1010; Binford et al., 1992, Agronomy Journal 84:53-59; for the cultivation of soybean see Chen et al., 1992, Canadian Journal of Plant Science 72:1049-1056; Wallace et al., 1990, Journal of Plant Nutrition 13:1523-1537; for the cultivation of rice see Oritani and Yoshida, 1984, Japanese Journal of Crop Science 53:204-212; for the cultivation of linseed see Diepenbrock and Porksen, 1992, Industrial Crops and Products 1:165-173; for the cultivation of tomato see Grubinger et al., 1993, Journal of the American Society for Horticultural Science 118:212-216; Cerne, M., 1990, Acta Horticulture 277:179-182; for the cultivation of pineapple see Magistad et al., 1932, J. Am. Soc. Agronomy 24:610-622; Asoegwu, S. N., 1988, Fertilizer Research 15:203-210; Asoegwu, S. N., 1987, Fruits 42:505-509; for the cultivation of lettuce see Richardson and Hardgrave, 1992, Journal of the Science of Food and Agriculture 59:345-349; for the cultivation of mint see Munsi, P. S., 1992, Acta Horticulturae 306:436-443; for the cultivation of camomile see Letchamo, W., 1992, Acta Horticulturae 306:375-384; for the cultivation of tobacco see Sisson et al., 1991, Crop Science 31:1615-1620; for the cultivation of potato see Porter and Sisson, 1991, American Potato Journal, 68:493-505; for the cultivation of *brassica* crops see Rahn et al., 1992, Conference "Proceedings, second congress of the European Society for Agronomy" Warwick Univ., p. 424-425; for the cultivation of banana see Hegde and Srinivas, 1991, Tropical Agriculture 68:331-334; Langenegger and Smith, 1988, Fruits 43:639-643; for the cultivation of strawberries see Human and Kotze, 1990, Communications in Soil Science and Plant Analysis 21:771-782; for the cultivation of songhum see Mahalle and Seth, 1989, Indian Journal of Agricultural Sciences 59:395-397; for the cultivation of plantain see Anjorin and Obigbesan, 1985, Conference "International Cooperation for Effective Plantain and Banana Research" Proceedings of the third meeting. Abidjan, Ivory Coast, p. 115-117; for the cultivation of sugar cane see Yadav, R. L., 1986, Fertiliser News 31:17-22; Yadav and Sharma, 1983, Indian Journal of Agricultural Sciences 53:38-43; for the cultivation of sugar beet see Draycott et al., 1983, Conference "Symposium Nitrogen and Sugar Beet". International Institute for Sugar Beet Research—Brussels Belgium, p. 293-303. See also Goh and Haynes, 1986, "Nitrogen and Agronomic Practice" in Mineral Nitrogen in the Plant-Soil System, Academic Press, Inc., Orlando, Fla., p. 379-468; Engelstad, O. P., 1985, Fertilizer Technology and Use, Third Edition, Soil Science Society of America, p. 633; Yadav and Sharmna, 1983, Indian Journal of Agricultural Sciences, 53:3-43.

6.16 Products of Transgenic Plants

Engineered plants exhibiting the desired physiological and/or agronomic changes can be used directly in agricultural production.

Thus, provided herein are products derived from the transgenic plants or methods of producing transgenic plants provided herein. In certain embodiments, the products are commercial products. Some non-limiting example include genetically engineered trees for e.g., the production of pulp, paper, paper products or lumber; tobacco, e.g., for the production of cigarettes, cigars, or chewing tobacco; crops, e.g., for the production of fruits, vegetables and other food, including grains, e.g., for the production of wheat, bread, flour, rice, corn; and canola, sunflower, e.g., for the production of oils.

In certain embodiments, commercial products are derived from a genetically engineered (e.g., comprising overexpression of miR167 in the pericycle of the plant) species of woody, ornamental or decorative, crop or cereal, fruit or vegetable plant, and algae (e.g., *Chlamydomonas reinhardtii*), which may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia*.

In some embodiments, commercial products are derived from a genetically engineered (e.g., comprising overexpression of miR167 in the pericycle of the plant) gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In certain embodiments, commercial products are derived from a genetically engineered (e.g., comprising overexpression of miR167 in the pericycle of the plant) woody species, such as poplar, pine, *sequoia*, cedar, oak, etc.

In other embodiments, commercial products are derived from a genetically engineered (e.g., comprising overexpression of miR167 in the pericycle of the plant) plant including, but are not limited to, wheat, cauliflower, tomato, tobacco, corn, petunia, trees, etc.

In certain embodiments, commercial products are derived from a genetically engineered (e.g., comprising overexpression of miR167 in the pericycle of the plant) crop plants, for example, cereals and pulses, maize, wheat, potatoes, tapioca, rice, sorghum, millet, cassava, barley, pea, and other root, tuber, or seed crops. In one embodiment, commercial products are derived from a genetically engineered (e.g., comprising overexpression of miR167 in the pericycle of the plant) cereal crops, including, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). In another embodiments, commercial products are derived from a genetically engineered (e.g., comprising overexpression of miR167 in the pericycle of the plant) grain plants that provide seeds of interest, oil-seed plants and leguminous plants. In other embodiments, commercial products are derived from a genetically engineered (e.g., comprising overexpression of miR167 in the pericycle of the plant) grain seed plants, such as corn, wheat, barley, rice, sorghum, rye, etc. In yet other embodiments, commercial products are derived from a genetically engineered (e.g., comprising overexpression of miR167 in the pericycle of the plant) oil seed plants, such as cotton, soybean, safflower, sunflower, *Brassica*, maize, alfalfa, palm, coconut, etc. In certain embodiments, commercial products are derived from a genetically engineered (e.g., comprising overexpression of miR167 in the pericycle of the plant) oil-seed rape, sugar beet, maize, sunflower, soybean, or sorghum. In some embodiments, commercial products are derived from a genetically engineered (e.g., comprising overexpression of miR167 in the pericycle of the plant) leguminous plants, such as beans and peas (e.g., guar, locust bean, fenugreek, soybean, garden beans, cowpea, mungbean, lima bean, fava bean, lentils, chickpea, etc.)

In certain embodiments, commercial products are derived from a genetically engineered (e.g., comprising overexpression of miR167 in the pericycle of the plant) horticultural plant, such as lettuce, endive, and vegetable brassicas including cabbage, broccoli, and cauliflower, and carnations and geraniums; tomato, tobacco, cucurbits, carrot, strawberry, sunflower, tomato, pepper, chrysanthemum, poplar, eucalyptus, and pine.

In still other embodiments, commercial products are derived from a genetically engineered (e.g., comprising overexpression of miR167 in the pericycle of the plant) corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

6.16 Kits

In one aspect, the present invention provides any of the above-mentioned compositions in kits, optionally including instructions for use of the composition e.g., for the inhibition of a gene. The "kit" typically defines a package including one or more compositions of the invention and the instructions, and/or analogs, derivatives, or functionally equivalent compositions thereof. Thus, for example, the kit can include a description of use of the composition for participation in any technique associated in the inhibition of genes. The kit can include a description of use of the compositions as discussed herein. Instructions also may be provided for use of the composition in any suitable technique as previously described. The instructions may be of any form provided in connection with the composition.

The kits described herein may also contain one or more containers, which may contain the inventive composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting and/or administrating the compositions.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition. Suitable solvents are well known, for example as previously described, and are available in the literature.

The invention also involves, in another aspect, promotion of the inhibition of miR167-regulated genes according to any of the systems or methods described herein. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention. "Instructions" can define a component of promotion, and typically involve written instructions on or associated with packaging of compositions of the invention. Instructions also can include any oral or electronic instructions provided in any manner.

7. EXAMPLE

Ectopic Overexpression of miRNA 167 in Plants Causes an Increase in Lateral Root Growth 7.1 Summary By assaying gene expression at the single cell level using a cell-specific technique developed by Birnbaum et al., 2003, Science 302, 1956-60, that is particularly sensitive for revealing gene regulation, we have been able to determine that thousands of new genes are regulated at the level of transcription in response to nitrogen treatment. Previous studies on nitrogen- (N-) regulated genes in whole root samples failed to uncover these genes. Since the newly discovered N-regulated genes included targets of known microRNAs, we postulated that microRNAs could be involved in regulating the levels of target mRNAs in response to nitrogen treatment, and that the miRNAs themselves could be regulated by nitrogen. This is indeed true for the case study miR, miR167. Using the network modeling tools developed by Gutierrez et al., 2007, Genome Biol 8, R7, we have also been able, for the first time, to confirm the association of a microRNA with a N-regulated gene network. Further, we have shown that miR167 controls N-regulation of an auxin-response transcription factor ARF8, which itself controls a variety of N-responsive target genes. Most importantly, using overexpressor miR167 lines of *Arabidopsis* and knockout arf8 lines of *Arabidopsis*, we have shown that miR167 controls a key switch involved in regulating root architecture in response to nitrogen treatment. It is noted that the *Arabidopsis* model used herein is known in the art to be a model plant system for other plant systems.

It had been shown previously that a mutation in ARF8 resulted in plants that showed increased emergence of lateral roots (Tian et al., 2004, Plant J 40, 333-43). However, these authors did not examine nutrient regulation of ARF8, nor elaborate their phenotypic characterization to show that ARF8 acts as a critical checkpoint to regulate the balance between lateral root initiation and emergence in response to nitrogen treatment. It had also been shown that miR167 regulates levels of ARF8 mRNA during flower development (Wu et al., 2006, Development 133, 4211-8). However, the presence of miR167 and the miR167-ARF8 relationship was not examined or tested in roots. Thus, the linking of nitrogen regulation of gene expression to miR167 and its role in the nitrogen regulation of ARF8 in the context of lateral root development is entirely new.

Using systems biology/network approaches to analyze the microarray data generated from N-treated plant roots, we identified the predicted mRNA targets of miR167, and developed a model for how nitrogen represses lateral root emergence via miR167 (FIG. 2B). The phenotypic effect of nitrogen applications on lateral root emergence results from the action of the miR167 to its targets to enable degradation mRNA for a group of 'checkpoint' genes that normally down-regulate lateral root emergence when nitrogen is replete. These targets include ARF8 (At5g37020) and potentially other target genes (including ARF6 (At1g30330), At2g48110, At3g19290, At3g42100 and At3g61310). Since miR167 appears to control a large group of target gene mRNAs, it is a key regulator, which has the power to control a circuit of genes involved in modulating plant root development and potentially also nutrient uptake and metabolic capacity. Targeting just a single factor, miR167, for modification in transgenic plants will thus allow the control a developmentally connected circuit of many genes at once.

7.2 Materials and Methods

Plant material. *Arabidopsis* Col0 GFP-expressing root cell lines marking the lateral root cap (E4722), epidermis and cortex (E1001), endodermis and pericycle (E470) and pericycle (E3754) were obtained from the EnhancerTraps collection developed by Dr. Scott Poethig (see worldwide web at enhancertraps.bio.upenn.edu) through the *Arabidopsis* Biological Resource Center (ABRC) at Ohio State University (FIG. 6). A GFP-expressing line marking the stele (pWOL::GFP: stele) was obtained from Bonke et al., 2003, Nature 426, 181-6. gARF8::GUS, mARF::GUS, $P_{MIR167a}$::GUS, $P_{MIR167b}$::GUS, arf8-3, arf6-2, a hemizygous population of arf6-2/arf6-2/arf8-3/+, and T1 transformants expressing 35S::miR167a were all kindly provided by Dr. Jason Reed[17] (Tian et al., 2004, Plant Physiol 135, 25-38). A GFP-tagged line reporting cytosolic Glutamine Synthetase (At5g37600) expression was obtained from ABRC (stock CS36947).

Plant Growth and Treatment.

All experiments were carried out in triplicate. Approximately 6,000 seeds (per replicate) of each GFP line used for sorted cell experiments or of Col0 for whole-root and protoplasting controls were sterilized and sown on Nitex 03-250/47 mesh (Sefar America, Bricarcliff Manor, N.Y., USA). The mesh was supported on a custom-built platform for hydroponic tissue culture inside a Phytatray (Sigma-Aldrich, St. Louis, Mo., USA) containing nitrogen and sucrose-free 1× Murashige and Skoog basal medium (custom-produced by GibcoBRL, Gaithersburg, Md., USA) supplemented with 3 mM sucrose and 0.5 mM ammonium succinate (1 mM ammonium). All components were kept sterile throughout the growth period of a 16 hr light (50 mmol photons $m^{-2}s^{-1}$ light intensity)/8 hr dark cycles at 22° C. which was maintained inside a growth incubator (Percival Scientific Inc., Perry, Iowa, USA). Approximately 200 seeds of each ARF8- and miR167-related line, and Col0 in ARF8miR167 experiments were sown in a similar fashion, but with 0.2 mM ammonium succinate. For treatments, 12 days after plants were placed into a growth chamber seedlings were treated by adding $KNO_3$ to a final concentration of 5 mM; control plants were mock-treated by adding the same concentration of KCl. For MSX-experiments plants were additionally treated with 5 mM glutamate, 5 mM glutamine, and/or 1 mM methyl sulfoximine (MSX) following Barabasi et al., 2004, Network biology: understanding the cell's functional organization. Nat Rev Genet. 5, 101-13. For isolation of GFP-expressing cells and mock-sorted protoplasts, seedling roots were harvested and subject to enzymatic digestion (see below, as Birnbaum et al., 2005, Nat Methods 2, 615-9). Otherwise whole roots were harvested and frozen immediately in $N_2$ (l) prior to RNA extraction, or harvested and incubated for 60 minutes in a solution identical to that used for protoplasting (as Birnbaum et al., 2005, Nat Methods 2, 615-9) with the exception of pectolyase and cellulysin enzymes, then frozen in $N_2$ (l). For microarray analysis of arf6-2arf8-3 and 35S::miR167a, 100 seeds of the segregating arf6-2arf6-2 arf8-3+ seed line and 300 seeds of the T1 35S::miR167a seed line were sown, seedlings treated as above with $KNO_3$ or KCl, then roots and shoots immediately harvested and frozen separately for each individual seedling. DNA from each shoot sample was extracted using the Qiagen DNeasy Plant Mini Kit isolation kit (Qiagen, Hilden, Germany) according to manufacturers instructions. arf6-2arf6-2 arf8-3/+DNA samples were PCR genotyped to identify seedlings that carried two copies of the arf8-3 allele using primers previously described in Wu et al., 2006, Development 133, 4211-8. T1 35S::miR167a DNA samples were PCR genotyped to detect the presence of the 35S::miR167a transgene using oligos designed to detect the BAR gene (5'-TCAGTTCCAAACGTAAAACGG-3' (SEQ ID NO:1) and 5'-CGTACCGAGCCGCAGGAAC-3' (SEQ ID NO:2)). RNA from seedling roots genotyped to be positive in each case was then extracted (see below).

Histology and Microscopy.

Treated and control-treated 12 day old seedlings were removed from the mesh and X-gluc activity assayed for according to Sessions et al., 1999, Plant J 20, 259-63. GUS-stained seedling roots were mounted in $dH_2O$ and viewed using Zeiss Axioskop microscope (Zeiss, Jena, Germany). Images were taken with a color digital Zeiss Axiocam camera using the Zeiss Axiovision software. GFP-expressing seedlings were viewed using a Leica TCS SP2 Laser Scanning Spectral Confocal Microscope system (Leica, Leica Microsystems GmbH, Germany). Adobe Photoshop was used to crop digital images. For assay of lateral root outgrowth 24 Col0 and 12 arf8 seedlings from phytatrays that had been supplemented at the start of the light period on day 12 with 5 mM $KNO_3$ or not supplemented (control) were removed on day 16 (4 days after treatment), mounted in $dH_2O$, and visualized using a Nikon Eclipse 90i microscope (Nikon, Tokyo, Japan). The number of (i) stage I to IV lateral root primordia, (ii) stage V to VII lateral root primordia, (iii) emerging lateral root primordia and (iv) fully emerged lateral roots (all according to Malamy et al, 1997, Development 124, 33-44) on each root were scored. During analysis a comparison was made between the total numbers of initiating lateral root primordia (i and ii) and emerging-merged (iii and iv) lateral roots. For analysis of the 35S::miR167a-segregating line treatment was carried out as above, then on the 18$^{th}$ day approximately 160 seedlings were individually harvested, the number of lateral roots counted for each while the leaves were frozen in liquid in $N_2$ (l). DNA was extracted from each leaf sample and genotyped for the presence of the 35S::miR167a-transgene in order to identify 35S::miR167a seedlings.

Plant Cell Protoplasting and Fluorescence Activated Cell Sorting.

Immediately following the two hour treatment period roots were harvested and protoplasted according to established techniques (Birnbaum et al., 2005, Nat Methods 2, 615-9). During this time the $KNO_3$-treatment of roots and resulting cells from $KNO_3$-treated seedlings was either continued (continuous treatment), or discontinued (transitory treatment) whilst protoplasting and subsequent cell-sorting was carried out. For MSX treatments of pericycle cells the $KNO_3$MSX treatment or the (KCl)/MSX-control treatment was either continued (continuous-MSX and CC-continuous-MSX), or not (transitory-MSX and CC-transitory-MSX). GFP-expressing cells were isolated on a Cytomation MoFlo fluorescence activated cell sorter (Cytomation, Fort Collins, Colo., USA) directly into lysis buffer, mixed and immediately frozen at −80° C. for RNA extraction according to Birnbaum et al., 2005, Nat Methods 2, 615-9; the non GFP-expressing sorted cells from each sort were also collected. In parallel, Col0 whole root protoplasts were isolated and stored on ice for one hour to mimic the cell sorting procedure. During this time equal volumes of sample were removed into lysis buffer and immediately frozen at −80° C. at 20 min intervals; for RNA extraction the three samples were pooled.

RNA Isolation, Quantitative PCR and Microarray Analysis.

RNA extraction from sorted or protoplasted cells, as well as from small amounts of root tissue (from the ARF8miR167 experiments) was carried out using the Qiagen RNAeasy RNA cleanup kit according to manufacturer's instructions. RNA from large amounts of whole roots was extracted with TRIzol (Invitrogen, Carlsbad, Calif.) according to manufacturer's instructions. Standard Affymetrix protocols were then used for amplifying, labeling and hybridizing RNA samples to the ATH1 GeneChip (Affymetrix, Santa Clara, Calif., USA). 50 ng RNA from sorted cells and arf6-2arf8-3 or 35S::miR167a whole roots, or 1 µg RNA from protoplasted cells and all other whole root samples was used for hybridisation; the Affymetrix small sample labeling protocol was used to amplify the 50 ng RNA samples. For quantitative RT-PCR confirmation a separate aliquot of the same sample was assayed. Double stranded cDNA was synthesized using the Invitrogen Thermoscript RT-PCR system according to manufacturer's instructions; for 50 ng RNA samples the RNA was first amplified using the Affymetrix small sample labeling protocol, and random primers instead of oligo dT were used for cDNA synthesis priming. Quantitative RT-PCR was carried out using DNA Master SYBR green labeling on a Roche LightCycler (Roche Applied Science, Mannheim, Germany) according to manufacturer's instructions. The mRNA concentration for each assayed gene was determined by normalizing expression levels relative to the highly expressed house-keeping gene Clathrin (At4g24550) and determining the quantity of mRNA according to a standard curve for each primer pair. Expression of 12 transcripts including ARF8 was tested for confirmation of genome chip results (not shown). Quantification of miR167a and miR160a expression was determined using oligos designed against the miR167a precursor (miR167aF: 5'-TCAGATGCCGGTGCACCATA-3' (SEQ ID NO:3) and miR167aR: 5'-CACCAAGTTTCGAGTAGACCGTGA-3' (SEQ ID NO:4) (as used in Wu et al., 2006, Development 133, 4211-8), and the miR160a precursor (mi160aF: 5'-GTATGCCTGGCTCCCTG-3' (SEQ ID NO:5) and miR160aR,5'-TCGATGACCTCCGTGG-3' (SEQ ID NO:6)). Quantification of mARF::GUS expression was determined by quantifying expression of the GUS gene. Clathrin and GUS were assayed using primers and probes designed by and obtained from TIB Molbiol LLC (Adelphia, N.J.), using the Roche DNA Master Hybridisation Probes kit.

Microarray Expression Normalization.

Transcript expression was normalized using the freely available dChip software (see worldwide web at dchip.org). The reproducibility of replicates was analyzed using the correlation coefficient and $r^2$ value of replicates pairs in the S-PLUS 7.0 software package (Insightful Corp., Seattle, Wash., USA). For determination of gene presence or absence a log 2 signal value cutoff of 6 was determined by examining the signal values of 25 genes that exhibit well-characterised cell-specific expression patterns across the five cell populations examined (FIG. 5).

ANOVA Analysis and Determination of Significance in Cell Populations.

All 22,746 genes that are represented on the ATH1 GeneChip (Affymetrix, Santa Clara, Calif.) were subjected to an ANOVA analysis in order to find the genes that showed the highest probability of responding to treatments within cell populations or across cell populations. The following statistical analysis was implemented in MATLAB (The Math Works, Natick, Mass., USA). (i) ANOVA filtering step. We first filtered data to obtain a list of genes that showed the most consistently variable signals with respect to treatments. We modeled a two way ANOVA with the cells as the first factor and treatments as the second factor ($Y=\mu+\alpha_{cell\ pop}+\alpha_{cell\ pop}+\alpha_{cell\ pop*treatment}+\epsilon$, where Y is the expression of a gene represented by the normalized dChip signal, µ is the global mean and the alpha coefficients correspond to the effects of cell population, treatment and the interaction between cell population and treatment). We then used ANOVA test statistics for both treatment or treatment x cell population interactions to determine the genes with a p value ≤0.05. Next we removed genes which had an ambiguous match to Affymetrix probe sequences according to the latest annotation file available from Affymetrix. We also removed any genes found to be affected by the protoplasting treatment in previous work (Birnbaum et al., 2003, Science 302, 1956-60. (ii) We then subjected the genes showing a treatment x cell population interaction to FDR analysis as implemented by Significance of Analysis of Microarrays (Tusher et. al, 2001, Proc Natl Acad Sci USA 98, 5116-21). Each category was tested separately (five cell population categories for cell x treatment responsive). The Wilcoxon test statistic was used with the maximum number of possible iterations (720). Only genes that showed a false discovery rate of 5% or less in any category were kept on the list of nitrogen-responsive genes. This enabled us to generate a categorization for each gene showing the cell population(s) that it was N-responsive in and the direction of N-response (induction or repression). For genes showing a treatment effect only we used the difference between control and treat samples to determine whether this effect was an N-induction or repression. We followed a similar procedure for both the whole root treated and the root protoplasted treated datasets. The two independent experiments revealed almost exactly the same clusters corroborating the response clusters found by the statistical analysis. We used Euclidean clustering to group N-response clusters. For statistical analysis of the effect of miR167a overexpression, ARF8 or ARF68 knock-out, or MSX treatment, clusters of genes of interest were analyzed by carrying out an un-paired t-test using the Wilcoxon test statistic with the maximum number of possible iterations. We also used chi-squared tests to examine the proportions of initiating vs emerging lateral roots.

Network Analysis.

We used the VirtualPlant online software (see worldwide web at virtualplant.org) to carry out analysis of gene lists and for network analysis of our N-regulated genes. The multinetwork that we queried to generate N-regulated networks contains information about the way that genes/proteins/metabolites are connected via metabolic, transport, protein:protein, miR:RNA and DNA-protein (regulatory) edges (described in Little et al, 2005, Proc Natl Acad Sci USA 102, 13693-8). The edges are drawn based on information in number of databases, data published in the literature, and additional predictions for protein:protein and miR:RNA interactions. In addition the latest version of the multinetwork on VirtualPlant contains DNA-protein interactions based on the presence of at least one cis element in the promoter of the target gene, combined with co-regulation of the target and regulator gene across all *Arabidopsis* microarray data that is available in the NASC repository.

7.3 Results and Discussion

Nitrate is a key required nutrient for the synthesis of amino acids, nucleotides and vitamins and is commonly considered to be the most limiting for normal plant growth (Vitousek et al., 1991, Biogeochemistry 13:87-115). Nitrogenous fertilizer is usually supplied as ammonium nitrate, potassium nitrate, or urea. Plants are keenly sensitive to nitrogen levels in the soil and, atypically of animal development, adopt their body plan to cope with their environment (Lopez-Bucio et al., 2003, Curr Opin Plant Biol 6, 280-7); Malamy et al., 2005, Plant Cell Environ 28, 67-77); Walch-Liu et al., 2006, Ann Bot (Lond) 97, 875-81). For example, mutants in several general nitrogen (N)-assimilation genes affect root architecture (Little et al., 2005, Proc Natl Acad Sci USA 102, 13693-8; Remans et al., 2006, Proc Natl Acad Sci USA 103, 19206-11). Transduction of this nitrogen signal is linked to a massive and concerted gene expression response in the root (Gutierrez et al., 2007, Genome Biol 8, R7; Wang et al., 2003, Plant Physiol 132, 556-67.

Thus, we hypothesized that N depletion followed by a short period of N influx likely environmental scenario) could elicit highly specific reactions in the plant as a developmental response mediating both morphological and metabolic changes in specialized cell types. Recent progress in cell-specific profiling now allows us to ask how the plant regulates development at the cell specific level, using enzymatic digestion of cell specific expressing fluorescent lines followed by FACS-cell sorting (Birnbaum et al., 2003, Science 302, 1956-60; Birnbaum et al, 2005, Nat Methods 2, 615-9).

To understand the cell-specific reaction to nitrogen on a global scale, we FACS sorted five specific cell populations immediately following a two hour transitory N-treatment. We used five GFP-expressing lines that sample the main cell populations of the root, the lateral root cap, epidermis and cortex, endodermis and pericycle, pericycle alone, and the stele (vascular tissues plus pericycle) (FIG. 7). We grew seedlings on low levels of ammonium for a period of 12 days to ensure nitrogen depletion at the end time point, then applied a two hour 5 mM nitrate transitory treatment to elicit N-regulation of gene expression (as Gutierrez et al., 2007, Genome Biol 8, R7). KCl-treated seedlings were used as a non-treated control. In order to address information about the persistence of the N-response, the nitrate treatment was either continued during protoplasting and cell sorting (continuous N) or nitrate was only present prior to cell sorting (transitory N). In parallel non-protoplasted (whole) Col0 roots were processed in a similar fashion (sustained and transitory N). Microarray data was normalized using dChip, filtered to remove low signal value genes, then a two-way ANOVA performed to identify genes that showed the highest probability of responding to the N-treatment within cell populations or across cell populations at a p value of ≤0.05 (see Materials and Methods). At test at a p value of ≤0.05 was used to determine N-regulation in whole roots. Previous work found protoplasting and cell sorting to have little effect on global levels of gene expression; following this study genes known to be affected by protoplasting (according to Birnbaum et al., 2003, Science 302, 1956-60) were removed from our analysis.

We found that cell specific profiling has the sensitivity to uncover N-regulation for thousands of new genes beyond what was previously known, and accurately captures cell-specific reactions in a multicellular organism. We found 5,733 genes only to be N-regulated in sorted cells, 1,780 genes to be regulated only in whole roots, and 699 genes to be regulated in both roots and cells. The 1,780 genes only in whole roots are likely to be genes that are strongly N-regulated in a cell type that we did not sample. In order to validate our cell-specific data we took three approaches. Firstly we examined the expression of a set of known cell-specific genes and found them to be expressed in the correct cell types (FIG. 5). Secondly we assayed the expression of a random sample of 12 cells-only N-regulated genes in whole roots by qPCR. We reasoned that if cell-specific, the N-regulation of genes would be barely visible in whole roots, thus a more sensitive expression technique (qPCR) would be required for detection. All 12 genes were found to be N-regulated in whole roots as predicted (e.g., 3 shown in FIG. 6); we also confirmed the cell specificity of the N-response of three of these genes by assaying their expression in sorted cells versus sorted non-GFP-marked cells (not shown). Finally we employed reporter constructs to confirm predicted patterns of N-regulation. We observed widespread N-induction for cytosolic glutamine synthetase (data not shown), and pericycle and lateral root induction for ARF8 (FIG. 3A,D).

We found that continuous- and transitory N-treatments elicited similar effects in sorted cells. This was evident on a global scale by the fact that continuous and transitory N-treatment experiment replicates clustered together (not shown). We found 3,532 genes to be N-regulated by both sustained and transitory treatment. 1,333 N-regulated genes were only N-regulated in continuous N-treated cells and 2,823 only N-regulated in transitory N-treated cells. At the gene level. N-regulation was found to be similar for both treatments. Where this differed regulation appeared to be dampened in the temporary N-treated cells (not shown), suggesting that the response of genes to nitrate is rapid and reversible. Because of this we chose to dissect the sustained-treatment data.

Figure 1C:
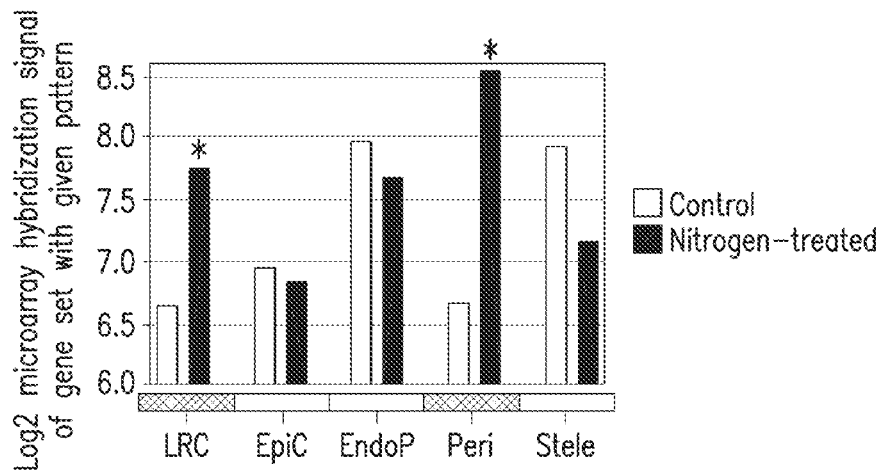
Figure 1D:
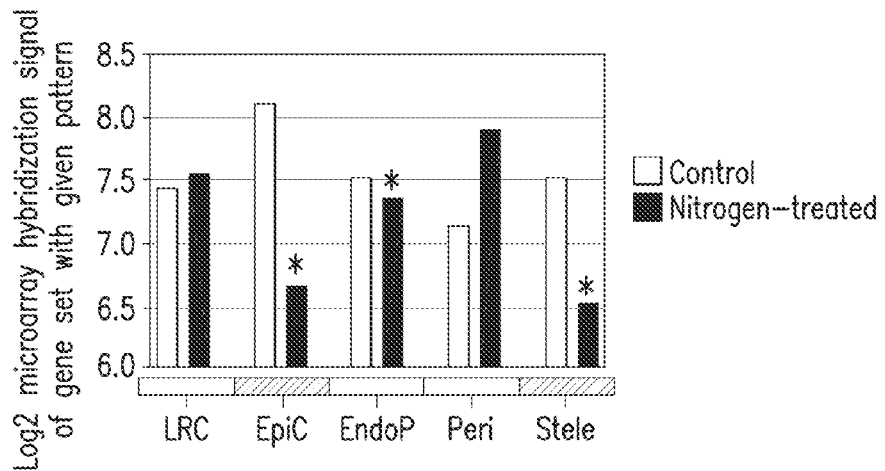
Figure 1E:
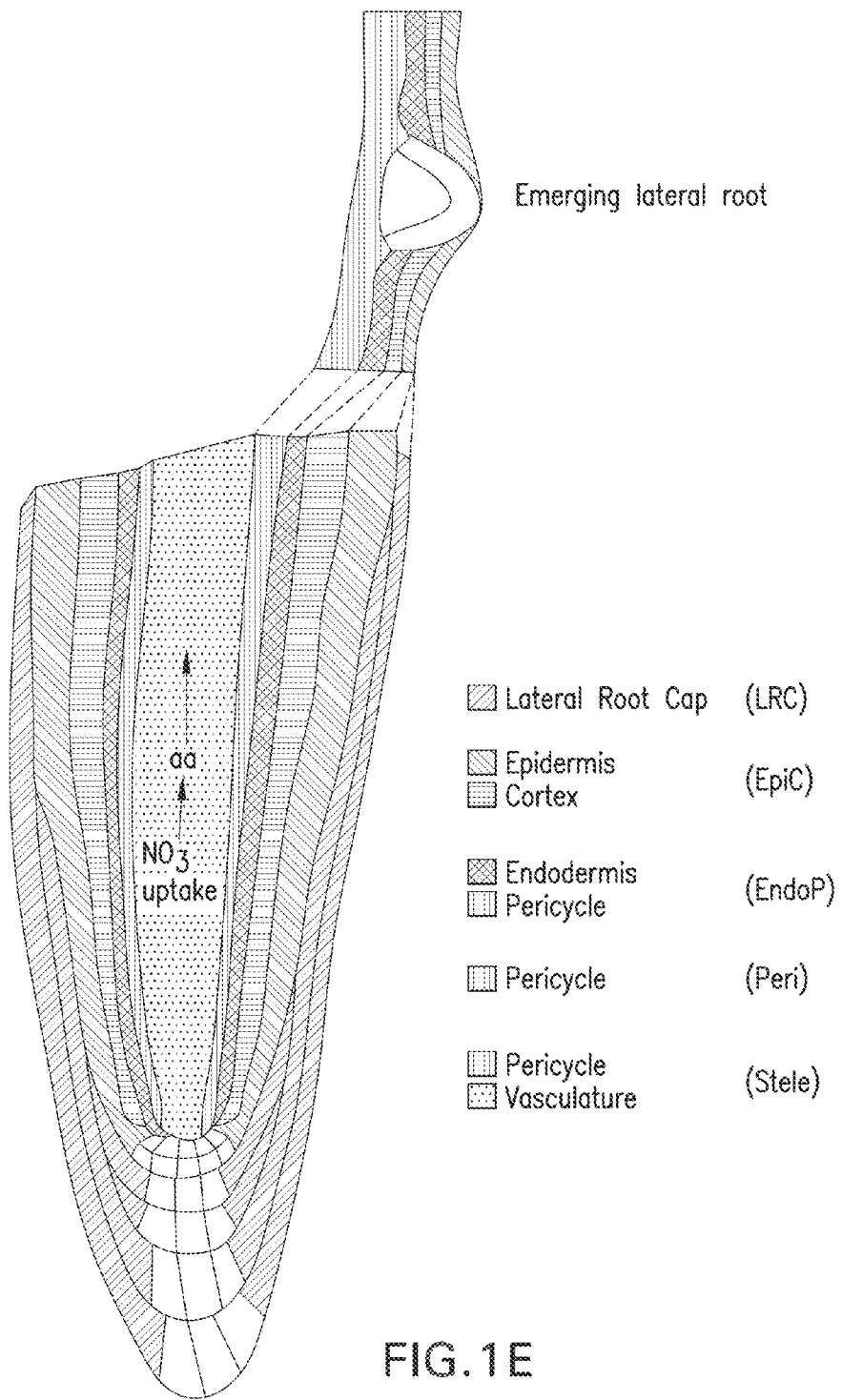

In total we found 6,355 transcripts to be regulated at the cell-specific level in a combinatorial fashion (data not shown). To classify responses we first separated genes that exhibit an overall N-regulated effect across all cell populations studied (769 genes out of 6,355), from those that are N-regulated only in 1-4 cell populations (5,586 genes out of 6,355) using a two-way ANOVA. Thus we found that a large number (88%) of genes exhibit some degree of cell-specificity in their N-response. We used a Wilcoxon t test at an FDR rate of ≤5% in order to determine in which cell population(s) these cell-specific genes were N-induced or depressed, then Euclidean clustering to create N-response clusters; we were able to categories 97% (5,426 of 5,586) of the genes. FIG. 1B shows an overview of the N-regulation pattern of all response clusters that contain more than 10 genes. We found a striking range of cell specific N-response clusters. Cluster 1 which is N-induced in all cell populations contains the majority of genes that have previously been found to be N-regulated (according to Gutierrez et al., 2007, Genome Biol 8, R7 and Wang et al., 2003, Plant Physiol 132, 556-67). This includes core enzymes involved in reducing nitrate and forming amino acids: nitrate reductases NR1, NR2, nitrite reductase NiR, NADH-dependent glutamate synthase and asparagine synthetase ASN2. Strikingly, this cluster alone accounts for 46% of all genes within this dataset that are known to be specifically regulated by nitrate, as opposed to downstream N-metabolites (according to Wang et al., 2004, Plant Physiol 136, 2512-22). This cluster of genes is expressed at a high level and induced to a strong degree (FIG. 1Ci). Together this helps account for the fact that these genes had previously been detected to be N-regulated. In contrast, the majority of N-regulated nitrate transporters were found to be consistently N-depressed (cluster 16) or induced in the pericycle and repressed in the stele (cluster 17). N-regulated amino acid transporters were found to be regulated in a cell-specific manner, often in more inner cells, and in many different types of patterns across the root (clusters 1, 13, 15, 17). Carbon and nitrogen signaling are closely linked (Palenchar et al., 2004, Genome Biol 5, R91). Core elements of carbohydrate metabolism and the pentose-phosphate pathway are also N-induced in all cells, while sucrose transporters are regulated in specific cell populations. Together this suggests that the root instigates a rapid widespread nitrate-regulation of core enzyme-encoding genes in order to assimilate nitrate and to co-ordinate C/N metabolism. The metabolic products of this response (nitrate, assimilated nitrate and sucrose) could then be selectively channeled around the root by cell-specific regulation of their transporters. Downstream N-metabolites (amino acids) could then act to regulate developmental programs within particular root types. This is evidenced by the fact that addition of the glutamate-analog MSX which blocks the enzymatic production of the amino acids glutamate and glutamine (as Rawat et al., 1999, Plant J 19, 143-52) appears to reduce the N-responsiveness of several clusters (FIG. 1B); this effect is alleviated by adding-back Glu or Gln. Regulation of downstream metabolic/developmental programs appears to include those in the GO category 'photosynthesis' which was found to be over-represented (p value $<1^{e-6}$) in genes that are N-depressed in the epidermiscortex (clusters 5, 14) (determined using the 'BioMaps' tool described in Gutierrez et al., 2007, Genome Biol 8, R7). Plastid genes which are annotated to this category have been found in legumes to be associated with a switch from nitrogen source-sink status in the root upon initiation of symbiosis with $N_2$-fixing bacteria, and it is an intriguing possibility that this could occur in Arabidopsis in response to nitrogen (Palma et al., 2006, J Exp Bot 57, 1747-58).

By comparing the levels of gene expression before or after N-treatment we found that the type of N-regulation falls into two categories: (i) simple induction/repression where the basal level of gene expression is similar across all cell populations, then N-induced or repressed in a particular pattern (e.g., cluster 1, FIG. 1Cii); or (ii) a relative alleviation of induction or repression where the basal level of gene expression is cell specific, and the 'after-N'-response is similar across all cell populations (e.g., cluster 5, FIG. 1E).

We further examined the expression of genes before and after N-treatment by using Pearson clustering to group genes based on their expression and found that expression in the endodermis/pericycle cell population was very similar to that in the pericycle-alone cell population. However gene expression between the two is markedly distinct after N-treatment. A strong induction response in the pericycle is particularly evident (FIG. 1A). Among genes that are induced in the pericycle we found the GO terms 'cell wall modification during multidimensional cell growth' and 'transmembrane receptor protein tyrosine kinase signaling pathway' to be overrepresented ($p<1^{e-3}$). Since lateral root development which involves regulation of cell growth is stimulated in the pericycle by nitrate treatment (FIG. 3L) we investigated the possibility that pericycle N-induced response clusters might regulate this process by taking a network approach and constructing a network of pericycle-induced genes.

To validate the cell specific approach we carried out a proof-of-principle study to elaborate our predictions concerning regulation of lateral root development by nitrogen at the cell-specific level. Within the pericycle-N-induced network (FIG. 2A) we found a subnetwork containing AUXIN RESPONSE FACTOR 8 (ARF8), a known modulator of root development (Tian et al., 2004, Plant J 40, 333-43) (FIG. 2B). This suggests that the ARF8 effect on lateral roots, which appears to act as an repressor of LR outgrowth, is N-dependent. ARF8 is a known target of the microRNA miR167 (Wu et al., 2006, Development 133, 4211-8), implicating miR167 repression in the N-dependent regulation of lateral root development that occurs in the pericycle cell layer. N-regulation of a microRNAs could represent anew layer of regulatory control for development. We tested this hypothesis by using GUS-expressing marker lines and transgenic lines obtained from Wu et al., 2006, Development 133, 4211-8, and by assaying expression levels using qPCR in whole roots and sorted pericycle cells (data not shown). Firstly we confirmed that ARF8 is N-induced in the pericycle (FIGS. 3A, B, C). We then confirmed that miR167 is both expressed in the pericycle, and N-regulated there by quantifying the expression of the miR167a precursor by qPCR (FIGS. 3D, E, F); to act as a control we confirmed that the miR160 precursor, which was found to have no predicted targets within our N-regulated gene dataset at a free energy of 0.72 (according to Dezulian et al., 2006, Bioinformatics 22, 359-60) was not N-regulated (not shown). We established that miR167 is involved in the N-induction of ARF8 expression levels since the N-induction of ARF8::GUS expression was lost when the miR167 target sequence in ARF8 was mutated (mARF8::GUS) (FIGS. 3G, H, I). Strikingly since the miR and target gene are expressed in the same cells this is an example of modulation of gene expression rather than complete repression/induction. We found that this N-responsive network was involved in regulating lateral root development by showing that overexpression of miR167a, and loss-of ARF8 function in the arf8-3 mutant led to N-dependent defects in lateral root development (FIG. 3L). In Col0, N-treatment results in a stimulation of lateral root initiation but also a repression of lateral root emergence (FIG. 3L). This suggests that Arabidopsis initiates lateral root primordia under conditions of high nitrate availability, but maintains these primordia in an un-emerged state until conditions of low nitrate require that they emerge to explore the surroundings in search of nitrogen. To examine a connection between ARF8 and lateral root development we first determined the targets of ARF8 transcriptional regulation (FIG. 2B, FIG. 5). We were able to confirm that the majority of our ARF8-predicted targets are likely real since they are mis-regulated during N-treatment in the arf8-3 background (FIG. 2B, evidence b). arf8-3 roots have enhanced rates of lateral root emergence vs. initiation upon N-treatment (FIG. 3L); this increased level of lateral root emergence accounts for the arf phenotype described in Tian et al., 2004, Plant J 40, 333-43. Thus the N-responsiveness of root architecture seems to be less in arf8 compared to wild-type plants.

Therefore ARF8 also appears to act as a checkpoint to inhibit lateral root emergence when nitrate is replete. As predicted, 35S::miR167a seedlings exhibit a similar phenotype, although the inhibitory effect of N is completely lost. 35S::miR167a seedlings also have even fewer lateral roots in total (FIG. 3L, right side). This suggests that miR167 acts through other targets aside from ARF8 alone to modulate lateral root development, some of these targets being inducers of lateral root development. All ARF8 predicted targets were found to be mis-regulated in the arf6-2/8-3 (FIG. 2B, evidence c) and 35S::miR167a backgrounds (FIG. 2B, evidence d), which could help to explain the reduction in lateral root numbers. ARF8 is known to act with another auxin response factor, ARF6 (FIG. 2B). While ARF6 was not to be found to be significantly N-regulated in our studies it is also a predicted miR167 target (Dezulian et al., 2006, Bioinformatics 22, 359-60) and could modulate the effects of the N-induced ARF8. In addition miR167 could act through another of its predicted targets, At3g61310 (Dezulian et al., 2006, Bioinformatics 22, 359-60) to regulate lateral root numbers according to N (FIG. 2B). Finally we found that MSX blocked the N-induction of the majority of this network in nitrate-treated pericycle-sorted cells, indicating the network to be Glu/Gln-responsive (FIG. 2B). Thus miR167/ARF8 could be the link between Glu signaling, auxin signaling and lateral root development proposed in Walch-Liu et al., 2006, Plant Cell Physiol 47, 1045-57. This also fits with our hypothesis that the assimilated products of nitrate act as cell-specific regulators to influence cell-specific developmental programs. This nitrogen-dependent lateral root response appears to be distinct from previous pathways since neither NAC1 (Guo et al., 2005, Plant Cell 17, 1376-86), ANR1 (Zhang et al., 1998, Science 279, 407-9), nor ARF7/ARF19 (Okushima et al., 2007, Plant Cell 19, 118-30) were found to be regulated by nitrogen in our studies. This network is not enriched for genes involved in auxin signaling, nor in previously characterised genes which affect lateral root development. Thus it does not appear that ARF8 is involved directly in the initiation or emergence of lateral roots, but instead in the consequences of controlling root architecture and the developmental state of lateral root primordia. The network does contain Cyclin A2; 3 which has been shown to be expressed in the root meristem (Imai et al., 2006, Plant Cell 18, 382-96). Overexpression of this gene has been found to retard the mitotic cell cycle in proliferating tissues, and affect cell expansion to result in root dwarfism (Imai et al., 2006, Plant Cell 18, 382-96). In addition CEL1, a glucanase which appears to be involved in cellulose biosynthesis, is induced by auxin and expressed in young tissues during cell expansion (Shani et al., 2006, Plant Cell Rep 25, 1067-74). These two genes could thus be involved in inducing lateral root initiation according to N, while ARF8 itself acts as a checkpoint. These findings are consistent with a growth checkpoint effect which acts upstream of auxin events that are constantly signaling to affect positioning and initiation of lateral root primordia (De Smet et al., 2007, Development 134, 681-90). The checkpoint effects of ARF8 in the root could also occur in other organs such as flowers. arf6/8 mutant flowers as well as 35S::miR167a flowers are sterile (Wu et al., 2006, Development 133, 4211-8). In addition CYC2A; 3 has been found to be expressed in inflorescences (Imai et al., 2006, Plant Cell 18, 382-96). Distinguishing possible checkpoint effects of ARF8 in flowers and roots, and separating the dual effects of miR167 on root growth vs. architecture will be our next step.

To explore factors downstream of the miR167-ARF8 circuit in the pericycle, we tested whether potential ARF8 targets exhibit coordinated responses within the pericycle. To build such a list of potential targets, we searched for genes that were induced in the pericycle (where ARF8 induction is most dramatic), that had an ARF binding site and that also showed moderate correlation (R=0.5) with ARF8 over around 1,900 microarray experiments deposited in the NASC database (Craigon et al., 2004, Nucleic Acids Res 32:D575-577). The procedure identified 126 potential targets, which are listed in Table 1, below.

TABLE 1

| AGI ID | Gene description |
|---|---|
| At1g03170 | Expressed protein |
| At1g03780 | Targeting protein-related |
| At1g07970 | Expressed protein |
| At1g10640 | Polygalacturonase |
| At1g11730 | Galactosyltransferase family protein |
| At1g12570 | Glucose-methanol-choline (GMC) oxidoreductase family protein |
| At1g14350 | Encodes a putative MYB transcription factor involved in stomata development |
| At1g15570 | Cyclin |
| At1g17110 | Ubiquitin-specific protease 15 (UBP15) gene |
| At1g22180 | SEC14 cytosolic factor family protein/phosphoglyceride transfer family protein |
| At1g24260 | Member of the MADs box transcription factor family |
| At1g25510 | Aspartyl protease family protein |
| At1g26330 | Expressed protein |
| At1g27370 | Similar to squamosa promoter-binding protein-like 11 (SPL11) At1g27360 |
| At1g30490 | Dominant PHV mutations cause transformation of abaxial leaf fates into adaxial leaf fates |
| At1g32930 | Galactosyltransferase family protein |
| At1g35780 | Expressed protein |
| At1g48100 | Glycoside hydrolase family 28 protein/polygalacturonase (pectinase) family protein |
| At1g49430 | Encodes a long chain acyl-CoA synthetase |
| At1g51790 | Leucine-rich repeat protein kinase |
| At1g52200 | Expressed protein |
| At1g55690 | SEC14 cytosolic factor family protein/phosphoglyceride transfer family protein |
| At1g62360 | Class 1 knotted-like homeodomain protein required for shoot apical meristem (SAM) formation |
| At1g63470 | DNA-binding family protein |
| At1g65370 | Meprin and TRAF homology domain-containing protein/MATH domain-containing protein |

TABLE 1-continued

| | |
|---|---|
| At1g67320 | DNA primase |
| At1g70710 | Endo-1 |
| At1g72250 | Kinesin motor protein-related |
| At1g73930 | Similar to FLJ00229 protein [*Homo sapiens*] (GB: BAB84982 |
| At1g74420 | Member of Glycosyltransferase Family- 37 |
| At1g75240 | Zinc finger homeobox family protein/ZF-HD homeobox family protein |
| At1g76420 | Identified in an enhancer trap line |
| At1g77110 | Auxin transport protein (PIN6) mRNA |
| At1g77720 | Protein kinase family protein |
| At1g79350 | DNA-binding protein |
| At1g79420 | Expressed protein |
| At2g01210 | Leucine-rich repeat transmembrane protein kinase |
| At2g02540 | Zinc finger homeobox family protein/ZF-HD homeobox family protein |
| At2g07170 | Similar to expressed protein [*Arabidopsis thaliana*] (TAIR: At4g27060 |
| At2g07690 | Minichromosome maintenance family protein/MCM family protein |
| At2g16250 | Leucine-rich repeat transmembrane protein kinase |
| At2g17930 | FAT domain-containing protein/phosphatidylinositol 3- and 4-kinase family protein |
| At2g20100 | Ethylene-responsive family protein |
| At2g20300 | Protein kinase family protein |
| At2g21050 | Amino acid permease |
| At2g23700 | Expressed protein |
| At2g25060 | Plastocyanin-like domain-containing protein |
| At2g26180 | Calmodulin-binding family protein |
| At2g26330 | Homologous to receptor protein kinases |
| At2g27040 | PAZ domain-containing protein/piwi domain-containing protein |
| At2g27980 | Expressed protein |
| At2g31320 | Poly (ADP-ribose) polymerase |
| At2g32590 | Barren family protein |
| At2g33560 | Spindle checkpoint protein-related |
| At2g34710 | Dominant PHB mutations cause transformation of abaxial leaf fates into adaxial leaf fates |
| At2g35340 | RNA helicase |
| At2g36200 | Kinesin motor protein-related |
| At2g38160 | Expressed protein |
| At2g42120 | DNA polymerase delta small subunit-related |
| At2g44440 | Emsy N terminus domain-containing protein/ENT domain-containing protein |
| At2g44830 | Protein kinase |
| At2g45870 | Expressed protein |
| At3g02110 | Serine carboxypeptidase S10 family protein |
| At3g02210 | Phytochelatin synthetase family protein/COBRA cell expansion protein COBL3 |
| At3g02640 | Expressed protein |
| At3g05750 | Similar to expressed protein [*Arabidopsis thaliana*] (TAIR: At5g26910 |
| At3g06130 | Heavy-metal-associated domain-containing protein |
| At3g06220 | Transcriptional factor B3 family protein |
| At3g10310 | Kinesin motor protein-related |
| At3g11000 | Expressed protein |
| At3g13000 | Expressed protein |
| At3g13510 | Expressed protein |
| At3g14980 | PHD finger transcription factor |
| At3g15550 | Expressed protein |
| At3g16170 | Acyl-activating enzyme 13 (AAE13) |
| At3g17840 | *Arabidopsis thaliana* AT3g17840/MEB5_6 mRNA |
| At3g20070 | Encodes a plant-specific protein of unknown function |
| At3g21310 | Expressed protein |
| At3g26932 | Similar to double-stranded RNA-binding domain (DsRBD)-containing protein At5g41070 |
| At3g29280 | Expressed protein |
| At3g32400 | Formin homology 2 domain-containing protein/FH2 domain-containing protein |
| At3g45610 | Dof-type zinc finger domain-containing protein |
| At3g50890 | Zinc finger homeobox family protein/ZF-HD homeobox family protein |
| At3g57670 | Zinc finger (C2H2 type) protein (WIP2) |
| At3g57830 | Leucine-rich repeat transmembrane protein kinase |
| At3g57920 | Squamosa promoter-binding protein |
| At3g61310 | DNA-binding family protein |
| At4g02800 | Expressed protein |
| At4g11450 | Expressed protein |
| At4g13710 | Pectate lyase family protein |
| At4g14330 | Phragmoplast-associated kinesin-related protein 2 (PAKRP2) |
| At4g17000 | Expressed protein |
| At4g18020 | Pseudo-response regulator 2 (APRR2) (TOC2) |
| At4g18820 | Expressed protein |
| At4g21326 | Subtilase family protein |
| At4g21430 | Similar to transcription factor jumonji (jmjC) domain-containing protein At1g62310 |
| At4g21550 | Transcriptional factor B3 family protein |
| At4g25110 | Similar to latex-abundant family protein (AMC1)/caspase family protein At1g02170 |
| At4g29030 | Glycine-rich protein |
| At4g30130 | Expressed protein |
| At4g32730 | Encodes a putative c-myb-like transcription factor with three MYB repeats |

TABLE 1-continued

| AGI ID | Description |
|---|---|
| At4g37750 | Ovule development protein aintegumenta (ANT) |
| At4g39010 | Glycosyl hydrolase family 9 protein |
| At5g02370 | Kinesin motor protein-related |
| At5g03680 | Trihelix DNA-binding protein |
| At5g07180 | *Arabidopsis* receptor-like kinase |
| At5g07800 | Flavin-containing monooxygenase family protein/FMO family protein |
| At5g08390 | Transducin family protein/WD-40 repeat family protein |
| At5g11160 | Adenine phosphoribosyltransferase |
| At5g11510 | AF371975 *Arabidopsis thaliana* putative c-myb-like transcription factor MYB3R-4 |
| At5g20540 | Expressed protein |
| At5g20740 | Invertase/pectin methylesterase inhibitor family protein |
| At5g25090 | Plastocyanin-like domain-containing protein |
| At5g26850 | Similar to Cyclin-related [*Arabidopsis thaliana*] (TAIR: At2g41830 |
| At5g27680 | DNA helicase |
| At5g33370 | GDSL-motif lipase/hydrolase family protein |
| At5g35930 | AMP-dependent synthetase and ligase family protein |
| At5g37020 | Auxin-responsive factor (ARF8) |
| At5g43080 | Cyclin |
| At5g51560 | Leucine-rich repeat transmembrane protein kinase |
| At5g52860 | ABC transporter family protein |
| At5g56740 | Histone acetyltransferase family protein |
| At5g60210 | Cytoplasmic linker protein-related |
| At5g60910 | Agamous-like MADS box protein AGL8/FRUITFULL (AGL8) |
| At5g64980 | Expressed protein |
| At5g67110 | Basic helix-loop-helix (bHLH) family protein |
| At5g67460 | Glycosyl hydrolase family protein 17 |

| AGI ID | Peri control | Peri N-treat | Peri control MSX | Peri N-treat MSX | Peri N-treat MSX Gln |
|---|---|---|---|---|---|
| At1g03170 | 6.629333333 | 8.987 | 6.908 | 7.898333333 | 7.536333333 |
| At1g03780 | 6.445 | 8.251666667 | 6.242666667 | 7.076 | 7.3 |
| At1g07970 | 7.720333333 | 9.912 | 7.443 | 7.775 | 9.038666667 |
| At1g10640 | 6.367 | 8.799333333 | 6.453 | 7.744333333 | 6.997 |
| At1g11730 | 6.103666667 | 8.170333333 | 6.360333333 | 6.594333333 | 7.754 |
| At1g03170 | 6.629333333 | 8.987 | 6.908 | 7.898333333 | 7.536333333 |
| At1g03780 | 6.445 | 8.251666667 | 6.242666667 | 7.076 | 7.3 |
| At1g12570 | 6.595333333 | 8.687666667 | 6.505666667 | 7.758333333 | 7.168666667 |
| At1g14350 | 6.290333333 | 7.305 | 6.303 | 6.201333333 | 6.440333333 |
| At1g15570 | 6.123666667 | 7.609666667 | 6.220333333 | 6.519333333 | 6.968 |
| At1g17110 | 7.719 | 9.454 | 7.348 | 8.486333333 | 7.590333333 |
| At1g22180 | 7.009333333 | 8.553333333 | 6.925666667 | 7.933666667 | 7.593666667 |
| At1g24260 | 5.292333333 | 6.992666667 | 5.557 | 6.047333333 | 6.253333333 |
| At1g25510 | 6.964666667 | 8.999666667 | 6.620666667 | 7.065333333 | 7.528 |
| At1g26330 | 5.851666667 | 7.893333333 | 6.155333333 | 6.869666667 | 6.676333333 |
| At1g27370 | 6.157333333 | 8.466333333 | 6.733333333 | 7.161333333 | 7.027 |
| At1g30490 | 6.891666667 | 9.640666667 | 6.964 | 7.638333333 | 7.654 |
| At1g32930 | 7.046333333 | 7.695 | 6.801 | 6.958333333 | 7.184333333 |
| At1g35780 | 8.381333333 | 9.866666667 | 8.255 | 8.413 | 9.313666667 |
| At1g48100 | 6.77 | 9.591 | 6.726333333 | 7.657333333 | 8.045333333 |
| At1g49430 | 6.039666667 | 8.640666667 | 6.123333333 | 6.694333333 | 6.830333333 |
| At1g51790 | 7.166 | 9.300333333 | 7.705333333 | 8.463666667 | 8.026666667 |
| At1g52200 | 6.136666667 | 7.614 | 6.267 | 7.199 | 6.628333333 |
| At1g55690 | 6.831 | 8.371333333 | 6.765 | 7.266666667 | 7.062 |
| At1g62360 | 6.023333333 | 8.045333333 | 6.272666667 | 6.806 | 7.001 |
| At1g63470 | 8.112333333 | 9.699 | 8.085666667 | 8.629666667 | 7.918666667 |
| At1g65370 | 6.591666667 | 8.197666667 | 6.938333333 | 7.355 | 7.414 |
| At1g67320 | 6.701666667 | 8.168666667 | 6.232333333 | 6.792333333 | 7.177666667 |
| At1g70710 | 7.179333333 | 9.242666667 | 7.381 | 7.489666667 | 8.201666667 |
| At1g72250 | 5.767 | 8.719666667 | 5.833666667 | 6.353 | 6.592666667 |
| At1g73930 | 7.087666667 | 8.759666667 | 7.102666667 | 7.332 | 7.204333333 |
| At1g74420 | 5.810666667 | 7.516666667 | 5.918333333 | 6.254333333 | 6.341333333 |
| At1g75240 | 8.085333333 | 11.25466667 | 7.581666667 | 8.741666667 | 9.291666667 |
| At1g76420 | 5.455333333 | 7.892 | 5.602 | 6.613 | 6.456666667 |
| At1g77110 | 6.595666667 | 7.818333333 | 6.587 | 7.221333333 | 7.107 |
| At1g77720 | 5.879333333 | 6.997666667 | 5.942666667 | 5.994 | 6.402333333 |
| At1g79350 | 7.392333333 | 9.181333333 | 7.391 | 7.587333333 | 7.927666667 |
| At1g79420 | 7.399 | 9.524 | 6.980666667 | 8.409666667 | 7.789 |
| At2g01210 | 5.557 | 7.320666667 | 5.092666667 | 5.822333333 | 5.971 |
| At2g02540 | 6.500666667 | 9.078666667 | 6.758 | 7.721666667 | 7.203 |
| At2g07170 | 6.563 | 7.631666667 | 6.427 | 6.910333333 | 6.443 |
| At2g07690 | 6.706 | 8.9 | 6.524333333 | 7.609333333 | 7.002333333 |
| At2g16250 | 5.965 | 7.485 | 6.353 | 6.501 | 6.680333333 |
| At2g17930 | 7.582 | 8.572 | 7.718333333 | 8.139666667 | 7.686333333 |
| At2g20100 | 6.199666667 | 5.931666667 | 5.639333333 | 5.839333333 | 6.242666667 |
| At2g20300 | 7.021666667 | 8.982 | 6.697333333 | 6.744333333 | 7.749 |
| At2g21050 | 7.104333333 | 9.603666667 | 6.763 | 7.399333333 | 7.186666667 |
| At2g23700 | 7.433 | 9.506666667 | 7.418 | 8.189333333 | 8.070666667 |
| At2g25060 | 6.901666667 | 8.078 | 6.881333333 | 7.278666667 | 7.28 |
| At2g26180 | 7.388666667 | 9.992333333 | 7.147333333 | 8.180666667 | 8.475333333 |

TABLE 1-continued

| | | | | |
|---|---|---|---|---|
| At2g26330 | 5.878 | 7.179666667 | 6.211666667 | 6.68 | 6.429666667 |
| At2g27040 | 7.801 | 9.422 | 7.734333333 | 7.647666667 | 7.523333333 |
| At2g27980 | 6.429666667 | 8.005333333 | 6.546666667 | 6.980333333 | 6.760333333 |
| At2g31320 | 6.761 | 8.918 | 6.558 | 6.625666667 | 7.365 |
| At2g32590 | 6.308666667 | 7.441 | 6.624 | 6.633666667 | 7.205666667 |
| At2g33560 | 6.314666667 | 7.893333333 | 6.188333333 | 6.793666667 | 6.855 |
| At2g34710 | 7.198666667 | 9.394333333 | 7.274333333 | 7.806333333 | 7.735666667 |
| At2g35340 | 7.081333333 | 9.589 | 7.323666667 | 8.883 | 7.776666667 |
| At2g36200 | 7.673666667 | 9.285666667 | 7.203333333 | 8.401 | 7.974666667 |
| At2g38160 | 5.758666667 | 8.303333333 | 5.999333333 | 6.653 | 6.507666667 |
| At2g42120 | 6.645666667 | 8.156333333 | 6.244 | 6.578333333 | 7.092666667 |
| At2g44440 | 6.682 | 8.576333333 | 6.836 | 7.376333333 | 7.466333333 |
| At2g44830 | 7.164666667 | 9.854 | 7.141666667 | 8.049666667 | 7.700666667 |
| At2g45870 | 5.999333333 | 6.984 | 6.218 | 6.518 | 6.576 |
| At3g02110 | 6.842333333 | 8.848666667 | 6.744333333 | 7.120666667 | 7.499 |
| At3g02210 | 9.488 | 12.07133333 | 9.066666667 | 9.991666667 | 10.617 |
| At3g02640 | 7.126333333 | 8.286666667 | 6.631666667 | 7.316333333 | 7.360666667 |
| At3g05750 | 5.134 | 5.949 | 5.267666667 | 5.435 | 5.833333333 |
| At3g06130 | 7.779 | 8.985333333 | 8.187 | 7.799666667 | 7.110666667 |
| At3g06220 | 5.238333333 | 6.497333333 | 5.280666667 | 5.806 | 5.888 |
| At3g10310 | 5.342666667 | 6.054 | 5.204333333 | 5.406 | 5.748666667 |
| At3g11000 | 5.394333333 | 7.509333333 | 5.627 | 5.956666667 | 6.068 |
| At3g13000 | 7.239 | 9.596333333 | 7.339666667 | 8.044 | 7.802 |
| At3g13510 | 6.904 | 8.812 | 6.918666667 | 7.554 | 7.346333333 |
| At3g13510 | 6.904 | 8.812 | 6.918666667 | 7.554 | 7.346333333 |
| At3g14980 | 6.367666667 | 8.789 | 6.775333333 | 6.863666667 | 7.021 |
| At3g15550 | 6.392333333 | 8.608333333 | 6.245666667 | 6.869333333 | 7.248 |
| At3g16170 | 6.768666667 | 7.89 | 6.775 | 7.220333333 | 7.347 |
| At3g17840 | 6.682666667 | 9.281333333 | 6.523666667 | 6.638666667 | 7.281333333 |
| At3g20070 | 6.313 | 7.989333333 | 6.540333333 | 6.800666667 | 6.797333333 |
| At3g21310 | 5.888666667 | 8.052333333 | 5.685333333 | 6.425333333 | 6.586 |
| At3g26932 | 4.841333333 | 6.968333333 | 4.767333333 | 5.455666667 | 5.767333333 |
| At3g29280 | 6.516 | 7.565666667 | 6.103666667 | 7.068 | 6.996 |
| At3g32400 | 5.581 | 6.424333333 | 6.088333333 | 6.019666667 | 6.224666667 |
| At3g45610 | 5.646 | 7.942333333 | 5.479666667 | 6.05 | 6.331 |
| At3g50890 | 6.034666667 | 8.649 | 5.903666667 | 6.850666667 | 6.776666667 |
| At3g57670 | 6.422 | 9.234666667 | 6.275 | 7.436333333 | 7.342666667 |
| At3g57830 | 6.463333333 | 8.503333333 | 6.479 | 6.932666667 | 7.188666667 |
| At3g57920 | 6.385666667 | 7.443666667 | 6.186 | 6.333666667 | 6.672666667 |
| At3g61310 | 6.532333333 | 8.044666667 | 6.731333333 | 7.136333333 | 7.072666667 |
| At4g02800 | 6.794333333 | 8.853666667 | 6.288666667 | 7.564666667 | 7.206333333 |
| At4g11450 | 6.694333333 | 8.830333333 | 6.832666667 | 7.21 | 7.621666667 |
| At4g13710 | 6.084666667 | 8.050666667 | 5.720333333 | 5.967 | 6.635666667 |
| At4g14330 | 5.899333333 | 7.957 | 5.962 | 6.768333333 | 6.675 |
| At4g17000 | 6.014333333 | 7.355666667 | 6.114333333 | 5.939 | 6.901333333 |
| At4g18020 | 7.304666667 | 9.041666667 | 7.239666667 | 7.917 | 7.697 |
| At4g18820 | 6.655666667 | 7.926333333 | 6.827333333 | 7.292666667 | 6.945666667 |
| At4g21326 | 5.717 | 6.696 | 6.009 | 6.650333333 | 6.482 |
| At4g21430 | 6.623666667 | 8.911333333 | 6.861 | 6.803 | 7.628666667 |
| At4g21550 | 6.343666667 | 8.313666667 | 6.621333333 | 7.009666667 | 7.127666667 |
| At4g25110 | 6.056666667 | 8.337666667 | 6.206333333 | 7.327 | 6.588666667 |
| At4g29030 | 6.849666667 | 8.580333333 | 6.637666667 | 7.178333333 | 7.343 |
| At4g30130 | 5.364666667 | 6.309333333 | 5.577 | 5.770333333 | 6.023666667 |
| At4g32730 | 9.842333333 | 11.35666667 | 9.267333333 | 9.767666667 | 10.273 |
| At4g37750 | 6.221 | 7.476333333 | 6.530333333 | 6.756333333 | 6.923666667 |
| At4g39010 | 6.672666667 | 8.810333333 | 6.708666667 | 7.605333333 | 7.294666667 |
| At5g02370 | 5.355333333 | 6.996333333 | 5.774333333 | 6.533333333 | 6.114333333 |
| At5g03680 | 5.81 | 7.621 | 5.925 | 6.446333333 | 7.164333333 |
| At5g07180 | 6.521 | 9.025333333 | 6.564333333 | 7.577333333 | 7.381333333 |
| At5g07800 | 5.726666667 | 6.798333333 | 5.929 | 6.02 | 6.394666667 |
| At5g08390 | 8.283 | 10.44566667 | 8.063333333 | 9.216666667 | 9.263 |
| At5g11160 | 6.866 | 7.75 | 6.56 | 6.631666667 | 7.227 |
| At5g11510 | 6.458333333 | 8.032 | 6.629666667 | 6.909666667 | 7.412333333 |
| At5g20540 | 9.235333333 | 11.241 | 8.630333333 | 9.738333333 | 9.211333333 |
| At5g20740 | 7.079 | 10.15533333 | 6.266 | 7.398333333 | 8.301666667 |
| At5g25090 | 6.363666667 | 8.895666667 | 6.323 | 7.242666667 | 7.277666667 |
| At5g26850 | 7.424666667 | 9.447333333 | 7.543666667 | 8.227666667 | 7.769 |
| At5g27680 | 4.872333333 | 7.236666667 | 5.111333333 | 5.733666667 | 6.488333333 |
| At5g33370 | 5.896666667 | 6.865666667 | 6.042 | 6.207333333 | 6.621333333 |
| At5g35930 | 7.115333333 | 8.889666667 | 7.311 | 8.176 | 7.686 |
| At5g37020 | 6.606333333 | 8.02 | 6.775333333 | 7.254666667 | 7.422 |
| At5g43080 | 6.434666667 | 8.283666667 | 6.339 | 7.162666667 | 7.131 |
| At5g51560 | 6.200333333 | 8.106666667 | 5.668666667 | 5.713666667 | 6.312333333 |
| At5g52860 | 6.35 | 8.370666667 | 6.596 | 6.818333333 | 7.600333333 |
| At5g56740 | 8.164 | 10.43366667 | 7.634333333 | 8.967666667 | 8.365 |

TABLE 1-continued

| At5g60210 | 7.806333333 | 9.165333333 | 8.343333333 | 8.125333333 | 7.937666667 |
| At5g60910 | 6.354333333 | 8.646333333 | 6.7 | 7.529666667 | 7.323333333 |
| At5g64980 | 4.968666667 | 6.349 | 5.462 | 5.691666667 | 5.688 |
| At5g67110 | 5.832666667 | 7.288 | 5.959333333 | 6.354 | 6.560666667 |
| At5g67460 | 6.212 | 7.625666667 | 6.337 | 6.724 | 6.992 |

To test whether the putative ARF8 module formed a cohesive response group, we asked whether ARF8 and the 126 potential targets responded similarly to either nitrate or downstream metabolites. Thus, we treated roots with nitrate and methionine sulfoximine (MSX), which blocks the assimilation of nitrate into glutamine and consequently glutamate (Rawat et al., 1999, Plant J 19:143-152), and collected pericycle cells for RNA analysis. Induction of ARF8 and all 126 of the putative ARF8 targets was blocked by MSX treatment (q<0.05 FDR), suggesting they were responsive to downstream nitrogen metabolites rather than nitrate itself (FIG. 3M). To confirm that the effect was specific to metabolite signaling, we repeated the MSX block of nitrate metabolism into glutamate/glutamine, but added glutamine, which should restore metabolite signaling if the signal is glutamine or a derived nitrogen metabolite. The induction of ARF8 and all 126 of the putative ARF8 targets was indeed restored by the glutamine "add back" (q<0.05 FDR) (FIG. 3M). No other ARFs that were induced in the pericycle showed the same coordinated regulation with this cluster. Overall, the data is consistent with ARF8 and its putative pericycle targets forming a cohesive response module under coordinated regulation by glutamine or a downstream metabolite (FIG. 3N).

Together this work suggests that the *Arabidopsis* root undergoes a concerted and rapid response to nitrate which is highly cell-specific. *Arabidopsis* metabolism appears to be coordinated in all cells of the root while simultaneously developmental processes such as lateral root development are regulated at the cell-specific level by N-assimilation products. We have revealed a mechanism by which the root regulates its branching according to levels of nitrogen which likely intersects with auxin-regulation of this process. Our results suggest a novel pathway for regulating the balance between lateral root initiation and emergence, a distinction which has not so far been examined in mutants (Malamy et al., 2005, Plant Cell Environ 28, 67-77). We have also revealed that microRNAs could act to mediate development according to nutrients, implying a new layer of developmental regulation by nutrients.

8. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties

What is claimed is:

1. A method of producing a transgenic plant having decreased ARF6-mediated nitrogen-responsiveness, said method comprising overexpressing miR167 specifically in the pericycle of the plant by transforming the plant with a polynucleotide construct comprising a sequence encoding miR167 operably linked to a pericycle-specific promoter, wherein the promoter is optionally linked to an inducible promoter element, wherein the ARF6-mediated nitrogen responsiveness is decreased in the transgenic plant as compared to a wild type plant.

2. A method of producing a transgenic plant having decreased ARF6-mediated nitrogen responsiveness, comprising: transforming a plant with a polynucleotide construct comprising a sequence encoding miR167 operably linked to a pericycle-specific promoter, wherein the promoter is optionally linked to an inducible promoter element; identifying a transgenic plant overexpressing miR167 in the pericycle from among transgenic plants having the polynucleotide construct; screening the transgenic plant overexpressing miR167 for decreased ARF-6-mediated nitrogen responsiveness as compared to a wild type plant; and selecting the transgenic plant having decreased ARF6-mediated nitrogen-responsiveness.

3. The method of claim 1 or 2, wherein the plant is a species of woody, ornamental, decorative, crop, cereal, fruit, or vegetable plant.

4. The method of claim 1 or 2, wherein said plant is a species of one of the following genuses: *Acorus, Aegilops, Allium, Amborella, Antirrhinum, Apium, Arabidopsis, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia.*

* * * * *

UNITED STATES PATENT AND TRADEMARK OFFICE
CERTIFICATE OF CORRECTION

PATENT NO. : 9,551,002 B2
APPLICATION NO. : 14/134624
DATED : January 24, 2017
INVENTOR(S) : Gloria Coruzzi et al.

Page 1 of 1

It is certified that error appears in the above-identified patent and that said Letters Patent is hereby corrected as shown below:

In the Specification

Column 1, Line 10:
Please delete "This invention was made in part with government support under Grant numbers NIH NIGMS Grant GM3287; NSF Arabidopsis 2010 Genome Grant IBN0115586; and NSF Database Activities DBI-0445666. The government has certain rights in the invention."

And insert -- This invention was made with government support under GM003287 awarded by the National Institutes of Health, and IBN0115586, and DBI0445666 awarded by the National Science Foundation. The government has certain rights in the invention. --.

Signed and Sealed this
Thirteenth Day of May, 2025

Coke Morgan Stewart
*Acting Director of the United States Patent and Trademark Office*